United States Patent
Shi et al.

(10) Patent No.: US 9,885,084 B2
(45) Date of Patent: Feb. 6, 2018

(54) ADVANCED DETECTION OF SEPSIS

(71) Applicant: Becton, Dickinson and Company, Franklin Lakes, NJ (US)

(72) Inventors: Song Shi, Reisterstown, MD (US); Richard L. Moore, Glenville, PA (US); James Garrett, Baltimore, MD (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 0 days.

(21) Appl. No.: 15/649,098

(22) Filed: Jul. 13, 2017

(65) Prior Publication Data
US 2018/0002752 A1    Jan. 4, 2018

Related U.S. Application Data

(60) Division of application No. 14/743,735, filed on Jun. 18, 2015, now Pat. No. 9,708,661, which is a continuation of application No. 14/203,367, filed on Mar. 10, 2014, now Pat. No. 9,091,698, which is a continuation of application No. 12/935,727, filed as application No. PCT/US2009/002065 on Apr. 2, 2009, now Pat. No. 8,669,113.

(60) Provisional application No. 61/123,071, filed on Apr. 3, 2008.

(51) Int. Cl.
*C12Q 1/68* (2006.01)
*G01N 33/74* (2006.01)
*G01N 33/92* (2006.01)

(52) U.S. Cl.
CPC ........... *C12Q 1/6881* (2013.01); *G01N 33/74* (2013.01); *G01N 33/92* (2013.01); *C12Q 2600/158* (2013.01); *G01N 2333/90209* (2013.01); *G01N 2333/91051* (2013.01); *G01N 2800/26* (2013.01)

(58) Field of Classification Search
None
See application file for complete search history.

(56) References Cited

U.S. PATENT DOCUMENTS

| | | |
|---|---|---|
| 4,198,389 A | 4/1980 | Wadsworth |
| 4,329,152 A | 5/1982 | Lauwerys et al. |
| 4,721,730 A | 1/1988 | Furuyoshi et al. |
| 4,770,774 A | 9/1988 | Ida et al. |
| 4,872,983 A | 10/1989 | Dimantoglou et al. |
| 4,952,323 A | 8/1990 | Nakabayashi et al. |
| 5,051,185 A | 9/1991 | Watanabe et al. |
| 5,051,371 A | 9/1991 | Nissen et al. |
| 5,093,271 A | 3/1992 | Yamamoto |
| 5,175,113 A | 12/1992 | Nissen et al. |
| 5,272,258 A | 12/1993 | Siegel et al. |
| 5,358,852 A | 10/1994 | Wu |
| 5,426,181 A | 6/1995 | Lee et al. |
| 5,484,705 A | 1/1996 | White et al. |
| 5,500,345 A | 3/1996 | Soe et al. |
| 5,639,617 A | 6/1997 | Bohuon |
| 5,646,005 A | 7/1997 | Kudsk |
| 5,780,237 A | 7/1998 | Bursten et al. |
| 5,804,367 A | 9/1998 | White et al. |
| 5,804,370 A | 9/1998 | Romaschin et al. |
| 5,830,679 A | 11/1998 | Bianchi et al. |
| 5,882,872 A | 3/1999 | Kudsk |
| 5,904,663 A | 5/1999 | Braverman et al. |
| 5,928,624 A | 7/1999 | Wright et al. |
| 5,981,180 A | 11/1999 | Chandler et al. |
| 6,077,665 A | 6/2000 | Weirich et al. |
| 6,159,683 A | 12/2000 | Romaschin et al. |
| 6,190,872 B1 | 2/2001 | Slotman |
| 6,200,766 B1 | 3/2001 | Davis |
| 6,248,553 B1 | 6/2001 | Small et al. |
| 6,251,598 B1 | 6/2001 | di Giovine et al. |
| 6,268,222 B1 | 7/2001 | Chandler et al. |
| 6,303,321 B1 | 10/2001 | Tracey et al. |
| 6,316,199 B1 | 11/2001 | Vockley et al. |
| 6,376,202 B1 | 4/2002 | Davis |
| 6,406,862 B1 | 6/2002 | Krakauer |
| 6,416,487 B1 | 7/2002 | Braverman et al. |
| 6,420,526 B1 | 7/2002 | Ruben et al. |
| 6,423,505 B1 | 7/2002 | Davis |
| 6,534,648 B1 | 3/2003 | Pardy et al. |
| 6,548,646 B1 | 4/2003 | Ebrahim et al. |
| 6,579,719 B1 | 6/2003 | Hutchens et al. |
| 6,592,822 B1 | 7/2003 | Chandler |
| 6,599,331 B2 | 7/2003 | Chandler et al. |

(Continued)

FOREIGN PATENT DOCUMENTS

| EP | 1355158 A1 | 10/2003 |
|---|---|---|
| EP | 1355159 A1 | 10/2003 |

(Continued)

OTHER PUBLICATIONS

Members of the American College of Chest Physicians/Society of Critical Care Medicine Consensus Conference Committee, "American College of Chest Physicians/Society of Critical Care Medicine Consensus Conference: definitions for sepsis and organ failure and guidelines for the use of innovative therapies in sepsis," Crit Care Med. 20(6): 864-874 (1992).

Adam et al., "Serum protein fingerprinting coupled with a pattern-matching algorithm distinguishes prostate cancer from benigh prostate hyperplasia and healthy men", Canc Res. (2002) 62:3609-3614.

Affymetrix, "Gene Chip Human Genome UI33 Set," (product description) retrieved May 21, 2003 from Affymetrix Official Site website: http://www.affymetrix.com (copy obtained from European Patent Office).

Ambroise et al., "Selection bias in gene extraction on the basis of microarray gene-expression data," Proc. Nat'l Acad. Sci. USA 99(10): 6562-66 (2002).

(Continued)

*Primary Examiner* — Lisa V Cook
(74) *Attorney, Agent, or Firm* — Knobbe, Martens, Olson & Bear, LLP

(57) ABSTRACT

The present invention relates to methods, monitors and systems, useful, for example, for advanced detection of sepsis in a subject.

27 Claims, 9 Drawing Sheets

(56) References Cited

U.S. PATENT DOCUMENTS

| | | | |
|---|---|---|---|
| 6,675,104 B2 | 1/2004 | Paulse et al. |
| 6,682,741 B1 | 1/2004 | Ribaudo et al. |
| 6,692,916 B2 | 2/2004 | Bevilacqua et al. |
| 6,756,483 B1 | 6/2004 | Bergmann et al. |
| 6,838,250 B2 | 1/2005 | Scalice et al. |
| 6,872,541 B2 | 3/2005 | Mills |
| 6,930,085 B2 | 8/2005 | Fogelman et al. |
| 6,951,727 B2 | 10/2005 | Davis |
| 6,960,439 B2 | 11/2005 | Bevilacqua et al. |
| 6,964,850 B2 | 11/2005 | Bevilacqua et al. |
| 7,015,022 B2 | 3/2006 | Laskin et al. |
| 7,465,555 B2 | 12/2008 | Anderson et al. |
| 7,645,573 B2 | 1/2010 | Ivey et al. |
| 7,767,395 B2 | 8/2010 | Garrett et al. |
| 7,807,696 B2 | 10/2010 | Al-Abed et al. |
| 8,183,050 B2 * | 5/2012 | Shi | C12Q 1/26 424/78.05 |
| 8,669,113 B2 * | 3/2014 | Shi | G01N 33/92 436/71 |
| 9,091,698 B2 * | 7/2015 | Shi | G01N 33/92 |
| 9,708,661 B2 * | 7/2017 | Shi | G01N 33/92 |
| 2001/0051344 A1 | 12/2001 | Shalon et al. |
| 2002/0019704 A1 | 1/2002 | Tusher et al. |
| 2002/0119554 A1 | 8/2002 | Vockley et al. |
| 2002/0150534 A1 | 10/2002 | Yu et al. |
| 2003/0004402 A1 | 1/2003 | Hitt et al. |
| 2003/0027176 A1 | 2/2003 | Dailey |
| 2003/0044790 A1 | 3/2003 | Das et al. |
| 2003/0049851 A1 | 3/2003 | Toh et al. |
| 2003/0057106 A1 | 3/2003 | Shen et al. |
| 2003/0059937 A1 | 3/2003 | Ruben et al. |
| 2003/0087285 A1 | 5/2003 | Chow et al. |
| 2003/0091565 A1 | 5/2003 | Beltzer et al. |
| 2003/0100122 A1 | 5/2003 | Heinecke et al. |
| 2003/0165919 A1 | 9/2003 | Schmitz et al. |
| 2003/0194752 A1 | 10/2003 | Anderson et al. |
| 2003/0207278 A1 | 11/2003 | Khan et al. |
| 2003/0219771 A1 | 11/2003 | Bevilacqua et al. |
| 2003/0223996 A1 | 12/2003 | Ruben et al. |
| 2003/0228625 A1 | 12/2003 | Toh et al. |
| 2003/0228648 A1 | 12/2003 | Laskin et al. |
| 2003/0229455 A1 | 12/2003 | Bevilacqua et al. |
| 2003/0235816 A1 | 12/2003 | Slawin et al. |
| 2004/0009503 A1 | 1/2004 | Fu et al. |
| 2004/0038201 A1 | 2/2004 | Nau et al. |
| 2004/0072237 A1 | 4/2004 | Schweitzer |
| 2004/0096917 A1 | 5/2004 | Ivey et al. |
| 2004/0097460 A1 | 5/2004 | Ivey et al. |
| 2004/0106142 A1 | 6/2004 | Ivey et al. |
| 2004/0121343 A1 | 6/2004 | Buechler et al. |
| 2004/0121350 A1 | 6/2004 | Anderberg et al. |
| 2004/0126767 A1 | 7/2004 | Anderberg et al. |
| 2004/0133352 A1 | 7/2004 | Bevilacqua et al. |
| 2004/0157242 A1 | 8/2004 | Ivey et al. |
| 2004/0175754 A1 | 9/2004 | Bar-Or et al. |
| 2004/0180396 A1 | 9/2004 | Bergmann et al. |
| 2004/0219568 A1 | 11/2004 | Bevilacqua et al. |
| 2004/0225447 A1 | 11/2004 | Bevilacqua et al. |
| 2004/0225449 A1 | 11/2004 | Bevilacqua et al. |
| 2004/0253637 A1 | 12/2004 | Buechler et al. |
| 2004/0259090 A1 | 12/2004 | Zipel et al. |
| 2005/0009074 A1 | 1/2005 | Thompson |
| 2005/0037344 A1 | 2/2005 | Stuhmuller et al. |
| 2005/0059104 A1 | 3/2005 | Bergmann |
| 2005/0060101 A1 | 3/2005 | Bevilacqua et al. |
| 2005/0064506 A1 | 3/2005 | Bergmann |
| 2005/0069958 A1 | 3/2005 | Mills et al. |
| 2005/0074811 A1 | 4/2005 | Bergmann |
| 2005/0079490 A1 | 4/2005 | Stuber et al. |
| 2005/0106645 A1 | 5/2005 | Bergmann |
| 2005/0130242 A1 | 6/2005 | Bergmann et al. |
| 2005/0148029 A1 | 7/2005 | Buechler et al. |
| 2005/0164238 A1 | 7/2005 | Valkirs et al. |
| 2005/0196817 A1 | 9/2005 | Kingsmore et al. |
| 2005/0239150 A1 | 10/2005 | Bergmann |
| 2005/0249724 A1 | 11/2005 | Lihme et al. |
| 2005/0250148 A1 | 11/2005 | Bevilacqua et al. |
| 2006/0024744 A1 | 2/2006 | Mills et al. |
| 2006/0062789 A1 | 3/2006 | Ruben et al. |
| 2006/0127912 A1 | 6/2006 | Pachot |
| 2006/0211752 A1 | 9/2006 | Kohn et al. |
| 2006/0241040 A1 | 10/2006 | Visintin et al. |
| 2006/0246495 A1 | 11/2006 | Garrett et al. |
| 2007/0021465 A1 | 1/2007 | Al-Abed et al. |
| 2007/0111316 A1 | 5/2007 | Shi et al. |
| 2007/0184512 A1 | 8/2007 | Ivey et al. |
| 2008/0050829 A1 | 2/2008 | Ivey et al. |
| 2011/0105350 A1 | 5/2011 | Garrett et al. |
| 2011/0118569 A1 | 5/2011 | Shi et al. |
| 2014/0141435 A1 | 5/2014 | Garrett et al. |
| 2014/0302533 A1 | 10/2014 | Shi et al. |
| 2016/0168638 A1 | 6/2016 | Garrett et al. |

FOREIGN PATENT DOCUMENTS

| | | |
|---|---|---|
| EP | 1369693 | 12/2003 |
| EP | 1940231 B1 | 5/2011 |
| JP | 09033525 A | 2/1997 |
| JP | 2002-017938 | 1/2002 |
| JP | 2003524762 | 8/2003 |
| RU | 2072103 | 1/1997 |
| SU | 1504597 | 8/1989 |
| WO | WO 1992/021364 | 12/1992 |
| WO | WO 1994/028418 | 12/1994 |
| WO | WO 1995/020163 | 7/1995 |
| WO | WO 1996/041291 | 12/1996 |
| WO | WO 1998/001738 | 1/1998 |
| WO | WO 1999/020756 | 4/1999 |
| WO | WO 2000/042222 | 7/2000 |
| WO | WO 2000/046603 | 8/2000 |
| WO | WO 2000/052472 | 9/2000 |
| WO | WO 2001/004630 | 1/2001 |
| WO | WO 2001/063280 | 8/2001 |
| WO | WO 2001/096864 | 12/2001 |
| WO | WO 2002/042733 | 5/2002 |
| WO | WO 2002/058721 | 8/2002 |
| WO | WO 2002/088744 | 11/2002 |
| WO | WO 2002/088747 | 11/2002 |
| WO | WO 2003/048776 | 6/2003 |
| WO | WO 2003/048777 | 6/2003 |
| WO | WO 2003/048778 | 6/2003 |
| WO | WO 2003/048782 | 6/2003 |
| WO | WO 2004/005539 | 1/2004 |
| WO | WO 2004/043223 | 5/2004 |
| WO | WO 2004/043236 | 5/2004 |
| WO | WO 2004/044554 | 5/2004 |
| WO | WO 2004/044555 | 5/2004 |
| WO | WO 2004/044556 | 5/2004 |
| WO | WO 2004/053148 | 6/2004 |
| WO | WO 2004/053155 | 6/2004 |
| WO | WO 2004/053457 | 6/2004 |
| WO | WO 2004/008138 | 8/2004 |
| WO | WO 2004/086043 | 10/2004 |
| WO | WO 2004/087949 | 10/2004 |
| WO | WO 2004/088324 | 10/2004 |
| WO | WO 2005/048823 | 6/2005 |
| WO | WO 2005/064307 | 7/2005 |
| WO | WO 2005/065015 | 7/2005 |
| WO | WO 2005/078456 | 8/2005 |
| WO | WO 2006/061644 | 6/2006 |
| WO | WO 2006/077471 | 7/2006 |
| WO | WO 2006/085984 | 8/2006 |
| WO | WO 2006/102408 | 9/2006 |
| WO | WO 2007/038758 | 9/2007 |
| WO | WO 2009/123737 | 1/2010 |

OTHER PUBLICATIONS

Angus et al., "Epidemiology of severe sepsis in the United States: analysis of incidence, outcome, and associated costs of care," Crit Care Med. 29(7): 1303-1310 (2001).

Anthony et al., "Rapid diagnosis of bacteremia by universal amplification of 23S ribosomal DNA followed by hybridization to an oligonucleotide array," J. Clin. Microbiol. 38(2): 781-788 (2000).

(56) References Cited

OTHER PUBLICATIONS

Asadullah et al., "Immunodepression Following Neurosurgical Procedures," Crit Care Med 23(12):1976-1983 (1995).
Balci et al., "Usefulness of procalcitonin for diagnosis of sepsis in the intensive care unit", Crit Care (2003); 7:85-90 and Erratum.
Barth et al., "Peaks of Endogenous G-CSF Serum Concentrations are followed by an Increase in Respiratory Burst Activity of Granulocytes in Patients with Septic Shock," Cytokine, 17:275-284 (2002).
BD Cytometric Bead Array (CBA), 2004, "Human Inflammation Kit Instruction manual", BD Biosciences. Kit Instruction Manual, BD Biiosciences.
Beloborodova et al., 2000, "Small molecules originating from microbes (SMOM) and their role in microbes-host relationship," Microb. Ecol. Health and Disease; 12:12-21.
Beutler et al., "From phenomenon to phenotype and from phenotype to gene: Forward genetics and the problem of sepsis," J Infect Dis. 187(Suppl. 2):S321-326 (2003).
Bone et al., "Definitions for Sepsis and Organ Failure," Critical Care Medicine 20(6): 724-726 (1992).
Bozza et al., "Beyond sepsis pathophysiologywith cytokines: what is their value as biomarkers for disease severity?" Mem Inst Oswaldo Cruz, (2005) 100(1):271-221.
Bright el al., "Rapid typing of bacteria using matrix-assisted laser desorption ionization time-of-flight mass spectrometry and pattern recognition software," J Microb Methods 48:127-138 (2002).
Brunkhorst et al., "Procalcitonin for early diagnosis and differentiation of SIRS, sepsis, severe sepsis, and septic shock", Intens Care Med. (2000) 26:S148-152.
Brunkhorst et al., "Diagnostic approach to sepsis—State of the art," Zentralblatt für Chirurgie; 127(3):165-173 (2002).
Bulger et al., "Lipid mediators in the pathophysiology of critical illness", Crit Care Med. (2000) 28(4) Suppl.; pp. N27-N36.
Calandra, T., "Pathogenesis of Septic Shock: Implications for Prevention and Treatment", Chemother. (2001) 13(1):173-180.
Cariou et al., "The era of genomics: impact on sepsis clinical trial design," Crit. Care Med. 30(Suppl.):S341-S348 (2002).
Carraway et al., "Differential Expression of Arginase andiNOS in the Lung in Sepsis," Exp. Lung Res., 24(3):253-268 (1998).
Chan E. "Integrating transcriptomics and proteomics." Genomics & Proteomics, available online from www.genpromag.com, pp. 1-5.
Cheadle, "The Human Leukocyte Antigens and Their Relationship to Infection," Am J Surgery 165 (2A Suppl):75S-81S (1993).
Cheung et al., "Natural variation in human gene expression assessed in lymphoblastoid cells." Nat Genet. (2003) 33(3):422-425.
Chinnaiyan et al., "Molecular signatures of sepsis: Multiorgan gene expression profiles of systemic inflammation," Am J Pathol. 159(4):1199-1209 (2001).
Christie, W.W., "Phosphatidylcholine and Related Lipids: Structure, Occurrence, Biochemistry and Analysis," Scottish Crop Research Institute (and Mylnefield Lipid Analysis), Invergowrie, Dundee (DD2 5DA), Scotland (Feb. 6, 2006).
Cobb et al., 2002, "Sepsis gene expression profiling: murine splenic compared with hepatic responses determined by using complementary DNA microarravs," Crit. Care Med. 30(12):2711-2721.
Creighton et al., "Expression of matrix metalloproteinase 9 (MMP-9/gelatinase B) in adenocarcinomas strongly correlated with expression of immune response genes," In Silico Biol. 3(3):301-311 (2003).
Dalluge, "Mass spectrometry for direct determination of proteins in cells: applications in biotechnology and microbiology," Fresenius J Anal Chem. 366:701-11 (2000).
Das, Undurti., "Role of lipids in sepsis", Crit Care Shock, Indonesian Soc of Crit Care Med. (2004) 7(2):87-92.
Das, Undurti., "Can Sepsis and Other Critical Illnesses be Predicted and Prognosticated?", Advances in Sepsis, 5(2):52-59 (2006).
DeBont et al., "Plasma IL-8 and IL-6 Levels can be used to Define a Group of Low Risk of Septicaemia Among Cancer Patients with Fever and Neurtopenia," Brit J Haematol. 107:375-380 (1999).
Desborough et al., "The Stress Response to Trauma and Surgery," Br. J. Ananesth, 85:109-17 (2000).
Ditschkowski et al., "HLA-DR Expression and Soluble HLA-DR Levels in Septic Patients after Trauma," Ann Surg. 229(2):246-254 (1999).
Døllner et al., 2001, "Early diagnostic markers for neonatal sepsis: Comparing C-reactive protein, interleukin-6, soluble tumour necrosis factor receptors and soluble adhesion molecules," J Clin Epidemiol; 54(12): 1251-1257.
Drobnik et al., 2003, "Plasma ceramide and lysophosphatidylcholine inversely correlate with mortality in sepsis patients," J Lipid Res; 44(4):754-761.
Ernst et al., "Three Genes for the Human High Affinity Fe Receptor for IgG (FcγRI) Encode Four Distinct Transcription Products," J Biol. Chem., 267(22)1 5692-15700 (1992).
Feezor et al., 2003, "Molecular Characterization of the Acute Inflammatory Response to Infections with GramNegative versus Gram-Positive Bacteria," Infect Immun; 71(10):5803-13.
Fischer et al., "CD64 Surface Expression on Neutrophils is Transiently Upregulated in Patients with Septic Shock," Int Care Med., 27(12):1848-1852 (2001).
Fung et al., 2002, "ProteinChip® Clinical Proteomics: Computational Challenges and Solutions," Biotechniques; 32 Suppl:S34-S41.
Gagnon et at., "Endoplasmic reticulum-mediated phagocytosis is a mechanism of entry into macrophages," Cell 110:119-131 (2002).
Gaut et al., 2001, "Neutrophils employ the myeloperoxidase system to generate antimicrobial brominating and chlorinating oxidants during sepsis," Proc Natl Acad Sci USA; 98(21):11961-11966.
GenBank Locus AY442689, "Mus musculus osmosensing scaffold for MEKK3 mRNA, complete cds." (2003) from www.ncbi.nlm.nik.gov; pp. 1-3.
GenBank Locus NM_001966, Homo sapiens enoyl-Coenzyme A, hydratase/3-hydroxyacyl Coenzyme A dehydrogenase (EHHADH), mRNA. from www.ncbi.nlm.nih.gov, 4 pages.
GenBank Locus NM_004139, Homo sapiens lipopolysaccharide binding protein (LBP), mRNA. from www.ncbi.nlm.nih.gov, 7 Pages.
Genbank GI:13543892, "Homo sapiens Matrix Metallopeptidase 9 (gelatinase B, 92kDa Gelatinase, 92kDa Type IV Collagenase), mRNA (cDNA Clone MGC:I2688 Image:4054882)," Complete CDS pp. 1-5.
Genbank NM_000566 [GI:24431940], Oct. 31, 2002, Homo sapiens c fragment of IgG, high affinity la, receptor (CD64) (FCGRIA), mRNA, pp. 1-4, downloaded from http://www.ncbi.nlm.nih.gov/entrez/viewer.fcgi?db—nuccore&id~24431940.
Genbank NM_OO 1172 [GI: 1094711 O], Oct. 23, 2000, Homo sapiens arginase, type II (ARG2), nuclear gene encoding mitochondrial protein, mRNA, pp. 1-3, downloaded from http://www.ncbi.nlm.nih.gov/entrez/viewer.fcgi?val~ 10947110.
Giannoudis et al., "Stimulation of Inflammatory Markers after Blunt Trauma," Brit J Surg. 85:986-990 (1998).
Groeneveld et al., "Circulating inflammatory mediators in patients with fever: predicting bloodstream infection," Clin Diag Lab Immunol. 8(6): 1189-1195 (2001).
Hagberg, "From magnetic resonance spectroscopy to classification of tumors: a review of pattern recognition methods," NMR Blomed. 11:148-156 (1998).
Harbarth et al., 2001, "Diagnostic value of procalcitonin, interleukin-6, and interleukin-8 in critically ill patients admitted with suspected sepsis," Am J Respir Crit Care Med; 164(3):396-402.
Hastie et al., The Elements of Statistical Learning (Springer-Verlag 2001); 16.pages.
Healy, "New and emerging therapies for sepsis," Annuls Pharmacother. 36:648-654 (2002).
Hecker et al., "Inhibition of Arginase by NG-hydroxy-L-arginine in Alveolar Macrophages: Implications for the Utilization of L-Arginine for Nitric Oxide Synthesis," FEBS Letters, 359:251-254 (1995).

(56) References Cited

OTHER PUBLICATIONS

Hey et al., "Nitric Oxide Synthase Activity is Inducible in Rat, but not Rabbit Alveolar Macrophages, with a Concomitant Reduction in ArginaseActivity," Naunyn Schmiedebergs Arch Pharmacol., 351(6):651-659 (1995).
Hirayama et al., "Concentrations of Tluombopoietin in Bone Marrow in Normal Subjects and in Patients With Idiopathic Thrombocytopenic Purpura, Aplastic Anemia, and Essential Thrombocythemia Correlate With Its mRNA Expression of Bone Marrow Stromal Cells." Blood, 92:46-52, (1998).
Holmes et al., "Genetic Polymorphisms in Sepsis and Septic Shock: Role in Prognosis and Potential for Therapy", Chest, (2003) 124: 1103-1115.
Hoshikawa et al., "Hypoxia induces different genes in the lungs of rats compared with mice." Physiol Genomics. (2003) 12(3):209-19.
Jackson et al., "Lysophospholipid acyltransferases in monocyte inflammatory responses and sepsis", Immunobiol. (2004) 209(1-2):31-38.
Jacoby et al., "Platelet Activiation and Function after Trauma," J. Trauma 51(4):639-47 (2001).
Joyce et al., "Gene Expression Profile of antithrombotic protein C defines new mechanisms modulating inflammation and apoptosis." J Biol Chem. 276(14): 11199-11203 (2001).
Karzai et al., "Sepsis: definitions and diagnosis," Int'l J Crit Practice 95(Suppl.): 44-48 (1998).
Kinasewitz et al., Universal changes in biomarkers of coagulation and inflammation occur in patients with severe sepsis, regardless of causative micro-organism, Crit Care, (2004), 8(2):R82-R90.
Knaus et al., "APACHE II: a severity of disease classification system," Crit Care Med. (1985) 13(10):818-829.
Knaus et al., "The APACHE III Prognostic System—Risk Prediction of Hospital Morality for Critically Ill Hospitalized Adults," Chest 100 (6):1619-1636 (1991).
Küster et al., 1998, "Interleukind receptor antagonist and interleukin-6 for early diagnosis of neonatal sepsis 2 days before clinical manifestation," Lancet 352(9136):1271-1277.
Lakhani et al., "Toll-like receptor signaling in sepsis", Curr. Opin. Pediatr. (2003) 15(3):278-282.
Lam et al., "Time course of early and late changes in plasma DNA in trauma patients," Clin. Chem. 49(8): 1286-1291 (2003).
Layseca-Espinosa et al., "Expression ofCD64 as a Potential Marker of Neonatal Sepsis," Pediatr Allergy Immunol., 13(5):319-327 (2002).
Levy et al., "2001 SCCN/ESICM/ACCP/ATS/SIS International Sepsis Defnitions Conference," Intensive Care Med. 29(4):530-538 (2003).
Lissauer et al., "Decreased Tysophosphatidylcholine levels are associated with sepsis compared to uninfected inflammation prior to onset of sepsis", J Surg Res. (2007) 137(2):206.
Llewelyn et al., "Diagnosis of infection in sepsis," Intens Care Med. 27(Suppl 1):S10-S32 (2001).
Manjuck et al., "Decreased Response to Recall Antigens is Associated with Depressed Costimulatory Receptor Expression in Septic Critically Ill Patients," J Lab Clin Med. 135(2)153-160 (2000).
Marshall et al., "Measures, markers, and mediators: Toward a staging system for clinical sepsis. A report from the Fifth Toronto Sepsis Roundtable, Toronto, Ontario, Canada, Oct. 25-26, 2000," Crit Care Med. 31(5):1560-1567 (2003).
Mehta, 2005, "Lysophosphatidylcholine: An Enigmatic Lysolipid", Am. J. Physiol. Lung Cell. Mol. Physiol., 289:L174-L175.
Millili et al., "Predicting Surgical Outcome Using Bayesian Analysis," J Surg Res. 77:45-49 (1998).
Müller et al., "Calcitonin Precursors are Reliable Markers of Sepsis in a Medical Intensive Care Unit," Crit Care Med. 4:977-983 (2000).
Muller Kobold et al., "Leukocyte activation in sepsis; correlations with disease state and mortality," Intensive Care Med, 26(7):883-892 (2000).

Muret et al., "Ex vivo T-lymphocyte derived cytokine productionin in SIRS patients is fluenced by experimental procedures", Shock 13(3):169-174 (2000).
Nadel, "Helping to understand studies examining genetic susceptibility to sepsis," Clin Exp Immunol. 127: 191-192 (2002).
Natanson et al., "The sirens' songs of confirmatory sepsis trials: selection bias and sampling error," Crit. Care Med. 26(12):1927-1931 (1998).
Nupponen et al., "Neutrophil CD11b Expression and Circulating Interleukin-8 as Diagnostic Markers for Early-Onset Neonatal Sepsis," Pediatrics 108(1 ):1-6 (2001 ).
OBerholzer et al., "Sepsis syndromes: understanding the role of innate and acquired immunity," Shock 16: 83-96 (2001).
Oczenski, "HLA-DR as a Marker for Increased Risk for Systemic Inflammation and Septic Complications after Cardiac Surgery," Int Care Med. 29:1253-1257 (2003).
Paterson et al., Sepsis and the systemic inflammatory response syndrome, J R Coll. Surg Edinb. 45:178-182 (2000).
Pathan et al., 2003, "The complexity of the inflammatory response to the meningococcal sepsis revealed by gene expression profiling using cDNA microarrays," Crit. Care Med; 31(12 Suppl.): A47.
Perry et al., "Is Low Monocyte HLA-DR Expression Helpful to Predict Outcome in Severe Sepsis?" Int Care Med. 29:1245-1252 (2003).
Petricoin et al., "Use of proteomic patterns in serum to identify ovarian cancer," Lancet 359: 572-577 (2002).
Presto Elgstoen et al., 2001, "Potential of capillary electrophoresis, tandem mass spectrometry and coupled capillary electrophoresis-tandem mass spectrometry as diagnostic tools," J. Chromatogr. A; 914: 265-275.
Pugin, et al., "Human Neutrophils Secrete Gelatinase B In Vitro and In Vivo in Response to Endotoxin and Pro-inflammatory Mediators", Am J Resp Cell Molec Biol. (1999) 20(3):458-464.
Rangel-Frausto et al., "The natural history of the systemic inflammatory response syndrome (SIRS)," J Am Med Ass'n. 273:117-123 (1995).
Rangel-Frausto et al., "The Dynamics of Disease Progression in Sepsis: Markov Modeling Describing the Natural History and the Likely Impast of Effective Antisepsis Agents," Clinical Infectious Diseases 27:185-190 (1998).
Read et al., "Toll receptors and sepsis", Curr. Opin. Crit. Care (2001) 7(5):371-375.
Reinhart et al., "Markers of endothelial damage in organ dysfunction and sepsis," Crit Care Med. 30(5): S302•S312 (2002).
Rixen et al., "'Sepsis/SIRS', Physiologic Classification, Severity Stratification, Relation to Cytokine Elaboration and Outcome Prediction in Posttrauma Illness," J. Trauma 41(4):581-598 (1996).
Ross et al., "Classification of pediatric acute lymphblastic leukemia by gene expression profiling", Blood (2003) 102(8):2951-2959.
Roumen et al., "Scoring systems and blood lactate concentrations in relation to the development of Adult Respiratory Distress Syndrome and Multiple Organ Failure in severely traumatized patients," J. Trauma 35(3):349-355 (1993).
Sage, L., "Research Profile Digging for disease markers of sepsis", J. Proteome Res. (2006) 5(11):2885.
Sambrook et al., Molecular Cloning (3rd Ed., Cold Spring Harbor Laboratory Press 2001); TOC.
Sauaia et al., "Early Predictors of Postinjury Multiple Organ Failure," Arch. Surgery 129(1):39-45 (1994).
Selberg et al., "Discrimination of Sepsis and Systematic Inflammatory Response Syndrome by Determination of Circulating Plasma Concentrations of Procalcitonin, Protein Complement 3a, and Interieukin-6," Crit Care Med. 28(8):2793-2798 (2000).
Shoemaker et al., "Recent developments in DNA microarrays," Curr Opin Microbial. 5:334-337 (2002).
Slotman et al., "Multivariate Regression Modeling for the Prediction of Inflammation, Systemic Pressure, and End-organ Function in Severe Sepsis," Shock 8(3):225-231 (1997).
Slotman, "Prospectively Validated Prediction of Physiologic Variables and Organ Failure in Septic Patents: The Systemic Mediator Associated Response Test (SMART)," Crit Care Med. 30 (5):1035-1045 (2002).

(56) References Cited

OTHER PUBLICATIONS

Slotman, "Prospectively validated predictions of shock and organ failure in individual septic surgical patients: the Systemic Mediator Associated Response Test," Crit Care 2000 4(5):319-326 (2000).
Smith et al., 2004, "Impact of immunomodulatory oligodeoxynucleotides on cytokine production in the lipopolvsaccharide-stimulated human whole blood model," Surgery 136(2):464-472.
Spittler et al., "Relationship Between Interleukin-6 plasma Concentration in Patients with Sepsis, Monocyte Phenotype, Monocyte Phagocytic Properties, and Cytokine Production," Clin. Infect Dis., 31(6):1338-1342 (2000).
Stordeur et al., "Cytokine.mRNA quantification by real-time PCR," J Immunol Methods 259:55-64 (2002).
Suzuki et al., 2000, "Comprehensive gene expression profile ofLPS-stimulated human monocytes by SAGE," Blood; 96(7):2584-2591.
Takala et al., "Systemic inflammatory response syndrome without systemic inflammation in acutely ill patients admitted to hospital in a medical emergency," Clin Sci. 96: 287-295 (1999).
Takala et al., "Markers of inflammation in sepsis," Annuls Med. (2002) 34(7-08):614-23.
Tan et al., "The gene expression fingerprint of human heart failure," Proc. Nat'l Acad Sci USA 99:11387-92 (2002).
Tang et al., "Accuracy of procalcitonin for sepsis diagnosis in critically ill patients: Systematic review and meta-analysis", Lancet Infect Dis. (2007) 7(3):210-217.
Taniguchi et al., "Change in the Ratio of Interleukin-6 to Interleukin-10 Predicts a Poor Outcome in Patients with Systemic Inflammatory Response Syndrome," Crit Care Med. 27(7):1262-1264 (1999).
Tárnok et al., "Cytometric bead array to measure six cytokines in twenty-five microliters of serum," Clin. Chem. 49(6):1000-1002 (2003).
Thisted R.A., "What is a P-value?" May 1998, available from http://www.stat.uchicago.edu/-thisted/ printed pp. 1-6.
Titus, "Latest assay opens another sepsis frontier," College of American Pathologists, CAP Today, at http://www.cap.org/apps/docs/cap_today/feature_stories/sepsis.html (posted May 2003); 5 pages.
Uettwiller-Geiger, "Clinical Applications of Procalcitonin (PCT)", J Clin Ligand Assay (2007) 30:20-28.
Van Den Berk et al., "Low HLA-DR Expression on Monocytes as a Prognostic Marker for Bacterial Sepsis after Liver Transplantation," Transplantation 63(12):1846-1848 (1997).
Van Leeuwen et al., "Lipoprotein metabolism in patients with severe sepsis," Crit. Care Med. 31(5):1359-1366 (2003).
Venables et al., "Modern Applied Statistics with S-Plus," (4th Ed., Springer 2002); TOC, 7 pages.
Vincent et al., "The Sepsis Text," (Carlet et al. Eds., Kluwer Academic Publishers 2002); TOC, 4 pages.
Vockley et al., "Cloning and Characterization of Human Type II Arginase Gene," Genomics, 38(2):118-123 (1996).
Von Landenberg et al., "New approaches in the diagnosis of sepsis," Isr Med Assoc J. 3: 439-442 (2001).
Wagner et al., "Daily Prognostic Estimates for Critically Ill Adults in Intensive Care Units: Results from a Prospective, Multicenter, Inception Cohort Analysis,"• Crit Care Med. 22(9): 1359-1372 (1994).
Wagner et al., "Interpretation of static time-of-flight secondary ion mass spectra of adsorbed protein films by multivariate pattern recognition," Anal Chem. 74: 1824-35 (2002).
Wang et al., "Lipid Unites Disparate Syndromes of Sepsis", Nature Medicine, 10(2): 124-125 (2004).
Wakefield et al., "Changes in Major Histocompatibility Complex Class II Expression in Monocytes and T cells of Patients Developing Infection after Surgery,"• Brit J Surgery 80(2):205-209 (1993).
Wakefield et al., "Polymorphonuclear Leukocyte Activation. An Early Marker of the Postsurgical Sepsis Response," Arch Surg. 128:390-395 (1993).
Wakefield et al., "Surgery and the Release of a Neutrophil FcGamma Receptor," Am J Surg. 170:277-284 (1995).
Wang et al., "Co-Induction of Arginase and Nitric Oxide Synthase in Murine Macrophages Activated by Lipopolysaccharide," Biochem Biophys Res Comm. 210(3)1009-1016 (1995).
Wang et al., 1998, "Tissue coexpression ofLBP and CD14 mRNA in a mouse model of sepsis," J. Surg. Res. 76(1):67-73.
Weglöhner et al., "Isolation and characterization of serum procalcitonin from patients with sepsis," Peptides 22:2099-2103 (2001).
Wei et al., "Desorption-ionization mass spectrometry on porous silicon," Nature 399:243-246 (1999).
Weinstein et al., "The clinical significance of positive blood cultures in the 1990s: a prospective comprehensive evaluation of the microbiology, epidemiology, and outcome of bacteremia and fungemia in adults," Clin Infect Diseases. 24:584-602 (1997).
Weirich et al., "Neutrophil CD11b Expression as a Diagnostic Marker for Early-Onset Neonatal Infection," J Pediat. 132 (SS.3, 1 ):445-451 (1998).
Weiss et al., "Filgrastim (RHG-CSF) Related Modulation of the Inflammatory Response in Patients at Risk of Sepsis or with Sepsis," Cytokine, 8(3):260-265 (1996).
Wert et al., 2000, "Increased metalloproteinase activity, oxidant production, and emphysema in surfactant protein D gene-inactivated mice," Proc. Natl. Acad. Sci. USA 97(11):5972-5977.
Wiegand et al., 1999, "Gene Expression Pattern in Human Monocytes as a Surrogate Marker for Systemic Inflammatory Response Syndrome (SIRS)," Mol Med; 5(3):192-202.
Yan et al., "Therapeutic Effects of Lysophosphatidylcholine in Experimental Sepsis", Nature Medicine, 10(2): 161-167 (2004).
Yang et al., "Tissue prostanoids as biomarkers for chemoprevention of colorectal neoplasia: correlation between prostanoid synthesis and clinical response in familial adenormatous polyposis", Prostagl & other Lipid Mediat. (2000) 60:83-96.
Yao et al., "Changes in Toll-like Receptor 2 and 4 Gene Expression in Vital Organs in Septic Rats and Their Regulation Mechanisms", Chin. Crit. Care Med. (2003) 15(11):646-650.
Yassen et al., "Matrix metalloproteinase-9 concentrations in critically ill patients", Anaesthesia, (2001) 56(8):729-732.
Zhang et al., 2001, "Recursive partitioning for tumor classification with gene expression microarray data," Proc Natl Acad Sci U S A; 98( 12):6730-6735.
Zhao et al., "Human endothelial cell response to gram-negative lipopolysaccharide assessed with cDNA microarrays," Am J Physiol Cell Physiol. 281(5):C1587-1595 (2001).
Zhu et al., 1997, "Effects of prolactin and metoclopramide on macrophage cytokine gene expression in late sepsis," Cytokine 9(6):437-446.
Zou, et al.,"Application of cDNA microarrays to generate a molecular taxonomy capable of distinguishing between colon cancer and normal colon," Oncogene 21:4855-4862 (2002).
Zweigner et al., "High concentrations of lipopolysaccharide-binding protein in serum of patients with severe sepsis or septic shock inhibit the lipopolysaccharide response in human monocytes", Blood, (2001) 98(13):3800-3808.
European Extended Search Report dated Dec. 3, 2008 for EP Application No. 06825270.9, filed Sep. 27, 2006.
International Search Report dated Nov. 4, 2009 for Application No. PCT/US2009/002065.
International Preliminary Report on Patentability dated Oct. 5, 2010 for Application No. PCT/US2009/002065.
International Search Report dated Jul. 25, 2007 for Application No. PCT/US2006/038177.
International Preliminary Report on Patentability and Written Opinion dated Apr. 1, 2008 for Application No. PCT/US2006/038177.
B.R.A.H.M.S. GmbH; PTAB Petition for Post-Grant Review dated Apr. 27, 2016 of U.S. Pat. No. 9,091,698, issued Jul. 28, 2015—PGR2016-00018; 84 pages.
B.R.A.H.M.S. GmbH; Exhibit 1002—Declaration of Prof. Dr. med. Philipp Schuetz, MPH signed Feb. 23, 2016; 106 pages.
Becton, Dickinson & Co.; PTAB Preliminary Response dated Aug. 3, 2016—PGR2016—00018; 91 pages.

(56) References Cited

OTHER PUBLICATIONS

PTAB Decision Institution of Post Grant Review dated Nov. 2, 2016—PGR2016-00018; 33 pages.
Akaike, H., "A new look at the statistical model identification," IEEE Transactions on Automatic Control (1974) 19(6): 716-723.
Aoyama N., "Characteristics and problems of instructive reaction system H2O2—POD Series", Rinsho Kensa/Journal of Medical Technology (1997) 41: 1014-1019.
Butler, J. E., "The amplified ELISA: Principles of and applications for the comparative quantitation of class and subclass antibodies and the distribution of antibodies and antigens in biochemical separates", Meth Enzymol. (1981) 73: 482-523.
Chen et al., Study of tetra-substituted amino aluminum phthalocyanine as a new red-region substrate for the fluorometric determination of peroxidase and hydrogen peroxide,Analytica Chimica Acta (2001) 434(1): 51-58.
Dudoit et al., "Comparison of discrimination methods for the classification of tumors using gene expression data", JASA (2002) 97: 77-87.
Ferreira et al., "Serial Evaluation of the SOFA score to predict outcome in critically ill patients", JAMA (2002) 286: 1754-1758.
Joles et. al. "Endothelial function in proteinuric renal disease", Kidney International (1999) 56(Suppl. 71): S57-S61.
Kiba et al., "Flow-through Micro Sensor Using Immobilized Peroxidase with Chemiluminometric FIA System for Determinning Hydrogen Peroxide", Analytical Science (2003) 19(6): 823-827.
Kishimoto et al., "An Enzymatic Assay for Lysophosphatidylcholine concentration in human serum and plasma", Clin Biochem. (2002) 35(5):411-416.
Le Gall et al., "A simplified acute physiology score for ICU patients", Crit Care Med. (1984) 12(11): 975-977.
Le Gall et al., "A new Simplified Acute Physiology Score (SAPS II) based on a European/North American Multicenter Study", JAMA (1993) 270(24): 2957-2963.
Le Gall et al., "The Logistic Organ Dysfunction system. A new way to assess organ dysfunction in the intensive care unit. ICU Scrogin Group"; JAMA (1996) 276(10): 802-810.
Marshall et al., "Multiple organ dysfunction score: a reliable descriptor of a complex clinical outcome", Crit. Care Med (1995) 23(10): 1638-1652.
Misaki H., "Biochemistry. Principle of supersensitive measuring method by enzyme cycling method", Kensa to gijutsu/Modern Medical Laboratory (1999) 27(8): 973-980.
Morgenthaler et al., "Detection of procalcitonin (PCT) in healthy controls and patients with local infection by a sensitive ILMA", Clin Lab. (2002) 48(5-6): 263-270.
Paleologos et al. "Spectrofluorometric Determination of Vanadium Based on the Formation of a Ternary Complex between Vanadium, Peroxides, and 2-alpha-pyndylthioquinaldinamide. Application to the determination of Hydrogen Peroxide and Peroxy Acids", Anal Chem. (2002) 74(1): 100-106.
Pappas et al., "Determination of hydrogen peroxide by using a flow injection system with immobilized peroxidase and long pathlenght capillary spectrophotometry", Analytica Chimica Acta (2002) 455(2): 305-313.
Schwarz G., "Estimating the dimension of a model," Annals of Statistics (1978) 6(2): 461-464.
Voller A., 1978, "The Enzyme Linked Immunosorbent Assay (ELISA)(theory, technique and applications)", Ric Clin Lab. (1978) 8(4): 289-298.
Voller et al., "Enzyme immunoassays with special reference to ELISA Techniques", J Clin Pathol. (1978) 31: 507-520.
Zhang et al., "Optimal Conditions and sample storage for the determination of H2O2 in marine waters by the scopoletin-horseradish peroxidase fluorometric method", Talanta (1999) 48(5):1031-1038.
PTAB Joint Motion to Terminate/Request to File Settlement Agreement dated Mar. 8, 2017—PGR2016-00018, 5 pages.
PTAG Order Termination of the Proceeding dated Mar. 17, 2017—PGR2016-00018; 4 pages.

\* cited by examiner

ADVANCED DETECTION OF SEPSIS

1. CROSS REFERENCE TO RELATED APPLICATIONS

This application is a divisional of U.S. application Ser. No. 14/742,735, filed Jun. 18, 2015 now U.S. Pat. No. 9,708,661, which is a continuation of U.S. application Ser. No. 14/203,367, filed Mar. 10, 2014, now U.S. Pat. No. 9,091,698, which is a continuation of U.S. application Ser. No. 12/935,727, filed Jan. 26, 2011, now U.S. Pat. No. 8,669,113, which is a national stage of International Application No. PCT/US2009/002065, filed Apr. 2, 2009, which in turn claims benefit of U.S. Provisional Application No. 61/123,071, filed Apr. 3, 2008. The contents of each of the above-cited applications are hereby incorporated by reference herein in their entireties.

2. FIELD OF THE INVENTION

The present invention relates to methods, monitors and systems, useful, for example, for advanced detection of sepsis in a subject.

3. BACKGROUND OF THE INVENTION

Early detection of a disease condition typically allows for a more effective therapeutic treatment with a correspondingly more favorable clinical outcome. In many cases, however, early detection of disease symptoms is problematic due to the complexity of the disease; hence, a disease may become relatively advanced before diagnosis is possible. Systemic inflammatory conditions, such as sepsis, severe sepsis, septic shock, multiple organ dysfunction, represent one such class of diseases. These conditions, particularly sepsis, typically, but not always, result from an interaction between a pathogenic microorganism and the host's defense system that triggers an excessive and dysregulated inflammatory response in the host. The complexity of the host's response during the septic response has complicated efforts towards understanding disease pathogenesis (reviewed in Healy, 2002, *Ann. Pharmacother.* 36:648-54). Early and reliable diagnosis is imperative, however, because of the remarkably rapid progression of sepsis into a life-threatening condition.

Sepsis follows a well-described time course, progressing from systemic inflammatory response syndrome (SIRS)-negative to SIRS-positive to sepsis, which may then progress to severe sepsis, septic shock, multiple organ dysfunction (MOD), and ultimately death. Sepsis also may arise in an infected individual when the individual subsequently develops SIRS. "SIRS" is commonly defined as the presence of two or more of the following parameters: body temperature greater than 38° C. or less than 36° C.; heart rate greater than 90 beats per minute; respiratory rate greater than 20 breaths per minute; $P_{CO_2}$ less than 32 mm Hg; and a white blood cell count either less than $4.0 \times 10^9$ cells/L or greater than $12.0 \times 10^9$ cells/L, or having greater than 10% immature band forms. "Sepsis" is commonly defined as SIRS with a confirmed infectious process. "Severe sepsis" is associated with MOD, hypotension, disseminated intravascular coagulation (DIC) or hypoperfusion abnormalities, including lactic acidosis, oliguria, and changes in mental status. "Septic shock" is commonly defined as sepsis-induced hypotension that is resistant to fluid resuscitation with the additional presence of hypoperfusion abnormalities.

Documenting the presence of the pathogenic microorganisms that are clinically significant to sepsis has proven difficult. Causative microorganisms typically are detected by culturing a subject's blood, sputum, urine, wound secretion, in-dwelling line catheter surfaces, etc. Causative microorganisms, however, may reside only in certain body microenvironments such that the particular material that is cultured may not contain the contaminating microorganisms. Detection may be complicated further by low numbers of microorganisms at the site of infection. Low numbers of pathogens in blood present a particular problem for diagnosing sepsis by culturing blood. In one study, for example, positive culture results were obtained in only 17% of subjects presenting clinical manifestations of sepsis (Rangel-Frausto et al., 1995, *JAMA* 273:117-123). Diagnosis can be further complicated by contamination of samples by non-pathogenic microorganisms. For example, only 12.4% of detected microorganisms were clinically significant in a study of 707 subjects with septicemia (Weinstein et al., 1997, *Clinical Infectious Diseases* 24:584-602).

The important of early diagnosis of sepsis is reflected by the high morbidity and mortality associated with the disease. Sepsis currently is the tenth leading cause of death in the United States and is especially prevalent among hospitalized subjects in non-coronary intensive care units (ICUs), where it is the most common cause of death. The overall rate of mortality is as high as 35%, with an estimated 750,000 cases per year occurring in the United States alone. The annual cost to treat sepsis in the United States alone is on the order of billions of dollars.

Most existing sepsis scoring systems or predictive models predict only the risk of late-stage complications, including death, in subjects who already are considered septic and do not predict the development of sepsis itself. Often, the diagnosis of sepsis is based on clinical suspicion with an empirical score system such as APACHE II (Knaus et al., 1985, *Crit. Care Med.* 13:818-829), followed by blood culture. It can take 48 hours or longer to confirm any systemic infections. By then, it is often too late to save some subjects. If detection of sepsis can be made early, prior to manifestation of overt clinical symptoms currently viewed as indicative of a clinically significant infection, treatment can be made available to prevent conversion of a SIRS-positive state into sepsis, or to slow the conversion of sepsis into severe sepsis or septic shock.

A need, therefore, exists for methods of the advanced detection of sepsis using techniques that have satisfactory specificity and sensitivity, sufficiently early to allow effective intervention and prevention.

4. SUMMARY OF THE INVENTION

The present invention is based, in part, on the discovery that the measurement of lysophosphatidylcholine in a sample from a subject can be used for rapid, sensitive and accurate advanced detection of sepsis in a subject. In aspects of the invention, lysophosphatidylcholine in a sample from a subject, combined with one or more clinical markers and/or one or more biomarkers of the subject, is used to detect sepsis in the subject. The methods, monitors and systems of the invention can be used for the advanced detection of any systemic inflammatory condition known to those of skill in the art, including SIRS, sepsis, severe sepsis, septic shock and MOD.

In one aspect of the invention, a method for the advanced detection of a systemic inflammatory condition in a subject comprises the steps of measuring lysophosphatidylcholine in fluid or tissue of the subject, and measuring one or more clinical markers of the subject, to detect the systemic inflammatory condition in the subject. In certain embodiments, the method comprises the steps of measuring at a plurality of time points an amount of lysophosphatidylcholine in fluid or tissue of the subject, and measuring at a plurality of time points one or more clinical markers of the subject. In certain embodiments, the method is for the advanced detection of sepsis. In certain embodiments, the subject is SIRS-negative. In certain embodiments, the subject is SIRS-positive. In certain embodiments, the subject is SIRS-positive and sepsis-negative. In certain embodiments, the subject is sepsis-positive.

In certain embodiments, one clinical marker is measured.

In certain embodiments, temperature is measured.

In particular embodiments, respiratory rate is measured.

In certain embodiments, two or more clinical markers are measured.

In particular embodiments, respiratory rate and temperature are measured.

In certain embodiments, the lysophosphatidylcholine is 1-O-acyl-2-lyso-sn-glycero-3-phosphocholine. The acyl group can be any acyl group known to those of skill in the art. In certain embodiments, the acyl group is $C_{14}$-$C_{22}$ acyl. In further embodiments, the acyl group is $C_{16}$-$C_{18}$ acyl. In particular embodiments, the acyl group is $C_{16}$ acyl. In a preferred embodiment, the acyl group is palmitoyl. In further particular embodiments, the acyl group is $C_{18}$ acyl. In a preferred embodiment, the acyl group is stearoyl. The lysophosphatididylcholine can be in any form from the subject, for instance any salt or solvate that can be identified by those of skill in the art.

In a certain aspect, the present invention is based, in part, on the discovery that lysophosphatidylcholine is useful for rapid, sensitive and accurate advanced detection of a systemic inflammatory condition in a subject. As shown in the examples below, the methods, monitors and systems of the invention can be used for the advanced detection of sepsis in a subject with accuracy up to 58% or more. In particular embodiments, the advanced detection is at least 12 hours prior to the onset of sepsis.

In a certain aspect, the amount of lysophosphatidylcholine in a sample from a subject can be used for the advanced detection of sepsis in the subject. The evaluation can proceed according to any technique for evaluating amount of lysophosphatidylcholine known to those of skill in the art. Exemplary techniques are described herein. However, the present invention provides methods based on any technique of evaluating lysophosphatidylcholine apparent to those of skill in the art.

In certain embodiments, measurements of the amount of lysophosphatidylcholine in the subject are made at a single time point ("snapshot"). In certain embodiments, measurements of the amount of lysophosphatidylcholine in the subject are made at a plurality of time points. In certain embodiments, measurement of the amount of lysophosphatidylcholine is made at regular time intervals. The time intervals can be, for instance, 3 hours, 4 hours, 6 hours, 12 hours, 24 hours or other intervals according to the judgment of the practitioner in the art. In these embodiments, the relative amounts of lysophosphatidylcholine are evaluated for the advanced detection of sepsis in a subject by a practitioner of skill in the art. In particular embodiments, one amount of lysophophostidylcholine measured is 0, 12, 24, 36 or 48 hours prior to the manifestation of overt clinical symptoms currently viewed as indicative of a clinically significant infection. In particular embodiments, increasing amounts of lysophosphatidylcholine indicate decreased likelihood of onset of sepsis, and decreasing amounts of lysophosphatidylcholine detect sepsis or indicate increased likelihood of onset of sepsis.

In other embodiments, the evaluation is based on a comparison of the amount of lysophosphatidylcholine to a reference amount of lysophosphatidylcholine. The reference amount can be, for instance, the amount of lysophosphatidylcholine in a reference individual that manifests, or will manifest within a defined period of time, one or more symptoms of the known systemic inflammatory condition. The amount can be, for instance, an absolute value or an absolute value with a margin of error or a range of values, as determined by those of skill in the art. In certain embodiments, the reference individual exhibits, or will exhibit, symptoms of SIRS, sepsis, severe sepsis, septic shock, MOD, or no symptoms of a systemic inflammatory condition. In particular embodiments, low amounts of lysophosphatidylcholine (e.g. relative to a reference amount) detect sepsis or indicate increased likelihood of onset of sepsis, and high amounts of lysophosphatidylcholine (e.g. relative to a reference amount) indicate that sepsis is not detected or that a reduced likelihood of onset of sepsis exists.

Advantageously, the reference amount need not be determined by one carrying out a method of the invention. Instead, the reference amount of lysophosphatidylcholine can be identified by consulting data available to those of skill in the art. Such data can be obtained from any source available to those of skill in the art. In certain embodiments, sources can be developed with reference amounts of lysophosphatidylcholine collected by those of skill in the art according to methods described herein.

In certain embodiments, the reference amount is from a reference individual presenting symptoms of the systemic inflammatory condition. The reference individual can present symptoms of SIRS, sepsis, severe sepsis, septic shock, MOD, or no symptoms of a systemic inflammatory condition. In certain embodiments, the reference amount can be evaluated at a time prior to or after presentation of symptoms. For instance, in an advantageous embodiment, a reference amount can be the amount measured in a SIRS-positive individual 0, 12, 24, 36 or 48 hours prior to the manifestation of overt clinical symptoms currently viewed as indicative of a clinically significant infection. Measurement of such reference amounts is within the skill of those in the art.

In further embodiments, reference amounts are from a plurality of individuals presenting symptoms of one or more systemic inflammatory conditions. The reference amounts can be calculated according to any suitable statistical method known to those of skill in the art. For instance, the reference amounts can be based on the statistical mean of reference amounts from reference individuals presenting a systemic inflammatory condition. In advantageous embodiments, comparison is made to a value or range of values for the amount of lysophosphatidylcholine. The value or range of values can be obtained as described herein and made available to a practitioner of the methods of the invention. In particular embodiments, low amounts of lysophosphatidylcholine (e.g. relative to a reference amount) detect sepsis or indicate increased likelihood of onset of sepsis, and high amounts of lysophosphatidylcholine (e.g. relative to a reference amount) indicate that sepsis is not detected or that a reduced likelihood of onset of sepsis exists.

The comparison can be according to any technique for comparing amounts of lysophosphatidylcholine known to those of skill in the art. In one embodiment, the advanced detection of sepsis is based on the difference between the amount of lysophosphatidylcholine in the subject and the reference amount. In certain embodiments, the difference between the amount of lysophosphatidylcholine in the subject and the reference amount correlates inversely with detection of sepsis or with an increased likelihood of onset of sepsis. In further embodiments, the reference amount is a threshold—in other words, amounts of lysophosphatidylcholine less than the threshold amount detect sepsis or indicate increased likelihood of onset of sepsis. Such threshold reference amounts can be calculated according to methods described herein.

The amount of lysophosphatidylcholine in the subject can be determined according to any technique known to those of skill in the art without limitation. It is known that lysophospatidylcholine is bound to proteins such as albumin in the circulation (J. Joles et. al. *Kidney International* Vol. 56, Suppl. 71 (1999), pp S57-61). In certain embodiments, one of skill can measure an amount that correlates to the amount of lysophosphatidylcholine in a sample. For instance, in particular embodiments, one of skill can measure free lysophosphatidylcholine, bound lysophosphatidylcholine or free and bound lysophosphatidylcholine in the sample to indicate the amount of total lysophosphatidylcholine in the sample. In other words, in certain embodiments, measurement of free or bound, or both free and bound, lysophosphatidylcholine can correlate to the amount of total lysophosphatidylcholine. In certain embodiments, the technique for evaluating amount of lysophosphatidylcholine is not critical for the invention and need not be carried out by one practicing the methods herein. For instance, in particular embodiments, methods of the invention can comprise the single step of comparing lysophosphatidylcholine amount in a subject to a reference lysophosphatidylcholine amount in order to detect sepsis or indicate likelihood of onset of sepsis without regard to how either amount is measured.

In further embodiments, the amount of lysophosphatidylcholine in the subject is evaluated by a technique described herein followed by comparing to a reference amount of lysophosphatidylcholine in order to detect sepsis or indicate likelihood of onset of sepsis. In certain embodiments, the amount of lysophosphatidylcholine is evaluated by spectrometry, chromatography, immunoassay, electrophoresis, electrochemical method or enzymatic assay as described in detail below.

The amount of lysophosphatidylcholine can be measured in fluids or tissues of the subject as provided herein. Processes for preparing the fluid or tissue, for example, processes for extracting or purifying lysophosphatidylcholine are described herein. Further, techniques for measuring lysophosphatidylcholine are provided herein. In certain embodiments, the fluid or tissue of the subject is blood, plasma, saliva, serum, sputum, urine, cells, cellular extract or tissue biopsy.

In another aspect of the invention, a method for the advanced detection of a systemic inflammatory condition in a subject comprises the steps of measuring at a plurality of time points a compound according to formula (I):

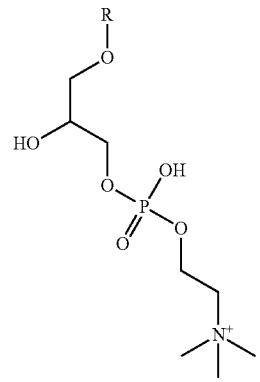

(I)

or a salt or solvate thereof, in fluid or tissue of the subject, and measuring at a plurality of time points one or more clinical markers of the subject to detect the systemic inflammatory condition in the subject. In certain embodiments, the method is for the advanced detection of sepsis.

In certain embodiments, one clinical marker is measured.
In certain embodiments, temperature is measured.
In particular embodiments, respiratory rate is measured.
In certain embodiments, two or more clinical markers are measured.
In particular embodiments, respiratory rate and temperature are measured.
In certain embodiments, the subject is SIRS-negative. In certain embodiments, the subject is SIRS-positive. In certain embodiments, the subject is SIRS-positive and sepsis-negative. In certain embodiments, the subject is sepsis-positive.

In formula (I), R can be any acyl group known to those of skill in the art. In certain embodiments, R is saturated acyl. In further embodiments, R is $C_{10}$-$C_{22}$ acyl. In further embodiments, R is $C_{14}$-$C_{22}$ acyl. In further embodiments, R is $C_{16}$-$C_{20}$ acyl. In further embodiments, R is $C_{16}$-$C_{18}$ acyl. In particular embodiments, R is $C_{16}$ saturated acyl. In particular embodiments, R is $C_{18}$ saturated acyl. In particular embodiments, R is unbranched $C_{16}$-$C_{18}$ acyl. In a preferred embodiment, R is palmitoyl. In a preferred embodiment, R is stearoyl.

Exemplary salts of formula (I) are provided by formula (Ia):

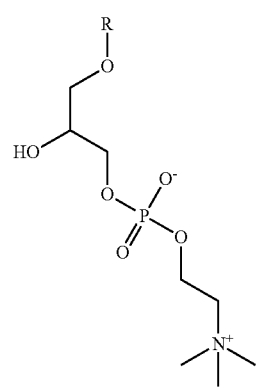

(Ia)

wherein said salt can be coordinated with any physiological organic or inorganic anion, or any physiological organic or inorganic cation, or both, known to those of skill in the art.

Exemplary physiological anions include chloride, bromide, phosphate, acetate, carbonate, bicarbonate and sulfate. Exemplary physiological cations include sodium, potassium, calcium, magnesium and ammonium.

In certain embodiments, the advanced detection is 0, 12, 24, 36 or 48 hours prior to the onset of sepsis.

In certain embodiments, advanced detection may immediately prior to the onset of sepsis, for example, 1 hour, 30 minutes, 15 minutes, or even 1 minute prior to the onset of sepsis.

In certain embodiments, one amount of the compound according to Formula (I) measured is 0, 12, 24, 36 or 48 hours prior to the onset of sepsis.

In certain embodiments, the difference between the amounts measured for the compound according to Formula (I) correlates inversely with detection of sepsis or with an increased likelihood of onset of sepsis.

In certain embodiments of the invention, the method for the advanced detection of sepsis in a subject further comprises measuring at a plurality of time points one or more biomarkers in fluid or tissue of the subject.

In certain embodiments, a difference in the amount of one or more biomarkers measured at a plurality of time points detects sepsis or indicates increased likelihood of onset of sepsis.

In certain embodiments, the amount of one or more biomarkers measured at a plurality of time points correlates inversely with detection of sepsis or with an increased likelihood of onset of sepsis.

In certain embodiments, the amount of one or more biomarkers measured at a plurality of time points correlates directly with detection of sepsis or with an increased likelihood of onset of sepsis.

In certain embodiments, one or more biomarkers are selected from the group consisting of endotoxin, bacterial DNA, protein C, protein S, procalcitonin (PCT), C-reactive protein (CRP), LBP LPS-binding protein, fibrin degrading products, HLA-DR, cell surface proteins CD-14 and CD-64, E-selectin, cortisol, ACTH, surface-bound tumor necrosis factor receptor I (sTNFRI), surface-bound tumor necrosis factor receptor II (sTNF-RII), TNF-α, interleukins IL-6, IL-8 and IL-10, D-dimer, prothrombin, antithrombin III, activated partial thromboplastin, plasminogen activator inhibitor-1, soluble thrombomodulin, thrombin activatable fibrinolysis inhibitor, copeptin, high mobility group box 1 (HMGB1), triggering receptor expressed on myeloid cells 1 (TREM1) and albumin.

In particular embodiments, one or more biomarkers comprise procalcitonin.

In certain embodiments, the amount of the biomarker is measured by spectrometry, chromatography, immunoasasay, electrophores is or enzymatic assay.

The amount of biomarker can be measured in fluids or tissues of the subject as provided herein. Processes for preparing the fluid or tissue, for example, processes for extracting or purifying the biomarker are described herein. Further, techniques for measuring the biomarker are provided herein. In certain embodiments, the fluid or tissue of the subject is blood, plasma, saliva, serum, sputum, urine, cells, cellular extract or tissue biopsy.

In another aspect of the invention, a method for the advanced detection of a systemic inflammatory condition in a subject comprises the steps of measuring at a plurality of time points the amount of procalcitonin in fluid or tissue of the subject, and measuring at a plurality of time points one or more clinical markers of the subject. In certain embodiments, the method is for the advanced detection of sepsis. In certain embodiments, the subject is SIRS-negative. In certain embodiments, the subject is SIRS-positive. In certain embodiments, the subject is SIRS-positive and sepsis-negative. In certain embodiments, the subject is sepsis-positive.

In certain embodiments, the one or more clinical markers are selected from the group consisting of respiratory rate, temperature, heart rate, systolic blood pressure, diastolic blood pressure mean artery pressure, white blood cell count, monocyte count, lymphocyte count, granulocyte count, neutrophil count, immature neutrophil to total neutrophil ratio, platelet count, serum creatinine concentration, urea concentration, lactate concentration, gluose concentration, base excess, $pO_2$ and $HCO_3^-$ concentration.

In certain embodiments, one clinical marker is measured.

In certain embodiments, temperature is measured.

In particular embodiments, respiratory rate is measured.

In certain embodiments, two or more clinical markers are measured.

In particular embodiments, respiratory rate and temperature are measured.

In certain embodiments, the advanced detection is 0, 12, 24, 36 or 48 hours prior to the onset of sepsis.

In certain embodiments, a body temperature greater than 38° C. detects sepsis.

In certain embodiments, a body temperature less than 36° C. detects sepsis.

In certain embodiments, a respiratory rate greater than 20 breaths per minute detects sepsis.

In another aspect, the present invention provides monitors for the advanced detection of a systemic inflammatory condition. In such monitors, measurement of the amount of lysophosphatidylcholine is used to monitor for the systemic inflammatory condition in the subject. In such monitors, changes in the amount of lysophosphatidylcholine are capable of indicating changes in the systemic inflammatory condition. For instance, in certain embodiments, decreasing amounts of lysophosphatidylcholine detect sepsis or indicate increased likelihood of onset of sepsis, and increasing amounts of lysophosphatidylcholine indicate that sepsis is not detected or that a reduced likelihood of onset of sepsis exists.

In some embodiments, amount of lysophosphatidylcholine can indicate conversion from one systemic inflammatory condition to another or no systemic inflammatory condition. In a particularly advantageous embodiment, amount of lysophosphatidylcholine can indicate conversion from the SIRS-positive state to septic state.

In certain embodiments, provided herein are modules that detect lysophosphatidylcholine.

In certain embodiments, the invention provides monitors for the advanced detection of sepsis in a subject comprising: (a) a sensor module capable of measuring one or more clinical markers of the subject, and (b) a chemistry module capable of measuring an amount of lysophosphatidylcholine in fluid or tissues of the subject. In certain embodiments, the sensor module is capable of measuring at a plurality of time points one or more clinical markers of the subject. In certain embodiments, the chemistry module is capable of measuring at a plurality of time points an amount of lysophosphatidylcholine in fluid or tissues of the subject. In particularly advantageous embodiments, the monitor is capable of continuous measuring. In certain embodiments, the monitor is capable of measuring two or more markers. In particular embodiments, the monitor is capable of measuring respiratory rate and temperature.

In certain embodiments, the invention provides monitors for the advanced detection of sepsis in a subject comprising:

(a) a sensor module that measures one or more clinical markers of the subject, and (b) a chemistry module that measures an amount of lysophosphatidylcholine in fluid or tissues of the subject. In certain embodiments, the sensor module measures at a plurality of time points one or more clinical markers of the subject. In certain embodiments, the chemistry module measures at a plurality of time points an amount of lysophosphatidylcholine in fluid or tissues of the subject. In particularly advantageous embodiments, the monitor continuously measures. In certain embodiments, the monitor measures two or more markers. In particular embodiments, the monitor measures respiratory rate and temperature.

In certain embodiments, the chemistry module is capable of contacting a sample from the fluid or tissue of the subject with one or more reagents capable of generating a fluorescent product indicative of amount of lysophosphatidylcholine in the sample. In certain embodiments, the chemistry module is capable of detecting the presence of lysophosphatidylcholine or of detecting the amount of lysophosphatidylcholine, or both, in the sample. In particular embodiments, the chemistry module is capable of contacting the sample with a fluorogenic substrate of one or more of the reagents. This fluorogenic substrate can be converted to the fluorescent product indicating amount of lysophosphatidylcholine. In advantageous embodiments, the reagents comprise peroxidase, choline oxidase, glycerophosphatidylcholine diesterase and lysophospholipase. An exemplary fluorogenic substrate is 10-acetyl-3,7-dihydroxyphenoxazine, a compound that can be converted to the fluorescent product 7-hydroxy-3H-phenoxazin-3-one.

In certain embodiments, the sample from the fluid or tissue of the subject in the chemistry module is contacted with one or more reagents capable of generating a fluorescent product indicative of amount of lysophosphatidylcholine in the sample. In certain embodiments, the chemistry module detects the presence of lysophosphatidylcholine or of detecting the amount of lysophosphatidylcholine, or both, in the sample. In particular embodiments, the chemistry module contacts the sample with a fluorogenic substrate of one or more of the reagents. This fluorogenic substrate can be converted to the fluorescent product indicating amount of lysophosphatidylcholine. In advantageous embodiments, the reagents comprise peroxidase, choline oxidase, glycerophosphatidylcholine diesterase and lysophospholipase. An exemplary fluorogenic substrate is 10-acetyl-3,7-dihydroxyphenoxazine, a compound that can be converted to the fluorescent product 7-hydroxy-3H-phenoxazin-3-one.

In certain embodiments, the invention provides monitors for the advanced detection of sepsis in a subject comprising: (a) a first sensor module capable of measuring the subject's temperature, (b) a second sensor module capable of measuring the subject's respiratory rate, and (c) a chemistry module capable of measuring an amount of lysophosphatidylcholine in fluid or tissues of the subject. In certain embodiments, the first and second sensor modules are capable of measuring at a plurality of time points the subject's temperature and the subject's respiratory rate. In certain embodiments, the chemistry module is capable of measuring at a plurality of time points an amount of lysophosphatidylcholine in fluid or tissues of the subject. In particularly advantageous embodiments, the monitor is capable of continuous measuring.

In certain embodiments, the invention provides monitors for the advanced detection of sepsis in a subject comprising: (a) a first sensor module that measures the subject's temperature, (b) a second sensor module that measures the subject's respiratory rate, and (c) a chemistry module that measures an amount of lysophosphatidylcholine in fluid or tissues of the subject. In certain embodiments, the first and second sensor modules measure at a plurality of time points the subject's temperature and the subject's respiratory rate. In certain embodiments, the chemistry module measures at a plurality of time points an amount of lysophosphatidylcholine in fluid or tissues of the subject. In particularly advantageous embodiments, the measurement at a plurality of time points is continuous.

In certain embodiments, the first sensor module is capable of connecting to a temperature probe in the subject. In particular embodiments, the temperature probe is capable of being applied externally to the subject's skin. In particular embodiments, the temperature probe is capable of being applied internally to the subject. In particular embodiments, the temperature probe is capable of being applied to the subject's esophagus or rectum.

In certain embodiments, the first sensor module is connected to a temperature probe in the subject. In particular embodiments, the temperature probe is applied externally to the subject's skin. In particular embodiments, the temperature probe is applied internally to the subject. In particular embodiments, the temperature probe is applied to the subject's esophagus or rectum.

In certain embodiments, the second sensor module is capable of connecting to a motion sensor. In particular embodiments, the motion sensor is a flow meter. In particular embodiments, the flow meter is in a respirator.

In certain embodiments, the second sensor module is connected to a motion sensor. In particular embodiments, the motion sensor is a flow meter. In particular embodiments, the flow meter is in a respirator.

In certain embodiments, the individual sensor modules and chemistry modules of the monitor operate separately of one another.

In certain embodiments, the invention provides for a stand-alone monitor capable of measuring lysophosphatidylcholine in fluid or tissues of the subject.

In certain embodiments, the invention provides for a stand-alone monitor capable of measuring at a plurality of time points an amount of lysophosphatidylcholine in fluid or tissues of the subject.

In certain embodiments, the invention provides for a stand-alone monitor that measures lysophosphatidylcholine in fluid or tissues of the subject.

In certain embodiments, the invention provides for a stand-alone monitor that measures at a plurality of time points an amount of lysophosphatidylcholine in fluid or tissues of the subject.

In another aspect, the present invention provides systems for the advanced detection of a systemic inflammatory condition. Such systems comprise a computational device capable of combining the clinical marker and lysophosphatidylcholine measurements obtained from the monitors of the invention into a result indicative of status of the subject. In certain embodiments, a value less than a reference threshold value, specified for a particular systemic inflammatory condition, indicates that the condition is not detected or that a decreased likelihood of onset of the condition exists, and a value greater than the reference threshold value detects the condition or indicates increased likelihood of onset of the condition. For instance, in certain embodiments, a value less than a reference threshold value for sepsis indicates that sepsis is not detected or that a decreased likelihood of onset of sepsis exists, and a value greater than the reference threshold value for sepsis detects sepsis or indicates increased likelihood of onset of sepsis. In other embodiments, a "no" value indicates that sepsis is not detected or that a reduced likelihood of onset of sepsis exists, and a "yes" value indicates that sepsis is detected or an increased likelihood of onset of sepsis.

In certain aspects, the invention provides systems for the advanced detection of sepsis in a subject comprising: (a) one or more monitors of the invention, (b) a computational device capable of combining the clinical marker and lysophosphatidylcholine measurements obtained from the monitors into a result, comprising: (i) a device capable of receiving the clinical marker and lysophosphatidylcholine measurements from the one or more monitors; (ii) a microprocessor with an algorithm capable of combining the measurements into a result; (iii) a device capable of transmitting the result to a module capable of storing, displaying and/or transmitting, and (c) a module capable of storing, displaying and/or transmitting the result.

In certain aspects, the invention provides systems for the advanced detection of sepsis in a subject comprising: (a) one or more monitors of the invention, (b) a computational device that combines the clinical marker and lysophosphatidylcholine measurements obtained from the monitors into a result, comprising: (i) a device that receives the clinical marker and lysophosphatidylcholine measurements from the one or more monitors; (ii) a microprocessor with an algorithm that combines the measurements into a result; (iii) a device that transmits the result to a module that stores, displays and/or transmits, and (c) a module that stores, displays and/or transmits the result.

In certain aspects, the invention provides systems for the advanced detection of sepsis in a subject comprising: (a) one or more monitors of the invention, (b) a computational device capable of combining the temperature, respiratory rate, and lysophosphatidylcholine measurements obtained from the monitors into a result, comprising: (i) a device capable of receiving temperature, respiratory rate, and lysophosphatidylcholine measurements from the one or more monitors; (ii) a microprocessor with an algorithm capable of combining the measurements into a result; (iii) a device capable of transmitting the result to a module capable of storing, displaying and/or transmitting, and (c) a module capable of storing, displaying and/or transmitting the result.

In certain aspects, the invention provides systems for the advanced detection of sepsis in a subject comprising: (a) one or more monitors of the invention, (b) a computational device that combines the temperature, respiratory rate, and lysophosphatidylcholine measurements obtained from the monitors into a result, comprising: (i) a device that receives temperature, respiratory rate, and lysophosphatidylcholine measurements from the one or more monitors; (ii) a microprocessor with an algorithm that combines the measurements into a result; (iii) a device that transmits the result to a module that stores, displays and/or transmits, and (c) a module that stores, displays and/or transmits the result.

In certain aspects, the invention provides systems for the advanced detection of sepsis in a subject comprising: (a) a sensor module capable of measuring at a plurality of time points one or more clinical markers of the subject, (b) a chemistry module capable of measuring at a plurality of time points an amount of lysophosphatidylcholine or procalcitonin in fluid or tissue of the subject, (c) a computational device capable of combining the measurements in (a) and the measurements in (b) into a result, comprising: (i) a device capable of receiving the measurements in (a) and the measurements in (b) from the one or more modules; (ii) a microprocessor with an algorithm capable of combining the measurements into a result; and (iii) a device capable of transmitting the result to a module capable of storing, displaying and/or transmitting; and (d) a module capable of storing, displaying or transmitting the result.

In certain aspects, the invention provides systems for the advanced detection of sepsis in a subject comprising: (a) a sensor module that measures at a plurality of time points one or more clinical markers of the subject, (b) a chemistry module that measures at a plurality of time points an amount of lysophosphatidylcholine or procalcitonin in fluid or tissue of the subject, (c) a computational device that combines the measurements in (a) and the measurements in (b) into a result, comprising: (i) a device that receives the measurements in (a) and the measurements in (b) from the one or more modules; (ii) a microprocessor with an algorithm that combines the measurements into a result; and (iii) a device that transmits the result to a module that stores, displays and/or transmits; and (d) a module that stores, displays or transmits the result.

In certain embodiments of the invention, the module capable of storing, displaying and/or transmitting is a display module.

In certain embodiments of the invention, the device in (i) and the microprocessor in (ii) are the same device.

In certain embodiments, the algorithm of the microprocessor is selected from discriminant analysis, quadratic discriminant analysis, logical regression analysis, regression classifiers, neural networks, and combinations thereof.

In certain embodiments, the computational device is further capable of comparing the lysophosphatidylcholine amount to a reference amount indicative of the amounts of lysophosphatidylcholine in fluids or tissues of a plurality of individuals that have, or will have, sepsis.

In certain embodiments, the computational device compares the lysophosphatidylcholine amount to a reference amount indicative of the amounts of lysophosphatidylcholine in fluids or tissues of a plurality of individuals that have, or will have, sepsis.

In particular embodiments, the reference amount is the amount measured in a SIRS-positive individual 0, 12, 24, 36 or 48 hours prior to the onset of sepsis.

In certain embodiments, the result is a number that detects sepsis.

In certain embodiments, the result is a "yes/no" signal, wherein "yes" detects sepsis.

In certain embodiments, the result is displayed on a screen.

In certain embodiments, the result is transmitted to the medical record of the subject.

5. BRIEF DESCRIPTION OF THE FIGURES

FIG. 1 provides an embodiment of the systems of the invention;

6. DETAILED DESCRIPTION OF THE INVENTION

6.1 Definitions

Figure 1:
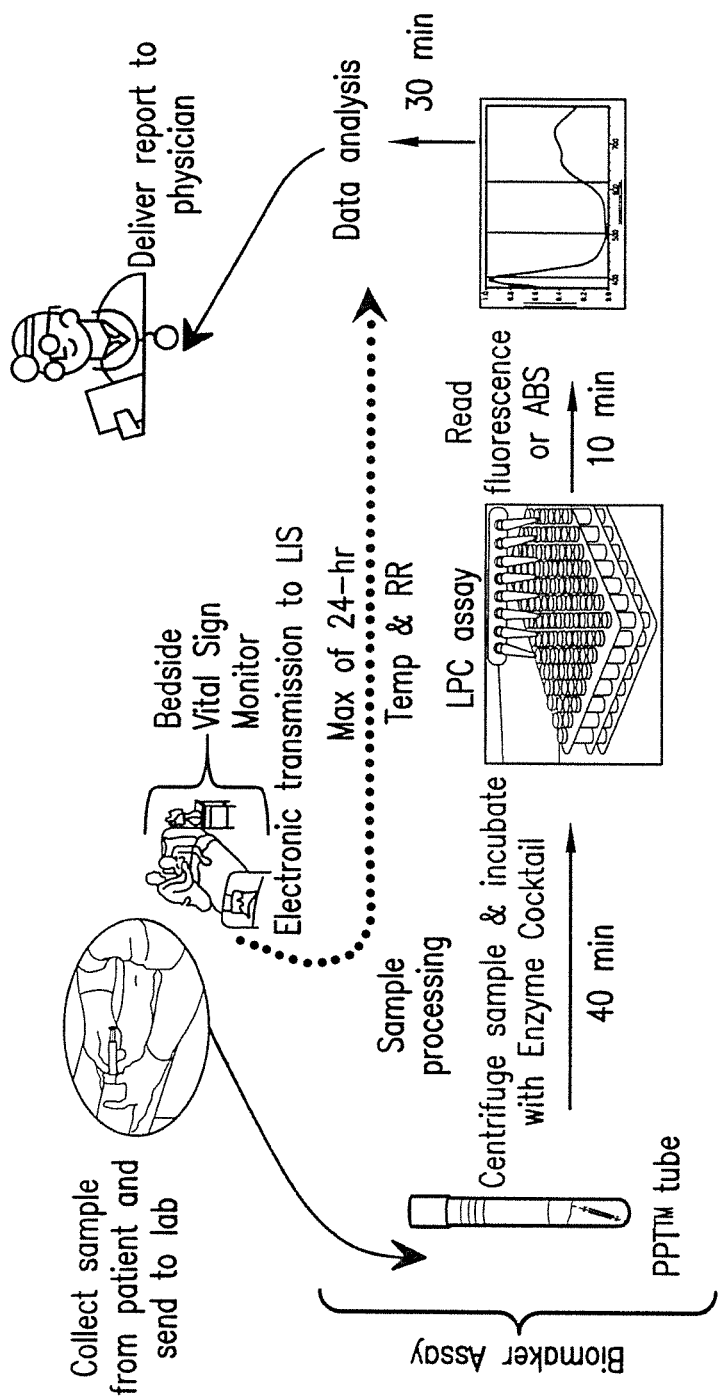

As used herein, the following terms shall have the following meanings:

The term "subject" refers to animals such as mammals, including, but not limited to, primates (e.g., humans), cows, sheep, goats, horses, dogs, cats, rabbits, rats, mice and the like. In preferred embodiments, the subject is human. The term "subject" is interchangeable with a human subject, unless noted otherwise.

"Systemic inflammatory response syndrome," or "SIRS," refers to a clinical response to a variety of severe clinical insults, as manifested by two or more of the following conditions within a 24-hour period:

body temperature greater than 38° C. (100.4° F.) or less than 36° C. (96.8° F.);

heart rate (HR) greater than 90 beats/minute;

respiratory rate (RR) greater than 20 breaths/minute, or $P_{CO_2}$ less than 32 mmHg, or requiring mechanical ventilation; and white blood cell count (WBC) either greater than $12.0 \times 10^9$/L or less than $4.0 \times 10^9$/L or having greater than 10% immature band forms.

These symptoms of SIRS represent a consensus definition of SIRS that can be modified or supplanted by other definitions in the future. The present definition is used to clarify current clinical practice and does not represent a critical aspect of the invention (see, e.g., American College of Chest Physicians/Society of Critical Care Medicine Consensus Conference: Definitions for Sepsis and Organ Failure and Guidelines for the Use of Innovative Therapies in Sepsis, 1992, *Crit. Care. Med.* 20, 864-874, the entire contents of which are herein incorporated by reference).

A subject with SIRS has a clinical presentation that is classified as SIRS, as defined above, but is not clinically deemed to be septic. Methods for determining which subjects are at risk of developing sepsis are well known to those in the art. Such subjects include, for example, those in an intensive care unit (ICU) and those who have otherwise suffered from a physiological trauma, such as a burn, surgery or other insult. A hallmark of SIRS is the creation of a proinflammatory state that can be marked by tachycardia, tachypnea or hyperpnea, hypotension, hypoperfusion, oliguria, leukocytosis or leukopenia, pyrexia or hypothermia and the need for volume infusion. SIRS characteristically does not include a documented source of infection (e.g., bacteremia).

"Sepsis" refers to a systemic host response to infection with SIRS plus a documented infection (e.g., a subsequent laboratory confirmation of a clinically significant infection such as a positive culture for an organism). Thus, sepsis refers to the systemic inflammatory response to a documented infection (see, e.g., American College of Chest Physicians Society of Critical Care Medicine, Chest, 1997, 101:1644-1655, the entire contents of which are herein incorporated by reference). As used herein, "sepsis" includes all stages of sepsis including, but not limited to, the conversion to sepsis, severe sepsis, septic shock and multiple organ dysfunction ("MOD") associated with the end stages of sepsis.

The "onset of sepsis" refers to an early stage of sepsis, e.g., prior to a stage when conventional clinical manifestations are sufficient to support a clinical suspicion of sepsis. Because the methods of the present invention can be used to detect sepsis prior to a time that sepsis would be suspected using conventional techniques, in certain embodiments, the subject's disease status at early sepsis is confirmed retrospectively, when the manifestation of sepsis is more clinically obvious. The exact mechanism by which a subject becomes septic is not a critical aspect of the invention. The methods of the present invention can detect the onset of sepsis independent of the origin of the infectious process.

"Advanced detection of sepsis" refers to detection of sepsis, or likelihood of development of clinical manifestations sufficient to support a clinical suspicion of sepsis, that is, prior to the onset of overt signs indicative of a clinically significant infection, prior to the development of such clinical manifestations. In certain embodiments, advanced detection of sepsis means at least 48 hours prior to the development of such clinical manifestations. In other embodiments, advanced detection of sepsis means at least 36 hours prior to the development of such clinical manifestations. In other embodiments, advanced detection of sepsis means at least 24 hours prior to the development of such clinical manifestations. In other embodiments, advanced detection of sepsis means at least 12 hours prior to the development of such clinical manifestations. In other embodiments, advanced detection of sepsis means at least 6 hours prior to the development of such clinical manifestations. In other embodiments, advanced detection of sepsis means at least 3 hours prior to the development of such clinical manifestations. In other embodiments, advanced detection of sepsis means at least 1 hour prior to the development of such clinical manifestations. In other embodiments, advanced detection of sepsis means just prior to the development of such clinical manifestations determined by an attending physician.

"Severe sepsis" refers to sepsis associated with organ dysfunction, hypoperfusion abnormalities, or sepsis-induced hypotension. Hypoperfusion abnormalities include, but are not limited to, lactic acidosis, oliguria, or an acute alteration in mental status.

"Septic shock" refers to sepsis-induced hypotension that is not responsive to adequate intravenous fluid challenge and with manifestations of peripheral hypoperfusion.

A "clinical marker" refers to a physiological parameter that can be measured in the subject, such as a clinical vital sign. Examples include, but are not limited to respiratory rate, temperature, heart rate, systolic blood pressure, diastolic blood pressure mean artery pressure, white blood cell count, monocyte count, lymphocyte count, granulocyte count, neutrophil count, immature neutrophil to total neutrophil ratio, platelet count, serum creatinine concentration, urea concentration, lactate concentration, glucose concentration, base excess, $pO_2$ and $HCO_3^-$ concentration.

A "converter" or "converter subject" refers to a SIRS-positive subject who progresses to clinical suspicion of sepsis during the period the subject is monitored, typically during an ICU stay.

A "non-converter" or "non-converter subject" refers to a SIRS-positive subject who does not progress to clinical suspicion of sepsis during the period the subject is monitored, typically during an ICU stay.

A "biomarker" is a compound that is present in or derived from a biological sample. "Derived from" as used in this context refers to a compound that, when detected, is indicative of a particular molecule being present in the biological sample. For example, detection of a particular fragment of a compound can be indicative of the presence of the compound itself in the biological sample. A biomarker can, for example, be isolated from the biological sample, directly measured in the biological sample, or detected in or determined to be in the biological sample. A biomarker can, for example, be functional, partially functional, or non-functional.

As used herein, "conventional techniques" in the context of the advanced detection of a systemic inflammatory condition are those techniques that classify a subject based on phenotypic changes without evaluating a biomarker according to the present invention.

As used herein, the tem' "specifically," and analogous terms, in the context of an antibody, refers to peptides, polypeptides, and antibodies or fragments thereof that specifically bind to an antigen or a class of antigens, or fragments thereof, and do not specifically bind to other antigens or other fragments. A peptide or polypeptide that specifically binds to an antigen may bind to other peptides or polypeptides with lower affinity, as determined by standard experimental techniques, for example, by any immunoassay well-known to those skilled in the art. Such immunoassays include, but are not limited to, radioimmunoassays (RIAs) and enzyme-linked immunosorbent assays (ELISAs). Antibodies or fragments that specifically bind to an antigen may be cross-reactive with related antigens. Preferably, antibodies or fragments thereof that specifically bind to an antigen do not cross-react with other antigens. See, e.g., Paul, ed., 2003, Fundamental Immunology, 5th ed., Raven Press, New York at pages 69-105, which is incorporated by reference herein, for a discussion regarding antigen-antibody interactions, specificity and cross-reactivity, and methods for determining all of the above.

As used herein, a "reference population" is a population of subjects that can be used to construct an algorithm for evaluation of a biomarker of subjects at risk for developing a systemic inflammatory condition.

A "reference subject" is a subject that has been diagnosed, or will be diagnosed within a defined period of time, with a systemic inflammatory condition according to standards recognized by those of skill in the art. A reference subject is useful for establishing a reference amount of the biomarker that can be used to evaluate an amount of the biomarker in a test subject for the advanced detection of a systemic inflammatory condition.

As used herein, a "training population" is a set of samples from a population of subjects used to fit an algorithm. In a preferred embodiment, a training population includes samples from subjects that are converters and subjects that are nonconverters.

As used herein, an "algorithm" is a statistical model used to combine lysophosphatidylcholine, clinical and/or biomarker values into a result that detects or is indicative of sepsis. Representative algorithms are described in Section 5.12.

As used herein, "ROC" means a receiver operator characteristic curve that can be used to evaluate algorithm performance.

As used herein, a "functional" is a function whose input is a function or curve, and whose output is a number.

The term "label" refers to a display of written, printed or graphic matter upon the immediate container of an article, for example the written material displayed on a vial containing a pharmaceutically active agent.

The term "labeling" refers to all labels and other written, printed or graphic matter upon any article or any of its containers or wrappers or accompanying such article, for example, a package insert or instructional audios or videos, e.g. videotapes or DVDs, accompanying or associated with a container of a pharmaceutically active agent.

"Acyl" refers to a radical —C(O)R, where R is alkyl.

"Alkyl," by itself or as part of another substituent, means, unless otherwise stated, a straight or branched chain hydrocarbon radical which may be fully saturated, mono- or polyunsaturated, having the number of carbon atoms designated (i.e., $C_1$-$C_{22}$ means one to twenty-two carbons). Examples of saturated hydrocarbon radicals include groups such as methyl, ethyl, n-propyl, isopropyl, n-butyl, t-butyl, isobutyl, sec-butyl, cyclohexyl, (cyclohexyl)methyl, cyclopropylmethyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers.

"Physiologically acceptable salt" refers to a salt of a compound of the invention that is pharmaceutically acceptable and that possesses the desired pharmacological activity of the parent compound. Such salts include: (1) acid addition salts formed with organic or inorganic acids such as hydrochloric, hydrobromic, sulfuric, nitric, phosphoric, acetic, trifluoroacetic, trichloroacetic, propionic, hexanoic, cyclopentylpropionic, glycolic, glutaric, pyruvic, lactic, malonic, succinic, sorbic, ascorbic, malic, maleic, fumaric, tartaric, citric, benzoic, 3-(4-hydroxybenzoyl)benzoic, picric, cinnamic, mandelic, phthalic, lauric, methanesulfonic, ethanesulfonic, 1,2-ethane-disulfonic, 2-hydroxyethanesulfonic, benzenesulfonic, 4-chlorobenzenesulfonic, 2-naphthalenesulfonic, 4-toluenesulfonic, camphoric, camphorsulfonic, 4-methylbicyclo[2.2.2]-oct-2-ene-1-carboxylic, glucoheptonic, 3-phenylpropionic, trimethylacetic, tert-butylacetic, lauryl sulfuric, gluconic, benzoic, glutamic, hydroxynaphthoic, salicylic, stearic, muconic acid and the like acids; or (2) salts formed when an acidic proton present in the parent compound either (a) is replaced by a metal ion, e.g., an alkali metal ion, an alkaline earth ion or an aluminum ion, or alkali metal or alkaline earth metal hydroxides, such as sodium, potassium, calcium, magnesium, and barium hydroxide, ammonia or (b) coordinates with an organic base, such as aliphatic, alicyclic, or aromatic organic amines, such as methylamine, dimethylaminem, diethylamine, picoline, ethanolamine, diethanolamine, triethanolamine, N-methylglucamine and the like.

Salts further include, by way of example only, sodium, potassium, calcium, magnesium, ammonium, tetraalkylammonium and the like, and when the compound contains a basic functionality, salts of non-toxic organic or inorganic acids, such as hydrochloride, hydrobromide, tartrate, mesylate, acetate, maleate, oxalate and the like. The term "physiologically acceptable cation" refers to a non-toxic, physiologically acceptable cationic counterion of an acidic functional group. Such cations are exemplified by sodium, potassium, calcium, magnesium, ammonium and tetraalkylammonium cations and the like.

"Solvate" refers to a compound of the present invention or a salt thereof, that further includes a stoichiometric or non-stoichiometric amount of solvent bound by non-covalent intermolecular forces. Where the solvent is water, the solvate is a hydrate.

It is to be understood that compounds having the same molecular formula but differing in the nature or sequence of bonding of their atoms or in the arrangement of their atoms in space are termed "isomers". Isomers that differ in the arrangement of their atoms in space are termed "stereoisomers".

6.2 Embodiments of the Invention

The present invention allows, for example, for the rapid and accurate advanced detection of sepsis in a subject by measuring the amount of lysophosphatidylcholine in a sample from a subject, combined with one or more clinical markers and/or one or more biomarkers of the subject. Amounts of lysophosphatidylcholine can be constructed from one or more biological samples of subjects at a single time point ("snapshot"), or multiple such time points, during the course of time the subject is at risk for sepsis. Advantageously, sepsis can be diagnosed or predicted prior to the onset of conventional clinical symptoms, thereby allowing for more effective therapeutic intervention.

6.2.1. Subjects

In certain embodiments of the invention, the subject is an animal, preferably a mammal, more preferably a non-human primate. In the most preferred embodiments, the subject is a human.

Although the methods of the invention can be used for the advanced detection of any sepsis-related disease, particularly useful subjects include those that are at risk for sepsis. The subject can be at risk for sepsis according to any criteria known to the practitioner of skill in the art.

In certain embodiments, the subject is SIRS-negative. In the context of this invention, SIRS-negative subjects include healthy subjects that, for any reason according to the judgment of a practitioner of the art, are in need of advanced detection of sepsis. Such subjects include, but are not limited to, SIRS-negative subjects in hospital intensive care units and similarly situated subjects. The methods of the invention can be used for the advanced detection of SIRS, sepsis, severe sepsis, septic shock, multiple organ dysfunction or mortality. Further methods of the invention can be used to monitor for increased or decreased likelihood of onset of SIRS, sepsis, severe sepsis, septic shock, multiple organ dysfunction or mortality. In particular embodiments, the subject is a subject that might be at risk for a systemic inflammatory condition, such as a subject of an intensive care unit.

In further embodiments, the subject is SIRS-positive. The methods of the invention can be used for the advanced detection of sepsis, severe sepsis, septic shock, multiple organ dysfunction or mortality, or to detect conversion to SIRS-negative. Further methods of the invention can be used to monitor a treatment or prevention for increased or decreased likelihood of onset of sepsis, severe sepsis, septic shock, multiple organ dysfunction or mortality, or to monitor for possible conversion to SIRS-negative.

In further embodiments, the subject has sepsis. The methods of the invention can be used for the advanced detection of severe sepsis, septic shock, multiple organ dysfunction or mortality, or to detect conversion to SIRS-positive (and sepsis-negative) or SIRS-negative. Further methods of the invention can be used to monitor a treatment or prevention for increased or decreased likelihood of onset of severe sepsis, septic shock, multiple organ dysfunction or mortality, or to monitor for possible conversion to SIRS-positive (and sepsis-negative) or SIRS-negative.

In further embodiments, the subject has severe sepsis. The methods of the invention can be used for the advanced detection of septic shock, multiple organ dysfunction or mortality, or to detect conversion to sepsis, SIRS-positive (and sepsis-negative) or SIRS-negative. Further methods of the invention can be used to monitor a treatment or prevention for increased or decreased likelihood of onset of septic shock, multiple organ dysfunction or mortality, or to monitor for possible conversion to sepsis, SIRS-positive (and sepsis-negative) or SIRS-negative.

In further embodiments, the subject has septic shock. The methods of the invention can be used for the advanced detection of multiple organ dysfunction or mortality, or to detect conversion to severe sepsis, sepsis, SIRS-positive (and sepsis-negative) or SIRS-negative. Further methods of the invention can be used to monitor a treatment or prevention for increased or decreased likelihood of onset of multiple organ dysfunction or mortality, or to monitor for possible conversion to severe sepsis, sepsis, SIRS-positive (and sepsis-negative) or SIRS-negative.

In further embodiments, the subject has multiple organ dysfunction. The methods of the invention can be used for the advanced detection of mortality, or they can be used to detect conversion to septic shock, severe sepsis, sepsis, SIRS-positive (and sepsis-negative) or SIRS-negative. Further methods of the invention can be used to monitor a treatment or prevention for increased or decreased likelihood of onset of mortality, or to monitor for possible conversion to septic shock, severe sepsis, sepsis, SIRS-positive (and sepsis-negative) or SIRS-negative.

In preferred embodiments, the subject is SIRS-negative (i.e. the subject can be healthy) but in need of diagnosis or prognosis of a systemic inflammatory condition according to the judgment of a practitioner of skill in the art. The subject could be, for instance, a patient in an intensive care unit. Similarly, in preferred embodiments, subjects are SIRS-negative, and methods of the invention are used to assess likelihood of the onset of a systemic inflammatory condition. For instance, in a SIRS-negative subject judged to be at risk for a systemic inflammatory condition, for example according to a method of the invention, a course of intervention could be administered to the subject to prevent a systemic inflammatory condition. Such prevention of a systemic inflammatory condition can be monitored with a method of the invention.

In further preferred embodiments, subjects are SIRS-positive, and methods of the invention are used for the advanced detection of a further systemic inflammatory condition. Similarly, in preferred embodiments, subjects are SIRS-positive, and methods of the invention are used to monitor treatment of SIRS or prevention of the further systemic inflammatory condition. For instance, in a SIRS-positive subject judged to be at risk for a further systemic inflammatory condition, for example according to a method of the invention, a course of intervention could be administered to the subject to prevent the systemic inflammatory condition. Such prevention of the systemic inflammatory condition can be monitored with a method of the invention.

In specific embodiments, a subject is monitored using the methods, monitors and systems of the invention as frequently as necessary (e.g., during their stay in an intensive care unit) for the advanced detection of a systemic inflammatory condition. In a preferred embodiment, the subject is monitored soon after they arrive in an intensive care unit. In some embodiments, the subject is monitored daily after they arrive in an intensive care unit. In some embodiments, the subject is monitored every 1 to 3 hours, 3 to 8 hours, 8 to 12 hours, 12 to 16 hours, or 16 to 24 hours after they arrive in an intensive care unit. In some embodiments, the subject is monitored continuously after they arrive in an intensive care unit.

6.3 Lysophosphatidylcholine

In one aspect, the present invention provides for the advanced detection of sepsis in a subject based on measurement of an amount of lysophosphatidylcholine in fluid or tissue of the subject. In certain embodiments, measurement of lysophosphatidylcholine is made at a plurality of time points.

In certain embodiments, the amount of total lysophosphatidylcholine in a sample from a subject is used for the advanced detection of sepsis. Total lysophosphatidylcholine refers to an amount that corresponds to all lysophosphatidylcholine (free or bound or both) in the sample. For instance, total lysophosphatidylcholine can refer to those molecules in the sample that are according to formula (I):

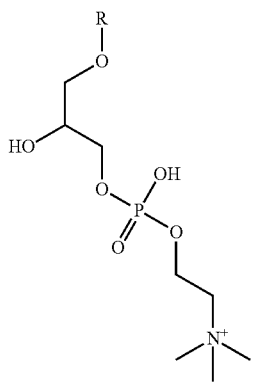

(I)

or any salt or solvate thereof, wherein R is any acyl group. The acyl group can be any acyl group known to those of skill in the art. Exemplary acyl groups include caproyl, lauroyl, myristoyl, palmitoyl, stearoyl, palmitoleyl, oleyl, arachidonyl and linoleyl. Preferably, total lysophosphatidylcholine includes at least 1-O-palmitoyl-2-lyso-sn-glycero-3-phosphocholine and 1-O-stearoyl-2-lyso-sn-glycero-3-phosphocholine. In typical embodiments, amount of lysophosphatidylcholine is measured without regard to the identity of the acyl group. Useful techniques are described herein.

In certain embodiments, the amount of lysophosphatidylcholine measured at a plurality of time points and one or more clinical markers measured at a plurality of time points are used for the advanced detection of sepsis. In certain embodiments, the clinical markers are temperature and respiratory rate.

In further embodiments, one or more biomarkers are additionally used for the advanced detection of sepsis.

The practitioner of skill in the art can use any technique to measure or indicate amount of lysophosphatidylcholine in a sample. In certain embodiments, the practitioner of skill can measure an amount or value from a sample that correlates to total lysophosphatidylcholine. For instance, in certain samples from subjects, a fraction of total lysophosphatidylcholine can be free from other molecules while a further fraction of total lysophosphatidylcholine can be bound by other molecules. For example, a fraction of total lysophosphatidylcholine can be bound by albumin. The sample preparation and measurement techniques used by the practitioner of skill can affect the amount of lysophosphatidylcholine actually measured. For instance, precipitation and/or purification techniques can separate free and bound lysophosphatidylcholine. Detection techniques might be more sensitive to free lysophosphatidylcholine or to bound lysophosphatidylcholine. This amount measured can be correlated to the amount of total lysophosphatidylcholine in the sample according to methods available to the practitioner of skill. In certain embodiments, a measurement of free lysophosphatidylcholine is used to indicate the amount of total lysophosphatidylcholine in the sample. In certain embodiments, a measurement of bound lysophosphatidylcholine is used to indicate the amount of total lysophosphatidylcholine in the sample. In certain embodiments, a measurement of bound and free lysophosphatidylcholine is used to indicate the amount of total lysophosphatidylcholine in the sample. In certain embodiments, free lysophosphatidylcholine can be used for the advanced detection of sepsis in the methods of the invention. In certain embodiments, bound lysophosphatidylcholine can be used for the advanced detection of sepsis in the methods of the invention. In certain embodiments, free and bound lysophosphatidylcholine can be used for the advanced detection of sepsis in the methods of the invention.

In another aspect, the present invention provides for the advanced detection of sepsis in a subject based on measurement an amount of a compound according to formula (I):

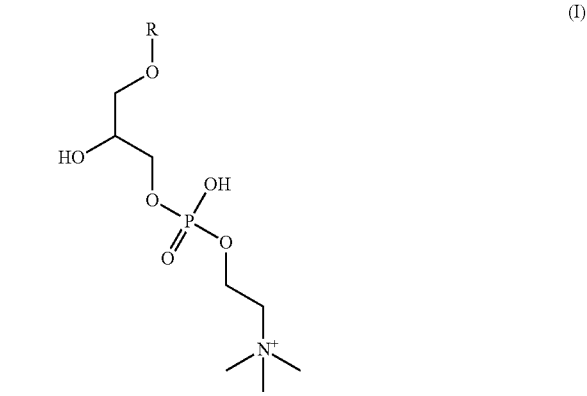

(I)

or any salt or solvate thereof, wherein R is an acyl group, in fluid or tissue of the subject.

Exemplary salts of formula (I) are provided by formula (Ia):

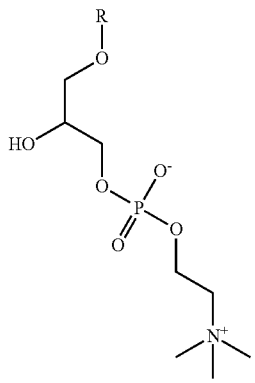

(Ia)

wherein said salt can be coordinated with any ion or ions known to those of skill in the art. The ion or ions can be physiological but need not be physiological. For instance, the ion or ion can result from contact with the salt during the preparation of the sample from the subject, as described below. In some embodiments, the salt is coordinated with an anion, for instance, a physiological anion known to those of skill in the art. Exemplary anions include chloride, bromide, phosphate, acetate, carbonate, bicarbonate and sulfate. In some embodiments, the salt is coordinated with a cation, for instance, a physiological cation, known to those of skill in the art. Exemplary cations include sodium, potassium, calcium, magnesium and ammonium. In some embodiments, as will be recognized by those of skill in the art, the salt is coordinated with one or more anions and with one or more cations.

The acyl group can be any acyl group known to those of skill in the art. In certain embodiments the acyl group is saturated. Exemplary saturated acyl groups include caproyl, lauroyl, myristoyl, palmitoyl and stearoyl. In further embodiments, the acyl group is monounsaturated. Exemplary monounsaturated acyl groups include palmitoleyl and oleyl. In further embodiments, the acyl group is polyunsaturated. Exemplary polyunsaturated acyl groups include arachidonyl and linoleyl.

More systematically, in certain embodiments, the acyl group is $C_{10}$-$C_{22}$ acyl. In certain embodiments, the acyl group is $C_{14}$-$C_{22}$ acyl. Exemplary acyl groups include 16:0, 18:0, 18:1, 18:2, 20:4(n-6) and 22:6(n-3), according to nomenclature familiar to those of skill in the art. In such nomenclature, the first number indicates the number of carbon atoms in the acyl group, and the second number indicates the number of double bonds in the group. For instance, "18:1" indicates an acyl group with 18 carbon atoms and one double bond. Numbers in parentheses, if any, indicate the location of the double bond, and the notation "(n-x)" indicates a double bond x positions away from the terminal methyl of the longest chain of the fatty acid. See *Biochem. J.*, 1978, 171, 21-35; *Chem. Phys. Lipids*, 1978, 21, 159-173; *Eur. J. Biochem.*, 1977, 79, 11-21; *Hoppe-Seyler's Z. Physiol. Chem.*, 1977, 358, 617-631; *J. Lipid Res.*, 1978, 19, 114-128; *Lipids*, 1977, 12, 455-468; *Mol. Cell. Biochem.*, 1977, 17, 157-171; *Biochemical Nomenclature and Related Documents*, 2nd edition, Portland Press, 1992, pages 180-190, the contents of which are hereby incorporated by reference in their entireties.

In certain embodiments, the acyl group is $C_{14}$-$C_{22}$ acyl. In certain embodiments, the acyl group is $C_{16}$-$C_{20}$ acyl. In further embodiments, the acyl group is $C_{16}$-$C_{18}$ acyl. In certain embodiments, the acyl group is hexadecanoyl or octadecanoyl. In particular embodiments, the acyl group is $C_{16}$ acyl. In a preferred embodiment, the acyl group is hexadecanoyl. In further particular embodiments, the acyl group is $C_{18}$ acyl. In a preferred embodiment, the acyl group is octadecanoyl.

The compound according to formula (I) can be any form of the compound from the subject, for instance any salt or solvate of the compound that can be identified by those of skill in the art. In preferred embodiments, the compound is in the form of a sodium salt.

In certain embodiments, the amounts of the compound according to formula (I) may include a precursor of the compound known to those of skill in the art. The precursor can be one or two or three, or in some embodiments more, steps prior to the compound according to formula (I) in a biosynthetic pathway known to those of skill in the art. In further embodiments, the amounts of the compound according to formula (I) may include a downstream metabolite of the compound in a biosynthetic pathway known to those of skill in the art. The downstream metabolite can be one or two or three, or in some embodiments more, steps following the compound according to formula (I) in a biosynthetic pathway known to those of skill in the art. In certain embodiments, the biosynthetic pathway is a de novo pathway for the synthesis of platelet activating factor known to those of skill in the art. In further embodiments, the biosynthetic pathway is a remodeling pathway for the synthesis of platelet activating factor known to those of skill in the art.

In particular embodiments, the metabolite is a 1-O-acyl-2-O-acyl-sn-glycero-3-phosphocholine. In preferred embodiments, the 2-O-acyl group is any acyl group described above or acetyl. In particular embodiments, the metabolite is a 1-O-acyl-2-O-alkyl-sn-glycero-3-phosphocholine. In preferred embodiments, the 2-O-alkyl group is any group known to those of skill in the art to modify a glycero-3-phosphocholine, for instance any $C_{14}$-$C_{22}$ alkyl.

6.4 Clinical Markers

In another aspect, the present invention provides for the advanced detection of sepsis in a subject based on measurement at a plurality of time points of one or more clinical markers of the subject. In certain embodiments, the clinical markers are measured in conjunction with measurements of the amounts of lysophosphatidylcholine or the compound of formula (I). The clinical markers may be measured at the same time the measurements of the amounts of lysophosphatidylcholine or the compound of formula (I) are made, for example, simultaneously with the blood draws for measurement of the amounts. The clinical markers may be measured at a plurality of time points than those at which the measurements of the amounts of lysophosphatidylcholine or the compound of formula (I) are made, for example, up to several hours before or after the blood draws for measurement of the amounts. The clinical markers may be measured on the same day as the measurements of the amounts of lysophosphatidylcholine or the compound of formula (I) are made, for example, within 24 hours of the blood draws for measurement of the amounts. The clinical markers may be measured as a maximum or minimum value over the 24 hours preceding measurement of the amounts of lysophosphatidylcholine or the compound of formula (I) are made (this is the Apache II measurement).

The clinical marker for the advanced detection of sepsis can be any clinical marker for a systemic inflammatory condition, including SIRS, sepsis, severe sepsis, septic shock or MOD, known to those of skill in the art. In certain embodiments, the clinical marker is according to a clinical severity model for sepsis. Such models include, but are not limited to, the Acute Physiology and Chronic Health Evaluation score (APACHE, and its refinements APACHE II and III) (Knaus et al., 1985, Crit Care Med 13: 818-829; Knaus et al., 1991, Chest 100: 1619-1636), the Mortality Prediction Model (MPM) (Lemeshow et al., 1993, JAMA 270: 2957-2963), the Simplified Acute Physiology (SAPS) score (Le Gall et al., 1984, Crit Care Med 12: 975-977), the Multiple Organ Dysfunction Score (MODS) (Marshall et al., 1995, Crit Care Med 23: 1638-1652), the Sequential Organ Failure Assessment (SOFA) score (Ferreira et al., 2002, JAMA 286: 1754-1758), the Logistical Organ Dysfunction Score (LODS) (Le Gall et al., 1996, JAMA 276: 802-810) and the predisposition, infection, response, and organ dysfunction (PIRO) concept (Levy et al., 2003, Intensive Care Med 29: 530-538) (the contents of each reference is hereby incorporated in its entirety).

In certain embodiments, the clinical markers comprise one or more measurements used by those of skill in the art to aid in the prognosis or diagnosis of sepsis. Such markers include, but are not limited to, temperature, heart rate, systolic blood pressure, diastolic blood pressure, mean artery pressure, white blood cell count, differential white blood cell count (monocytes, lymphocytes, granulocytes and/or neutrophils), immature neutrophil to total neutrophil ratio, platelet count and serum creatinine.

In preferred embodiments, the clinical markers are respiratory rate and temperature.

In certain embodiments, a body temperature greater than 38° C. detects sepsis. In certain embodiments, a body temperature greater than 38.5° C. detects sepsis. In certain embodiments, a body temperature greater than 39° C. detects sepsis. In certain embodiments, a body temperature greater than 39.5° C. detects sepsis. In certain embodiments, a body temperature greater than 40° C. detects sepsis.

In certain embodiments, a body temperature less than 36° C. detects sepsis. In certain embodiments, a body temperature less than 35.5° C. detects sepsis. In certain embodiments, a body temperature less than 35° C. detects sepsis. In certain embodiments, a body temperature less than 34.5° C. detects sepsis. In certain embodiments, a body temperature less than 34° C. detects sepsis.

Temperature can be measured by any technique deemed useful by one of skill in the art. Exemplary techniques are described herein including the monitors and systems described below.

In certain embodiments, a respiratory rate greater than 20 breaths per minute detects sepsis. In certain embodiments, a respiratory rate greater than 21 breaths per minute detects sepsis. In certain embodiments, a respiratory rate greater than 22 breaths per minute detects sepsis. In certain embodiments, a respiratory rate greater than 23 breaths per minute detects sepsis. In certain embodiments, a respiratory rate greater than 24 breaths per minute detects sepsis. In certain embodiments, a respiratory rate greater than 25 breaths per minute detects sepsis.

Respiratory rate can be measured by any technique deemed useful by one of skill in the art. Exemplary techniques are described herein including the monitors and systems described below.

6.5 Biomarkers

In another aspect, the present invention provides for the advanced detection of sepsis in a subject based additionally on measurement at a plurality of time points of one or more biomarkers of the subject. In certain embodiments, the biomarkers are measured in conjunction with the measurements at a plurality of time points of clinical markers, and/or in conjunction with measurements of the amounts of lysophosphatidylcholine or the compound of formula (I). The biomarkers may be measured at the same time the measurements of the amounts of lysophosphatidylcholine or the compound of formula (I) are made, for example, from the same blood draw used for measurement of lysophosphatidylcholine. The biomarkers may be measured at a plurality of time points than those at which the measurements of the amounts of lysophosphatidylcholine or the compound of formula (I) are made, for example, from different blood draws taken hours apart. The biomarkers may also be measured at a plurality of time points than those at which the clinical marker measurements are made, for example, up to several hours before or after the clinical marker measurement.

Each biomarker can be of any type of biomarker for a systemic inflammatory condition known to those of skill in the art including protein, peptide, nucleic acid, lipid, phospholipid and metabolite (e.g., protein, peptide, nucleic acid, nucleoside, lipid or phospholipid metabolite) biomarkers. Further exemplary biomarkers for the prognosis or diagnosis of a systemic inflammatory condition, and methods of their evaluation, are described in U.S. Patent Application Publication Nos. 20030194752, 20040096917, 20040097460, 20040106142, 20040157242, and U.S. Provisional Application Nos. 60/671,620, filed Apr. 15, 2005, 60/671,941, filed Apr. 15, 2005, and 60/674,046, filed Apr. 22, 2005, the contents of which are hereby incorporated by reference in their entireties. Further exemplary biomarkers for sepsis include endotoxin; bacterial DNA; acute phase proteins such as protein C, procalcitonin, LBP-LPS-binding protein; coagulation factors such as fibrin degrading products, antitrombin III, dimer D; membrane cell markers such as HLA-DR, CD-64, E-selectin; hormones such as cortisol, ACTH; soluble receptors such as CD-14, sTNFRI, sTNF-RII; and cytokines such as TNF, IL-6, IL-8 and IL-10; and others such as D-dimer, prothrombin time, activated partial thromboplastin time, plasminogen activator inhibitor-1, soluble thrombomodulin, IL-6, IL-10, IL-8, protein C, thrombin activatable fibrinolysis inhibitor, protein S, antithrombin, TNF-α, copeptin, high mobility group box 1, triggering receptor expressed on myeloid cells 1, and albumin. See, e.g., Kinasewitz et al., 2004, Critical Care 8:R82-R90, Bozza et al., 2005, Mem. Inst. Oswaldo Cruz 100(s) 1:217-221, the contents of which are hereby incorporated by reference in their entireties. Preferred biomarkers include procalcitonin. The sequence of the procalcitonin protein, for example, the human procalcitonin protein, is well known to those of skill in the art. An exemplary procalcitonin protein can be identified, for example, by accession number P01258, (UniProtKB/Swiss-Prot) by one of skill in the art.

In one embodiment, any of the biomarkers are human.

6.6 Measurement of Lysophosphatidylcholine

In this section and the sections that follow, unless specified otherwise, the term lysophosphatidylcholine refers to an amount of lysophosphatidylcholine in fluid or tissue of a subject or to an amount of the compound according to formula (I), its salt or solvate thereof, wherein R is $C_{10}$-$C_{22}$ acyl, in the fluid or tissue of a subject.

In certain embodiments of the invention, the method of measuring lysophosphatidylcholine is not critical. Accordingly, the present invention provides methods for the advance detection of sepsis that comprise the step of detecting sepsis from measuring at a plurality of time points an amount of lysophosphatidylcholine, for example, along with one or more clinical markers and/or one or more biomarkers, as described above.

The amount of lysophosphatidylcholine can be measured by one practicing a method of the invention in any manner whatsoever. Exemplary techniques are described herein. As described above, any technique that indicates lysophosphatidylcholine in the sample can be used in the methods of the invention. In certain embodiments, the methods are based on free lysophosphatidylcholine in the sample. In certain embodiments, the methods are based on bound lysophosphatidylcholine in the sample. In certain embodiments, the methods are based on total lysophosphatidylcholine in the sample.

The amount of a lysophosphatidylcholine can be measured by one practicing a method of the invention in any manner whatsoever. Exemplary techniques are described herein.

When an amount of lysophosphatidylcholine is to be evaluated, each lysophosphatidylcholine in the amount should be evaluated according to a technique suitable for that lysophosphatidylcholine. For example, the amount of 1-O-palmitoyl-2-lyso-sn-glycero-3-phosphocholine should be evaluated according to a technique suitable for 1-O-palmitoyl-2-lyso-sn-glycero-3-phosphocholine. In advantageous embodiments, lysophosphatidylcholines within the amount that can be evaluated by the same or by compatible techniques can be evaluated together. In other advantageous embodiments lysophosphatidylcholines and additional biomarkers that can be evaluated by the same or by compatible techniques can be evaluated together. For instance, protein, peptide, lipid, phospholipid and metabolite biomarkers that can be evaluated by immunoassays can be evaluated together or in groups according to techniques known to those of skill in the art.

In one embodiment, only a single biological sample taken at a single point in time from the subject is used to detect sepsis prior to conversion. In another embodiment, a plurality of biological samples taken at different points in time from the subject are used to detect sepsis prior to conversion.

In a specific embodiment, the amount of lysophosphatidylcholine is obtained using samples collected from the subject at one time point. In another specific embodiment, the amount of lysophosphatidylcholine is obtained using samples obtained from the subject at separate time points. In one example, these samples are obtained from the subject either once or, alternatively, on a daily basis, or more frequently, e.g., every 2, 3, 4, 6, 8 or 12 hours.

Lysophosphatidylcholine can be obtained from any biological sample, which can be, by way of example and not of limitation, blood, plasma, serum, saliva, sputum, urine, cerebral spinal fluid, cells, a cellular extract, a tissue sample, a tissue biopsy, a stool sample or any sample that may be obtained from a subject using techniques well known to those of skill in the art. The precise biological sample that is taken from the subject may vary, but the sampling preferably is minimally invasive and is easily performed by conventional techniques.

In advantageous embodiments, the amount of lysophosphatidylcholine can be detected, measured or monitored by one or more enzymatic assays. The enzymatic assays can be any enzymatic assays known to those of skill in the art to be useful for detecting, measuring or monitoring one or more of the biomarkers of the invention.

In certain embodiments, the enzymatic assays can be according to published application JP 2002-17938 (Kishimoto et al., 2002, Method of Measuring Phospholipid), or according to Kishimoto et al., 2002, *Clinical Biochem.* 35:411-416, the contents of which are hereby incorporated by reference in their entireties.

In certain embodiments, the amount of lysophosphatidylcholine can be measured by contacting a sample of the invention with an enzyme capable of hydrolyzing lysophosphatidylcholine to yield glycerophosphorylcholine. The enzyme can be any such enzyme known to those of skill in the art. Exemplary enzymes include lysophospholipases such as EC 3.1.1.5 (commercially available from, e.g., Asahi Chemical Co.). In certain embodiments, the lysophospholipase preferentially hydrolyzes lysophospholipids relative to other phospholipids. In certain embodiments, the lysophospholipase is from *Bacillus*. In certain embodiments, the lysophospholipase is according to JP 2002-17938.

The resulting glycerophosphorylcholine can be detected, measured or monitored according to any technique apparent to those of skill in the art. For instance, in certain embodiments, the glycerophosphorylcholine can be contacted with a glycerophosphorylcholine diesterase known to those of skill in the art (e.g. EC 3.1.4.2) under conditions suitable to yield choline. The resulting choline can be contacted with a choline oxidase known to those of skill in the art (e.g. EC 1.1.3.17) under conditions suitable to yield peroxide. Use of the choline oxidase enables the method to detect lysophosphatidylcholine in preference to other lysophospholipids such as lysophospholipids comprising serine or ethanolamine. The resulting peroxide can be detected by any technique apparent to those of skill in the art including, for example, colorimetric techniques.

The detection of hydrogen peroxide can be accomplished by any technique apparent to one of skill in the art. Exemplary techniques include chemiluminescence (Kiba et al., 2003, *Analytical Science* 19(6):823-827), fluorescence (Zhang et al., 199, Talanta 48(5):1031-1038; Chen et al., 2001, *Analytica Chimica* 434(1):51-58), and spectrophotometry (Pappas et al., 2002, *Analytica Chimica* 455(2):305-313). Other exemplary techniques include metal complexes (Paleologos, 2002, *Analytical Chemistry* 74(1):100-106) as well as redox mediated electrochemical detection (e.g., commercially available glucose meters).

In advantageous embodiments, peroxidase activity can be detected with a fluorogenic substrate. Such embodiments provide rapid and sensitive techniques for the detection of the amount of lysophosphatidylcholine in the sample. These techniques thus provide rapid and sensitive assays for the advanced detection of a systemic inflammatory condition as described herein. The fluorogenic substrate can be any fluorogenic substrate known to those of skill in the art to be capable of conversion to a fluorescent product by a peroxidase in the presence of peroxide under suitable conditions, e.g. with water and oxygen. In particular embodiments, the fluorogenic substrate is 10-acetyl-3,7-dihydroxyphenoxazine. This substrate can be obtained from commercial suppliers (e.g. Amplex Red, Invitrogen). Those of skill in the art will recognize that this fluorogenic substrate can be converted to the fluorescent product 7-hydroxy-3H-phenoxazin-3-one (resorufin), detectable by techniques apparent to those of skill in the art. Useful detection techniques include, of course, fluorescence detection. Preferably, the detection methods are carried out under conditions in which the product can be formed and detected. Useful conditions and results are described in the working examples below.

In certain embodiments, the glycerophosphorylcholine can be contacted with a glycerophosphorylcholine phosphodiesterase known to those of skill in the art under conditions suitable to yield glycerol-3-phosphate. The resulting glycerol-3-phosphate can be contacted with a glycerol-3-phosphate oxidase known to those of skill in the art under conditions suitable to yield peroxide. Useful glycerol-3-phosphate oxidases include those derived from *Streptococcus, Aerococcus*, and *Pediococcus*, and those described in JP 2002-17938. The resulting peroxide can be detected by any technique apparent to those of skill in the art including, for example, colorimetric techniques.

In certain embodiments, the glycerophosphorylcholine can be contacted with a glycerophosphorylcholine phosphodiesterase known to those of skill in the art under conditions suitable to yield glycerol-3-phosphate. The resulting glycerol-3-phosphate can be contacted with a glycerol-3-phosphate dehydrogenase known to those of skill in the art under conditions suitable to yield a detectable product. For instance, the contacting can be in the presence of $NAD^+$ to yield detectable NADH. The contacting can also be in the presence of $NADP^+$ to yield detectable NADPH.

Techniques for detecting, measuring or monitoring detectable products such as peroxide, NADH and NADPH are well known to those of skill in the art. Useful techniques are described in JP 2002-17938, Misaki, 1999, *Modern Medical Laboratory* 27(8): 973-980, (1999), Japanese Patent No. 1594750, Japanese Patent Laid-Open No. 05-229993, and Aoyama, 1997, *Journal of Medical Technology* 14: 1014-1019, the contents of which are hereby incorporated by reference in their entireties.

6.7 Measurement of Biomarkers

The biological sample can be processed or purified according to the judgment of those of skill in the art based on, for example, the type of biomarker and the measurement technique. For instance, when the biomarker is a lipid or phospholipid metabolite, the sample can be processed by extraction and/or chromatography. When the biomarker is a protein or peptide, for example when a panel of biomarkers is to be evaluated, the sample can be processed by precipitation, centrifugation, filtration and/or chromatography. When the biomarker is a nucleic acid, for example when a panel of biomarkers is to be evaluated, the sample can be processed to isolate nucleic acids by extraction, precipitation and/or chromatography.

These amounts can be determined through the use of any reproducible measurement technique or combination of measurement techniques. Such techniques include those that are well known in the art including any technique described herein. Typically, such techniques are used to measure amounts using a biological sample taken from a subject at a single point in time or multiple samples taken at multiple points in time.

In certain embodiments, methods of detection of the biomarker involve their detection via interaction with a biomarker-specific antibody, for example, antibodies directed to the biomarker of the invention. Antibodies can be generated utilizing standard techniques well known to those of skill in the art. In specific embodiments, antibodies can be polyclonal, or more preferably, monoclonal. An intact antibody, or an antibody fragment (e.g., scFv, Fab or $F(ab')_2$) can, for example, be used.

For example, antibodies, or fragments of antibodies, specific for a biomarker can be used to quantitatively or qualitatively detect the presence of a biomarker. This can be accomplished, for example, by immunofluorescence techniques. Antibodies (or fragments thereof) can, additionally, be employed histologically, as in immunofluorescence or immunoelectron microscopy, for in situ detection of a biomarker. In situ detection can be accomplished by removing a biological sample (e.g., a biopsy specimen) from a subject, and applying thereto a labeled antibody that is directed to a biomarker. The antibody (or fragment) is preferably applied by overlaying the antibody (or fragment) onto a biological sample. Through the use of such a procedure, it is possible to determine not only the presence of the biomarker, but also its distribution, in a particular sample. A wide variety of well-known histological methods (such as staining procedures) can be utilized to achieve such in situ detection.

Immunoassays for a biomarker typically comprise incubating a biological sample of a detectably labeled antibody capable of identifying a biomarker, and detecting the bound antibody by any of a number of techniques well-known in the art. As discussed in more detail, below, the term "labeled" can refer to direct labeling of the antibody via, e.g., coupling (i.e., physically linking) a detectable substance to the antibody, and can also refer to indirect labeling of the antibody by reactivity with another reagent that is directly labeled. Examples of indirect labeling include detection of a primary antibody using a fluorescently labeled secondary antibody.

The biological sample can be brought in contact with and immobilized onto a solid phase support or carrier such as nitrocellulose, or other solid support which is capable of immobilizing cells, cell particles or soluble proteins. The support can then be washed with suitable buffers followed by treatment with the detectably labeled fingerprint gene-specific antibody. The solid phase support can then be washed with the buffer a second time to remove unbound antibody. The amount of bound label on solid support can then be detected by conventional methods.

By "solid phase support or carrier" is intended any support capable of binding an antigen or an antibody. Well-known supports or carriers include glass, polystyrene, polypropylene, polyethylene, dextran, nylon, amylases, natural and modified celluloses, polyacrylamides and magnetite. The nature of the carrier can be either soluble to some extent or insoluble for the purposes of the present invention. The support material can have virtually any possible structural configuration so long as the coupled molecule is capable of binding to an antigen or antibody. Thus, the support configuration can be spherical, as in a bead, or cylindrical, as in the inside surface of a test tube, or the external surface of a rod. Alternatively, the surface can be flat such as a sheet, test strip, etc. Preferred supports include polystyrene beads. Those skilled in the art will know many other suitable carriers for binding antibody or antigen, or will be able to ascertain the same by use of routine experimentation.

One of the ways in which an antibody specific for a biomarker can be detectably labeled is by linking the same to an enzyme and use in an enzyme immunoassay (EIA) (Voller, 1978, "The Enzyme Linked Immunosorbent Assay (ELISA)", Diagnostic Horizons 2:1-7, Microbiological Associates Quarterly Publication, Walkersville, Md.; Voller et al., 1978, J. Clin. Pathol. 31:507-520; Butler, J. E., 1981, Meth. Enzymol. 73:482-523; Maggio, E. (ed.), 1980, Enzyme Immunoassay, CRC Press, Boca Raton, Fla.; Ishikawa, E. et al., (eds.), 1981, Enzyme Immunoassay, Kgaku Shoin, Tokyo, each of which is hereby incorporated by reference in its entirety). The enzyme which is bound to the antibody will react with an appropriate substrate, preferably a chromogenic substrate, in such a manner as to produce a chemical moiety which can be detected, for example, by spectrophotometric, fluorimetric or by visual means. Enzymes which can be used to detectably label the antibody include, but are not limited to, malate dehydrogenase, staphylococcal nuclease, delta-5-steroid isomerase, yeast alcohol dehydrogenase, alpha-glycerophosphate, dehydrogenase, triose phosphate isomerase, horseradish peroxidase, alkaline phosphatase, asparaginase, glucose oxidase, beta-galactosidase, ribonuclease, urease, catalase, glucose-6-phosphate dehydrogenase, glucoamylase and acetylcholinesterase. The detection can be accomplished by colorimetric methods which employ a chromogenic substrate for the enzyme. Detection can also be accomplished by visual comparison of the extent of enzymatic reaction of a substrate in comparison with similarly prepared standards.

Detection can also be accomplished using any of a variety of other immunoassays. For example, by radioactively labeling the antibodies or antibody fragments, it is possible to detect a biomarker through the use of a radioimmunoassay (RIA) (see, for example, Weintraub, B., Principles of Radioimmunoassays, Seventh Training Course on Radioligand Assay Techniques, The Endocrine Society, March, 1986, which is incorporated by reference herein). The radioactive isotope (e.g., $^{125}I$, $^{131}I$, $^{35}S$ or $^{3}H$) can be detected by such means as the use of a gamma counter or a scintillation counter or by autoradiography.

It is also possible to label the antibody with a fluorescent compound. When the fluorescently labeled antibody is exposed to light of the proper wavelength, its presence can then be detected due to fluorescence. Among the most commonly used fluorescent labeling compounds are fluorescein isothiocyanate, rhodamine, phycoerythrin, phycocyanin, allophycocyanin, o-phthaldehyde and fluorescamine.

The antibody can also be detectably labeled using fluorescence emitting metals such as $^{152}Eu$ or others of the lanthanide series. These metals can be attached to the antibody using such metal chelating groups as diethylenetriaminepentacetic acid (DTPA) or ethylenediaminetetraacetic acid (EDTA).

The antibody also can be detectably labeled by coupling it to a chemiluminescent compound. The presence of the chemiluminescent-tagged antibody is then determined by detecting the presence of luminescence that arises during the course of a chemical reaction. Examples of particularly useful chemiluminescent labeling compounds are luminol, isoluminol, theromatic acridinium ester, imidazole, acridinium salt and oxalate ester.

Likewise, a bioluminescent compound can be used to label the antibody of the present invention. Bioluminescence is a type of chemiluminescence found in biological systems in, which a catalytic protein increases the efficiency of the chemiluminescent reaction. The presence of a bioluminescent protein is determined by detecting the presence of luminescence. Important bioluminescent compounds for purposes of labeling are luciferin, luciferase and aequorin.

In another embodiment, specific binding molecules other than antibodies, such as aptamers, may be used to bind the biomarkers.

Amounts of biomarkers may also be determined by the use of one or more of the following methods described below. For example, methods may include nuclear magnetic resonance (NMR) spectroscopy, a mass spectrometry method, such as electrospray ionization mass spectrometry (ESI-MS), ESI-MS/MS, ESI-MS/(MS)$^n$ (n is an integer greater than zero), matrix-assisted laser desorption ionization time-of-flight mass spectrometry (MALDI-TOF-MS), surface-enhanced laser desorption/ionization time-of-flight mass spectrometry (SELDI-TOF-MS), desorption/ionization on silicon (DIOS), secondary ion mass spectrometry (SIMS), quadrupole time-of-flight (Q-TOF), atmospheric pressure chemical ionization mass spectrometry (APCI-MS), APCI-MS/MS, APCI-(MS)$^n$, atmospheric pressure photoionization mass spectrometry (APPI-MS), APPI-MS/MS, and APPI-(MS)$^n$. Other mass spectrometry methods may include, inter alia, quadrupole, Fourier transform mass spectrometry (FTMS) and ion trap. Other suitable methods may include chemical extraction partitioning, column chromatography, ion exchange chromatography, hydrophobic (reverse phase) liquid chromatography, isoelectric focusing, one-dimensional polyacrylamide gel electrophoresis (PAGE), two-dimensional polyacrylamide gel electrophoresis (2D-PAGE) or other chromatography, such as thin-layer, gas or liquid chromatography, or any combination thereof. In one embodiment, the biological sample may be fractionated prior to application of the separation method.

In specific embodiments of the invention, the biomarkers are nucleic acids. Such biomarkers and corresponding amounts may be generated, for example, by detecting the expression product (e.g., a polynucleotide or polypeptide) of one or more genes known to those of skill in the art. In a specific embodiment, the biomarkers and corresponding amounts in a biomarker profile are obtained by detecting and/or analyzing one or more nucleic acids using any method well known to those skilled in the art including, but by no means limited to, hybridization, microarray analysis, RT-PCR, nuclease protection assays and Northern blot analysis. As will be recognized by those of skill in the art, in convenient embodiments, the biological sample can be split, with one portion evaluated for nucleic acid biomarkers, and another portion evaluated for other biomarkers such as proteins, peptides, lipids, phospholipids and metabolites. In fact, the biological sample can be divided as many times as desired by the practitioner of skill to facilitate evaluation or measurement of each biomarker in a plurality or panel of biomarkers.

In certain embodiments, the amounts for biomarkers in a biomarker profile are obtained by hybridizing to detectably labeled nucleic acids representing or corresponding to the nucleic acid sequences in mRNA transcripts present in a biological sample (e.g., fluorescently labeled cDNA synthesized from the sample) to a microarray comprising one or more probe spots.

Several chromatographic techniques may be used to separate biomarkers. For example, amplification products may be separated by agarose, agarose-acrylamide or polyacrylamide gel electrophoresis using conventional methods. See Sambrook et al., 2001. Several techniques for detecting biomarkers quantitatively without electrophoresis may also be used according to the invention (see, e.g., *PCR Protocols, A Guide to Methods and Applications*, Innis et al., 1990, Academic Press, Inc. N.Y., which is hereby incorporated by reference). For example, chromatographic techniques may be employed to effect separation. There are many kinds of chromatography which may be used in the present invention: adsorption, partition, ion-exchange and molecular sieve, HPLC, and many specialized techniques for using them including column, paper, thin-layer and gas chromatography (Freifelder, Physical Biochemistry Applications to Biochemistry and Molecular Biology, 2nd ed., Wm. Freeman and Co., New York, N.Y., 1982, which is hereby incorporated by reference).

In certain embodiments, one or more of the biomarkers is a protein. Standard techniques may be utilized for determining the amount of the protein or proteins of interest present in a sample. For example, standard techniques can be employed using, e.g., immunoassays such as, for example Western blot, immunoprecipitation followed by sodium dodecyl sulfate polyacrylamide gel electrophoresis, (SDS-PAGE), immunocytochemistry, and the like to determine the amount of protein or proteins of interest present in a sample. One exemplary agent for detecting a protein of interest is an antibody capable of specifically binding to a protein of interest, preferably an antibody detectably labeled, either directly or indirectly.

For such detection methods, if desired a protein from the sample to be analyzed can easily be isolated using techniques which are well known to those of skill in the art. Protein isolation methods can, for example, be such as those described in Harlow and Lane, 1988, Antibodies: A Laboratory Manual. Cold Spring Harbor Laboratory Press (Cold Spring Harbor, N.Y.), which is incorporated by reference herein in its entirety.

In certain embodiments, methods of detection of the protein or proteins of interest involve their detection via interaction with a protein-specific antibody. For example, antibodies directed to a protein of interest. Antibodies can be generated utilizing standard techniques well known to those of skill in the art. In specific embodiments, antibodies can be polyclonal, or more preferably, monoclonal. An intact antibody, or an antibody fragment (e.g., scFv, Fab or $F(ab')_2$) can, for example, be used. Exemplary immunoassays are described above.

6.8 Advanced Detection of Sepsis

In certain methods of the invention, the amount of lysophosphatidylcholine in the subject is used for the advanced detection of sepsis, for example, along with one or more clinical markers and/or one or more biomarkers, as described above. As described above, the amount of lysophosphatidylcholine can be measured directly, or a measurement can be made that correlates to that amount. In certain embodiments, free lysophosphatidylcholine is measured. In certain embodiments, bound lysophosphatidylcholine is measured. In certain embodiments, total lysophosphatidylcholine is measured.

In certain methods of the invention, the amount of one or more compounds of formula (I) in the subject are used for the advanced detection of sepsis.

In certain methods of the invention, the amount of total lysophosphatidylcholine and one or more one or more compounds of formula (I) in the subject are used for the advanced detection of sepsis.

In some embodiments, a single sample from the subject is sufficient for the advanced detection of sepsis. In such embodiments, the amount of lysophosphatidylcholine can be compared to an internal reference in the biological sample that is present at a relatively constant amount in individuals similar to the subject. The internal reference can be any reference judged suitable to one of skill in the art and is preferably not related to the biomarker or to systemic inflammatory conditions. In certain embodiments, the internal reference is lysophosphatidylcholine, lysophosphatidylethanolamine or lysophosphatidylserine.

In some embodiments, a plurality of biological samples from the subject are evaluated for the advanced detection of sepsis. In such embodiments, change in the amount of lysophosphatidylcholine detects sepsis or indicates increased likelihood of onset of sepsis.

In certain embodiments, decreasing amounts of lysophosphatidylcholine detect sepsis or indicate increased likelihood of onset of sepsis. For instance, in certain embodiments, a second amount that is less than 95%, 90%, 80%, 75%, 50%, 33%, 25%, 20% or 10% of a previous amount detects sepsis or indicates increased likelihood of onset of sepsis In certain embodiments, advanced detection of sepsis can be based on a comparison of the amount of lysophosphatidylcholine in a sample of the subject to a reference amount of lysophosphatidylcholine. Reference amounts are described in the section below. Significantly, the amount of the reference amount need not be obtained or measured by a practitioner of a method of the invention. Instead, the reference amount can be identified by consultation of amounts of the reference in reference populations available to those of skill in the art. Such amounts can be published, for example, in scientific literature on electronic databases.

In preferred embodiments, the reference amount is measured by the same technique or a comparable technique used to measure the amount in the sample. For instance, preferably, if free lysophosphatidylcholine is measured in the sample, the reference amount can be based on free lysophosphatidylcholine in a reference subject or a reference population. For instance, preferably, if bound lysophosphatidylcholine is measured in the sample, the reference amount can be based on bound lysophosphatidylcholine. Of course, if total lysophosphatidylcholine and the reference amount are measured by different techniques, correlation of the two amounts should be within the ability of the practitioner of skill.

If lysophosphatidylcholine is measured in the sample, the reference amount can be based on the lysophosphatidylcholine in a reference subject or reference population. Of course, if lysophosphatidylcholine and the reference amount are measured by different techniques, correlation of the two amounts should be within the ability of the practitioner of skill When a reference amount is used, the difference between the reference amount and the amount in the test subject is used by a practitioner of skill in the art to detect sepsis. In certain embodiments, if the amount in the test subject is between 10-190%, 20-180%, 30-170%, 40-160%, 50-150%, 75-125%, 80-120%, 90-110% or 95-105% of the reference amount, sepsis or an increased likelihood of onset of sepsis is indicated.

If a threshold reference amount is used, the difference between the threshold and the amount in the test subject is used by a practitioner of skill in the art to detect sepsis or to indicate an increased likelihood of onset of sepsis. In certain embodiments, if the amount in the test subject is below, or substantially below, the threshold reference amount, sepsis is detected, and if the amount in the test subject is above, or substantially above, the threshold reference amount, s sepsis is not detected.

In certain embodiments, the difference between the amount of lysophosphatidylcholine in the test subject and the reference amount correlates inversely with detection of sepsis or with an increased likelihood of onset of sepsis. Such correlation can be determined by those of skill in the art.

When reference amounts from a plurality of reference subjects are used, the evaluation can be based on any statistical technique known to those of skill in the art. Similarly, when a plurality of biomarkers are used, the advanced detection can be based on the plurality of amounts according to techniques known to those of skill in the art, such as those described in U.S. Patent Application Publication Nos. 20030194752, 20040096917, 20040097460, 20040106142, 20040157242, and U.S. Provisional Application Nos. 60/671,620, filed Apr. 15, 2005, 60/671,941, filed Apr. 15, 2005, and 60/674,046, filed Apr. 22, 2005, the contents of which are hereby incorporated by reference in their entireties.

6.9 Reference Amount of Lysophosphatidylcholine

In certain methods of the invention, the amount of lysophosphatidylcholine of the subject is compared to a corresponding reference amount of lysophosphatidylcholine. The reference amount is typically the amount of lysophosphatidylcholine in a reference subject (not the subject of the method) that has, or will have within a defined period of time, a known systemic inflammatory condition. While not intending to be bound by any particular theory of operation, the present invention is based, in part, on the discovery of a correlation between total amount lysophosphatidylcholine and a systemic inflammatory condition in a subject. Accordingly, one practicing a method of the invention can compare the amount of lysophosphatidylcholine in a subject to a reference amount of lysophosphatidylcholine in order to make a prognosis or diagnosis of the systemic inflammatory condition.

In certain methods of the invention, the amount of the lysophosphatidylcholine of the subject is compared to a corresponding reference amount of the lysophosphatidylcholine. The reference amount is typically the amount of the same lysophosphatidylcholine, or a derivative thereof, in a reference subject (not the subject of the method) that has, or will have within a defined period of time, a known systemic inflammatory condition. For example, the reference amount for 1-O-palmitoyl-2-lyso-sn-glycero-3-phosphocholine should be the amount of 1-O-palmitoyl-2-lyso-sn-glycero-3-phosphocholine, or a derivative thereof, in the reference subject. While not intending to be bound by any particular theory of operation, the present invention is based, in part, on the discovery of a correlation between a lysophosphatidylcholine of the invention and advanced detection of sepsis in a subject. Accordingly, one practicing a method of the invention can compare the amount of a lysophosphatidylcholine in a subject to a reference amount of that lysophosphatidylcholine in order to detect sepsis.

Advantageously, in order to practice methods of the invention, one need not gather reference amounts of lysophosphatidylcholine in reference populations. Such reference amounts can be identified in sources available to those of skill in the art, such as public or private databases, or by reference to the data provided herein. As such, in the methods that use a reference amount of lysophosphatidylcholine, one need only make the comparison described in the method.

A reference amount can be measured according to techniques known to those of skill in the art including those described herein. Advantageously, in certain embodiments, the amount of lysophosphatidylcholine in the reference subject and the amount of lysophosphatidylcholine in the test subject are obtained by the same technique.

The reference subject can be any subject that presents, or that will present within a defined period of time, symptoms of the systemic inflammatory condition according to one of skill in the art. In certain embodiments, the reference amount is obtained at a time when the reference subject is presenting the symptoms. In certain embodiments, the reference amount can be obtained at a time before or a time after the reference subject presents symptoms of, or is diagnosed with, the systemic inflammatory condition. For instance, in certain embodiments, reference amounts are obtained from reference subjects 48, 36, 24 or 12 hours prior to onset of sepsis. Those of skill in the art will recognize that such amounts can be obtained by measuring amounts in a reference population diagnosed with sepsis and following the diagnoses of the reference subject at a plurality of time points.

The reference subject can have any systemic inflammatory condition or can be free of a systemic inflammatory condition. In certain embodiments, the reference subject can be SIRS-negative or present symptoms of SIRS, sepsis, severe sepsis, septic shock, multiple organ dysfunction or mortality. Such reference amounts can be used for the advanced detection of the condition.

Methods for the diagnosis of the systemic inflammatory condition are to be carried out according to the knowledge of those of skill in the art. Such methods are routine and will not be described herein.

In certain embodiments, the advanced detection of the systemic inflammatory condition is based on a threshold reference amount. A threshold reference amount is an absolute value for the amount that detects the systemic inflammatory condition. For instance, a threshold reference amount of 100 for a biomarker of the invention can detect sepsis when the test subject has an amount of the biomarker that is less than 100 (or greater than 100 in alternative embodiments). Threshold reference amounts can be determined using statistical techniques known to those of skill in the art based on reference amounts obtained from reference subjects. For instance, a threshold for a particular systemic inflammatory condition can be determined so that a new reference subject can have a advanced detection within a confidence interval suitable to those of skill in the art, for instance with 60%, 70%, 80%, 85%, 90%, 95% or 99% confidence.

6.10 Monitors for the Advanced Detection of Sepsis

The invention also provides monitors that are useful for the advanced detection of sepsis in a subject. In certain embodiments the monitor comprises a sensor module capable of measuring one or more clinical markers of the subject and a chemistry module capable of measuring an amount of lysophosphatidylcholine in fluid or tissue of the subject.

In particular embodiments, the sensor module is capable of measuring two or more clinical markers. In preferred embodiments, the sensor module is capable of measuring the subject's temperature and the subject's respiratory rate. In certain embodiments the monitor comprises a first sensor module capable of measuring the subject's temperature, a second sensor module capable of measuring the subject's respiratory rate, and a chemistry module capable of measuring an amount of lysophosphatidylcholine in fluid or tissue of the subject. In particular embodiments, the first sensor module and the second sensor module are capable of being combined into one sensor module.

In certain embodiments the monitor comprises a sensor module that measures one or more clinical markers of the subject and a chemistry module that measures an amount of lysophosphatidylcholine in fluid or tissue of the subject.

In particular embodiments, the sensor module measures two or more clinical markers. In preferred embodiments, the sensor module measures the subject's temperature and the subject's respiratory rate. In certain embodiments the monitor comprises a first sensor module that measures the subject's temperature, a second sensor module that measures the subject's respiratory rate, and a chemistry module that measures an amount of lysophosphatidylcholine in fluid or tissue of the subject. In particular embodiments, the first sensor module and the second sensor module are combined into one sensor module.

In certain embodiments, the monitor is capable of measuring at a single time point. In certain embodiments, the monitor is capable of measurement at a plurality of time points. In certain embodiments, the monitor is capable of measurement at a plurality of time points on demand by the user. In certain embodiments, the monitor is capable of measurement at a plurality of time points at user selected times (e.g., hourly, every eight hours, every twelve hours, daily, etc.). In certain embodiments, the monitor is capable of measurement at a plurality of time points automatically at regular intervals (e.g., every 5 minutes, every 10 minutes, etc.). In certain embodiments, the monitor is capable of measurement at a plurality of time points automatically and continuously.

In certain embodiments, the monitor measures at a single time point. In certain embodiments, the monitor measures at a plurality of time points. In certain embodiments, the monitor measures at a plurality of time points on demand by the user. In certain embodiments, the monitor measures at a plurality of time points at user selected times (e.g., hourly, every eight hours, every twelve hours, daily, etc.). In certain embodiments, the monitor measures at a plurality of time points automatically at regular intervals (e.g., every 5 minutes, every 10 minutes, etc.). In certain embodiments, the monitor measures at a plurality of time points automatically and continuously.

In a preferred embodiment, the monitor is capable of continuous measuring.

In certain embodiments, the individual sensor modules and chemistry modules of the monitor operate separately of one another.

In certain embodiments, the invention provides for a stand-alone monitor capable of measuring at a plurality of time points an amount of lysophosphatidylcholine in fluid or tissues of the subject.

In certain embodiments, the invention provides for a stand-alone monitor that measures lysophosphatidylcholine in fluid or tissues of the subject. In certain embodiments, the invention provides for a stand-alone monitor that measures a plurality of time points an amount of lysophosphatidylcholine in fluid or tissues of the subject.

In certain embodiments, the first sensor module is capable of connecting to a temperature probe in the subject. In particular embodiments, the temperature probe is capable of being applied externally to the subject's skin, for example, it is capable of being secured in place under the subject's arm pit. In particular embodiments, the temperature probe is capable of being applied internally to the subject, for example, it is capable of being applied orally or rectally to the subject. In preferred embodiments, the internal temperature probe is capable of being applied to the subject's esophagus or rectum.

In certain embodiments, the first sensor module is connected to a temperature probe in the subject. In particular embodiments, the temperature probe is applied externally to the subject's skin, for example, it is secured in place under the subject's arm pit. In particular embodiments, the temperature probe is applied internally to the subject, for example, it is applied orally or rectally to the subject. In preferred embodiments, the internal temperature probe is applied to the subject's esophagus or rectum.

In certain embodiments, the second sensor module is capable of being connected to any device suitable for the measurement of respiratory rate in a subject, including a pressure sensor, a humidity sensor, a thermistor or a motion sensor. In certain embodiments, the second sensor module is capable of being connected to a motion sensor. In particular embodiments, the motion sensor is a flow meter. In particular embodiments, the flow meter is in a respirator.

In certain embodiments, the second sensor module is connected to any device suitable for the measurement of respiratory rate in a subject, including a pressure sensor, a humidity sensor, a thermistor or a motion sensor. In certain embodiments, the second sensor module is connected to a motion sensor. In particular embodiments, the motion sensor is a flow meter. In particular embodiments, the flow meter is in a respirator.

In certain embodiments, the chemistry module is capable of contacting a sample from the fluid or tissue of the subject with: an enzyme or reagent capable of reacting lysophosphatidylcholine to form glycerophosphatidylcholine, an enzyme or reagent capable of reacting glycerophosphatidylcholine to form choline, an enzyme or reagent capable of reacting choline, water and oxygen to form peroxide, a peroxidase and a fluorogenic substrate of said peroxidase, under conditions suitable for formation of a fluorescent product wherein the fluorescent product indicates lysophosphatidylcholine.

In certain embodiments, the sample from the fluid or tissue of the subject in the chemistry module is contacted with: an enzyme or reagent capable of reacting lysophosphatidylcholine to form glycerophosphatidylcholine, an enzyme or reagent capable of reacting glycerophosphatidylcholine to form choline, an enzyme or reagent capable of reacting choline, water and oxygen to form peroxide, a peroxidase and a fluorogenic substrate of said peroxidase, under conditions suitable for formation of a fluorescent product wherein the fluorescent product indicates lysophosphatidylcholine.

The monitors of the present invention may contain, as part of the chemistry module, reagents useful for the measurement of lysophosphatidylcholine in the fluid or tissue of the subject. In certain embodiments, the reagents comprise one or more enzymes and one or more substrates useful for detection of lysophosphatidylcholine. In particular embodiments, the chemistry module can comprise a fluorogenic substrate useful for the measurement of lysophosphatidylcholine. Certain chemistry modules comprise an enzyme or reagent capable of reacting lysophosphatidylcholine to form glycerophosphatidylcholine under suitable conditions, an enzyme or reagent capable of reacting glycerophosphatidylcholine to form choline under suitable conditions, an enzyme or reagent capable of reacting choline to form peroxide under suitable conditions, a peroxidase and a fluorogenic substrate of said peroxidase. Certain chemistry modules comprise a lysophospholipase, a glycerophosphatidylcholine diesterase, a choline oxidase, a peroxidase and 10-acetyl-3,7-dihydroxyphenoxazine. Certain chemistry modules comprise EC 3.1.1.5, EC 3.1.4.2, EC 1.1.3.17, horseradish peroxidase and 10-acetyl-3,7-dihydroxyphenoxazine. The chemistry modules can further comprise one or more reference standards for evaluating the total lysophosphatidylcholine according to methods of the invention.

In particular embodiments, the reagents useful for the measurement of lysophosphatidylcholine in the fluid or tissue of the subject are on a test strip in the chemistry module, onto which the sample of fluid or tissue is applied.

In certain embodiments, the monitors further comprise a label or labeling with instructions for carrying out a method of the invention. For example, the label or labeling can provide a reference amount or reference amounts of lysophosphatidylcholine corresponding to one or more systemic inflammatory conditions, such as SIRS, sepsis, severe sepsis, septic shock or multiple organ dysfunction. The label or labeling can provide one or more threshold reference amounts of lysophosphatidylcholine corresponding to one or more of systemic inflammatory condition, or to conversion of one systemic inflammatory condition into another, for example, for conversion of SIRS-positive into sepsis. Further, the label or labeling can provide citations or links to sources of such reference amounts. The label or labeling can also provide reference values for clinical markers, such as temperature and respiratory rate, corresponding to one or more systemic inflammatory conditions. The label or labeling can provide one or more threshold reference values for clinical markers, such as temperature and respiratory rate, corresponding to one or more systemic inflammatory condition, or to conversion of one systemic inflammatory condition into another, for example, for conversion of SIRS-positive into sepsis. Further, the label or labeling can provide citations or links to sources of such reference amounts.

6.11 Systems for the Advanced Detection of Sepsis

The invention also provides systems that are useful for the advanced detection of sepsis in a subject. In certain embodiments the system comprises: (a) one or more monitors of the invention, (b) a computational device capable of combining the measurements obtained from the one of more monitors into a result, and (c) a module capable of storing, displaying and/or transmitting the result. In such systems, the computational device comprises: (i) a device capable of receiving the measurements from the one or more monitors; (ii) a microprocessor with an algorithm capable of combining the measurements into a result; and (iii) a device capable of transmitting the result to the module capable of storing, displaying and/or transmitting.

In certain embodiments the system comprises: (a) one or more monitors of the invention, (b) a computational device that combines the measurements obtained from the one of more monitors into a result, and (c) a module capable of storing, displaying and/or transmitting the result. In such systems, the computational device comprises: (i) a device that receives the measurements from the one or more monitors; (ii) a microprocessor with an algorithm that combines the measurements into a result; and (iii) a device that transmits the result to the module capable of storing, displaying and/or transmitting.

In certain embodiments, the system comprises a single sensor module capable of measuring one or more clinical markers of the subject. In such systems, the computational device is capable of combining into a result the clinical marker values from the sensor module and any lysophosphatidycholine and/or biomarker values obtained independently from a laboratory to which the fluid or tissue samples of the subject have been sent for analysis. FIG. 1 illustrates this embodiment of the system.

In certain embodiments, the system comprises a single sensor module that measures one or more clinical markers of the subject. In such systems, the computational device combines into a result the clinical marker values from the sensor module and any lysophosphatidycholine and/or biomarker values obtained independently from a laboratory to which the fluid or tissue samples of the subject have been sent for analysis. FIG. 1 illustrates this embodiment of the system.

In certain embodiments, the system comprises a sensor module capable of measuring one or more clinical markers of the subject and a chemistry module capable of measuring an amount of lysophosphatidylcholine in fluid or tissue of the subject. In such embodiments, the computational device is capable of combining the clinical marker and lysophosphatidylcholine measurements from the modules into a result.

In certain embodiments, the system comprises a sensor module that measures one or more clinical markers of the subject and a chemistry module that measures an amount of lysophosphatidylcholine in fluid or tissue of the subject. In such embodiments, the computational device combines the clinical marker and lysophosphatidylcholine measurements from the modules into a result.

In certain embodiments, the system comprises a first sensor module capable of measuring the temperature of the subject, a second sensor module capable of measuring the respiratory rate of the subject, and a chemistry module capable of measuring an amount of lysophosphatidylcholine in fluid or tissue of the subject. In such embodiments, the computational device is capable of combining the temperature, respiratory rate, and lysophosphatidylcholine measurements from the modules into a result.

In certain embodiments, the system comprises a first sensor module that measures the temperature of the subject, a second sensor module that measures the respiratory rate of the subject, and a chemistry module that measures an amount of lysophosphatidylcholine in fluid or tissue of the subject. In such embodiments, the computational device combines the temperature, respiratory rate, and lysophosphatidylcholine measurements from the modules into a result.

In certain embodiments, the system additionally comprises a second chemistry module capable of measuring a second biomarker in fluid or tissue of the subject. In such an embodiment, the computational device is capable of combining the temperature, respiratory rate, lysophosphatidylcholine, and second biomarker values into a result.

In certain embodiments, the system additionally comprises a second chemistry module that measures a second biomarker in fluid or tissue of the subject. In such an embodiment, the computational device combines the temperature, respiratory rate, lysophosphatidylcholine, and second biomarker values into a result.

In certain aspects, the invention provides systems for the advanced detection of sepsis in a subject comprising: (a) a sensor module capable of measuring at a plurality of time points one or more clinical markers of the subject, (b) a chemistry module capable of measuring at a plurality of time points an amount of lysophosphatidylcholine or procalcitonin in fluid or tissue of the subject, (c) a computational device capable of combining the measurements in (a) and the measurements in (b) into a result, comprising: (i) a device capable of receiving the measurements in (a) and the measurements in (b) from the one or more modules; (ii) a microprocessor with an algorithm capable of combining the measurements into a result; and (iii) a device capable of transmitting the result to a module capable of storing, displaying and/or transmitting; and (d) a module capable of storing, displaying or transmitting the result.

In certain aspects, the invention provides systems for the advanced detection of sepsis in a subject comprising: (a) a sensor module that measures at a plurality of time points one or more clinical markers of the subject, (b) a chemistry module that measures at a plurality of time points an amount of lysophosphatidylcholine or procalcitonin in fluid or tissue of the subject, (c) a computational device that combines the measurements in (a) and the measurements in (b) into a result, comprising: (i) a device that receives the measurements in (a) and the measurements in (b) from the one or more modules; (ii) a microprocessor with an algorithm that combines the measurements into a result; and (iii) a device that transmits the result to a module that stores, displays and/or transmits; and (d) a module that stores, displays or transmits the result.

In certain embodiments, the monitors are capable of measuring at a single time point. In certain embodiments, the monitors are capable of measurement at a plurality of time points. In certain embodiments, the monitors are capable of measurement at a plurality of time points on demand by the user. In certain embodiments, the monitors are capable of measurement at a plurality of time points at user selected times (e.g., hourly, every eight hours, every twelve hours, daily, etc.). In certain embodiments, the monitors are capable of measurement at a plurality of time points automatically at regular intervals (e.g., every 5 minutes, every 10 minutes, etc.). In certain embodiments, the monitors are capable of measurement at a plurality of time points automatically and continuously.

In certain embodiments, the monitors measure at a single time point. In certain embodiments, the monitors measure at a plurality of time points. In certain embodiments, the monitors measure at a plurality of time points on demand by the user. In certain embodiments, the monitors measure at a plurality of time points at user selected times (e.g., hourly, every eight hours, every twelve hours, daily, etc.). In certain embodiments, the monitors measure at a plurality of time points automatically at regular intervals (e.g., every 5 minutes, every 10 minutes, etc.). In certain embodiments, the monitors measure at a plurality of time points automatically and continuously.

It will also be apparent to one of skill in the art that clinical marker values can be stored and used in numerous ways. For example, the clinical marker values can be stored as integrated values, maximum or minimum values, as measurements at specific time intervals, or as instantaneous readings.

The result displayed by the systems of the invention can be indicative of status of the subject. In certain embodiments, the result is a number that indicates sepsis. For example, the number may be indexed from 1-100, wherein "100" indicates sepsis. In certain embodiments, the result is a "yes/no" signal, wherein "yes" indicates sepsis. In certain embodiments, the result is displayed on a screen. In certain embodiments, the result is transmitted to the medical record of the subject.

In certain embodiments, the computational device is further capable of comparing the amount of lysophosphatidylcholine in the subject to a reference amount indicative of the amounts of lysophosphatidylcholine in fluids or tissues of a plurality of individuals that have, or will have, sepsis. In particular embodiments, the reference amount is the amount measured in a SIRS-positive individual 0, 12, 24, 36 or 48 hours prior to onset of sepsis. In certain embodiments, the computational device compares the amount of lysophosphatidylcholine in the subject to the reference amount, prior to combining the clinical marker, lysophosphatidylcholine, and/or second biomarker values into a result indicative of the status of the subject.

6.12 Algorithms for the Advanced Detection of Sepsis

The present invention provides lysophosphatidylcholine, clinical markers, and biomarkers useful for the advanced detection of sepsis in a subject. In this section and the sections that follow, unless specified otherwise, the term "markers" refers to the lysophosphatidylcholine, clinical markers, and biomarkers of the invention. Additionally, in this section and the sections that follow, unless specified otherwise, the term "marker values" refers to the lysophosphatidylcholine, clinical marker and biomarker values made at any given time point for the subject. These markers and their marker values can be used to detect sepsis in the subject, by determining the probability of sepsis.

The marker values can be used to develop an algorithm, or plurality of algorithms, that discriminate between a SIRS subject that will convert to sepsis ("converter") and a SIRS subject that will not convert to sepsis ("nonconverter"). Typically, a SIRS subject is considered a nonconverter when the subject does not develop sepsis in a defined time period (e.g., observation period). This defined time period can be, for example, twelve hours, twenty four hours, forty-eight hours, a day, a week, a month, or longer. Specific algorithms that discriminate between subjects that develop sepsis and subjects that do not develop sepsis during a defined period will be described in the subsections below. Once an algorithm has been built using these exemplary data analysis algorithms or other techniques known in the art, the algorithm can be used to classify a test subject into one of the two or more phenotypic classes (e.g., a converter or a nonconverter, SIRS-positive or sepsis). This is accomplished by applying the algorithm to a marker values obtained from the test subject. Such algorithms, therefore, have value as diagnostic indicators.

The present invention provides, in one aspect, for comparison of marker values from a test subject to marker values obtained from a training population. In some embodiments, this comparison is accomplished by (i) fitting an algorithm using the marker values from the training population to produce a fitted-algorithm and (ii) applying the algorithm to the marker values from the test subject. As such, the algorithms applied in some embodiments of the present invention are used to calculate the probability of sepsis in a SIRS subject. In preferred embodiments of the invention, the algorithms are used to calculate the probability of sepsis in a SIRS-positive subject.

In certain embodiments, an the algorithm is any mathematical model known by those of skill in the art.

In certain embodiments, the algorithm is a statistical model.

In certain embodiments, the algorithm calculates the probability of sepsis.

In particular embodiments, the probability of sepsis in the subject is made as a call of "sepsis" for the subject. In particular embodiments, the probability of sepsis in the subject is made as a classification of the subject as a "sepsis" subject.

In some embodiments of the present invention, when the results of an application of an algorithm indicate that the subject has a high probability of sepsis, the subject is classified as a "sepsis" subject. If the results of an application of an algorithm indicate that the subject has a low probability of sepsis, the subject is classified as a "SIRS" subject. Thus, in some embodiments, the result in the above-described binary decision situation has four possible outcomes:

(i) truly septic, where the algorithm indicates that the subject will acquire sepsis and the subject does in fact acquire sepsis during the definite time period (true positive, TP);

(ii) falsely septic, where the algorithm indicates that the subject will acquire sepsis and the subject, in fact, does not acquire sepsis during the definite time period (false positive, FP);

(iii) truly SIRS, where the algorithm indicates that the subject will not acquire sepsis and the subject, in fact, does not acquire sepsis during the definite time period (true negative, TN); or (iv) falsely SIRS, where the algorithm indicates that the subject will not acquire sepsis and the subject, in fact, does acquire sepsis during the definite time period (false negative, FN).

It will be appreciated that other definitions for TP, FP, TN, FN can be made. For example, TP could have been defined as instances where the algorithm indicates that the subject will not acquire sepsis and the subject, in fact, does not acquire sepsis during the definite time period. While all such alternative definitions are within the scope of the present invention, for ease of understanding the present invention, the definitions for TP, FP, TN, and FN given by definitions (i) through (iv) above will be used herein, unless otherwise stated.

As will be appreciated by those of skill in the art, a number of quantitative criteria can be used to communicate the performance of the comparisons made between a test marker values and reference marker values (e.g., the application of the algorithm to the marker values of a test subject). These include positive predicted value (PPV), negative predicted value (NPV), specificity, sensitivity, accuracy, and certainty. In addition, other constructs such a receiver operator curves (ROC) can be used to evaluate algorithm performance. As used herein:

PPV=TP/(TP+FP)
NPV=TN/(TN+FN)
specificity=TN/(TN+FP)
sensitivity=TP/(TP+FN)
accuracy=certainty=(TN+TP)/N Here, N is the number of samples compared (e.g., the number of test samples for which a determination of sepsis or SIRS is sought). For example, consider the case in which there are ten subjects for which SIRS/sepsis classification is sought. Marker values are constructed for each of the ten test subjects. Then, each of the marker values is evaluated by applying an algorithm, where the algorithm was developed based upon marker values obtained from a training population. In this example, N, from the above equations, is equal to 10. Typically, N is a number of samples, where each sample was collected from a different member of a population. This population can, in fact, be of two different types. In one type, the population comprises subjects whose samples and phenotypic data (e.g., marker values and an indication of whether or not the subject acquired sepsis) was used to construct or refine an algorithm. Such a population is referred to herein as a training population. In the other type, the population comprises subjects that were not used to construct the algorithm. Such a population is referred to herein as a validation population. Unless otherwise stated, the population represented by N is either exclusively a training population or exclusively a validation population, as opposed to a mixture of the two population types. It will be appreciated that scores such as accuracy will be higher (closer to unity) when they are based on a training population as opposed to a validation population. Nevertheless, unless otherwise explicitly stated herein, all criteria used to assess the performance of an algorithm (or other forms of evaluation of a marker value from a test subject) including certainty (accuracy) refer to criteria that were measured by applying the algorithm corresponding to the criteria to either a training population or a validation population. Furthermore, the definitions for PPV, NPV, specificity, sensitivity, and accuracy defined above can also be found in Draghici, *Data Analysis Tools for DNA Microanalysis,* 2003, CRC Press LLC, Boca Raton, Fla., pp. 342-343, which is hereby incorporated by reference.

In some embodiments the training population comprises nonconverters and converters. In some embodiments, marker values are constructed from this population using biological samples collected from the training population at some time period prior to the conversion to sepsis by the converters of the population. As such, for the converters of the training population, a biological sample can be collected two week before, one week before, four days before, three days before, one day before, or any other time period prior to converters became septic. In practice, such collections are obtained by collecting a biological sample at regular time intervals after admittance into the hospital with a SIRS diagnosis. For example, in one approach, subjects who have been diagnosed with SIRS in a hospital are used as a training population. Once admitted to the hospital with SIRS, the biological samples are collected from the subjects at selected times (e.g., hourly, every eight hours, every twelve hours, daily, etc.). A portion of the subjects acquire sepsis and a portion of the subjects do not acquire sepsis. For the subjects that acquire sepsis, the biological sample taken from the subjects just prior to the conversion to sepsis are termed the $T_{-12}$ biological samples. All other biological samples from the subjects are retroactively indexed relative to these biological samples. For instance, when a biological sample has been taken from a subject on a daily basis, the biological sample taken the day prior to $T_{-12}$ sample is referred to as the $T_{-36}$ biological sample. Time points for biological samples for a nonconverter in the training population are identified by "time-matching" the nonconverter subject with a converter subject. To illustrate, consider the case in which a subject in the training population became clinically-defined as septic on his sixth day of enrollment. For the sake of illustration, for this subject, $T_{-36}$ is day four of the study, and the $T_{-36}$ biological sample is the biological sample that was obtained on day four of the study. Likewise, $T_{-36}$ for the matched nonconverter subject is deemed to be day four of the study on this paired nonconverter subject.

In some embodiments, N is more than one, more than five, more than ten, more than twenty, between ten and 100, more than 100, or less than 1000 subjects. An algorithm (or other forms of comparison) can have at least about 99% certainty, or even more, in some embodiments, against a training population or a validation population. In other embodiments, the certainty is at least about 97%, at least about 95%, at least about 90%, at least about 85%, at least about 80%, at least about 75%, or at least about 70% against a training population or a validation population. The useful degree of certainty may vary, depending on the particular method of the present invention. As used herein, "certainty" means "accuracy." In one embodiment, the sensitivity and/or specificity is at is at least about 97%, at least about 95%, at least about 90%, at least about 85%, at least about 80%, at least about 75%, or at least about 70% against a training population or a validation population. The number of marker values that may be used by an algorithm to classify a test subject with adequate certainty is typically about four. Depending on the degree of certainty sought, however, the number of marker values used in an algorithm can be more less, but in all cases is at least two. In one embodiment, the number of marker values that may be used by an algorithm to classify a test subject is optimized to allow a classification of a test subject with high certainty.

In the examples below, marker data was collected for a plurality of markers in each subject over a time trajectory. That is, for each marker (lysophosphatidylcholine, clinical marker or biomarker), an amount or value was measured at a plurality of time points. Algorithms were fitted from such marker values from a training population using data analysis algorithms in order to determine, and predictive accuracy of conversion of the subject from SIRS to sepsis. While new classification and statistical tools are constantly being developed, the existing body of pattern recognition and prediction algorithms provide effective data analysis algorithms for constructing algorithms. See, for example, National Research Council; Panel on Discriminant Analysis Classification and Clustering, Discriminant Analysis and Clustering, Washington, D.C.: National Academy Press, which is hereby incorporated by reference. Furthermore, the techniques described in Dudoit et al., 2002, "Comparison of discrimination methods for the classification of tumors using gene expression data." JASA 97; 77-87, hereby incorporated by reference in its entirety, can be used to develop such algorithms.

Relevant statistical models for developing an algorithm include, but are not limited to, discriminant analysis including linear, logistic, and more flexible discrimination techniques (see, e.g., Gnanadesikan, 1977, *Methods for Statistical Data Analysis of Multivariate Observations*, New York: Wiley 1977, which is hereby incorporated by reference in its entirety); tree-based algorithms such as classification and regression trees (CART) and variants (see, e.g., Breiman, 1984, *Classification and Regression Trees*, Belmont, Calif.: Wadsworth International Group, which is hereby incorporated by reference in its entirety, as well as Section 5.1.3, below); generalized additive models (see, e.g., Tibshirani, 1990, *Generalized Additive Models*, London: Chapman and Hall, which is hereby incorporated by reference in its entirety); and neural networks (see, e.g., *Neal*, 1996, *Bayesian Learning for Neural Networks*, New York: Springer-Verlag; Ripley, 1996, *Pattern Recognition and Neural Networks*, Cambridge University Press; and Insua, 1998, Feedforward neural networks for nonparametric regression In: *Practical Nonparametric and Semiparametric Bayesian Statistics*, pp. 181-194, New York: Springer, which is hereby incorporated by reference in its entirety).

In one embodiment, comparison of a test subject's marker value to a marker value obtained from a training population is performed, and comprises applying an algorithm. The algorithm is constructed using a data analysis algorithm, such as a statistical model. Other suitable data analysis algorithms for constructing algorithms include, but are not limited to, linear combinations (see Section 5.12.1, below) and longitudinal models (see Section 15.12.3, below). The algorithm can be based upon two, three, four, five, 10, 20 or more features, corresponding to measured observables from one, two, three, four, five, 10, 20 or more markers. The algorithm predicts membership within a population (or class) with an accuracy of at least about at least about 70%, of at least about 75%, of at least about 80%, of at least about 85%, of at least about 90%, of at least about 95%, of at least about 97%, of at least about 98%, of at least about 99%, or about 100%.

Suitable data analysis algorithms are known in the art. In a some embodiments, the algorithm of the invention comprises Linear Combinations (Section 5.12.1, below), Longitudinal Models (Section 5.12.2, below), or Linear Combinations Through Direct Search (Section 5.12.3, below). In specific embodiments, the algorithm of the invention is comprised of Bayes' Theorem (Section 5.12.2.1, below), Bayesian Statistical Analysis (Section 5.12.2.1.1, below), or a hidden Markov model (HMM; Section 5.12.2.2, below). While such algorithms may be used to construct an algorithm and/or increase the speed and efficiency of the application of the algorithm and to avoid investigator bias, one of ordinary skill in the art will realize that computer-based algorithms are not required to carry out the methods of the present invention.

6.12.1. Linear Combinations

A logistic regression algorithm provides one approach for combining the marker values into a result indicative of sepsis. The logistic regression algorithm orders the marker values into linear combinations of marker values, which can then be combined into a single number or index.

For example, for coefficient vector $$l = \begin{bmatrix} 1 \\ c_1 \\ c_2 \\ \vdots \\ c_P \end{bmatrix}$$

and vector of marker values, $$x = \begin{bmatrix} 1 \\ x_1 \\ x_2 \\ \vdots \\ x_P \end{bmatrix},$$

the linear combination defined by l is $$\text{Index} = l^T x = \Sigma_i c_i x_i.$$

Here $c_0$ and $x_0 = 1$ allows for an intercept term, i.e., a value for the linear combination when all the marker values are zero.

Thus, the linear combination allows for the combining of multiple pieces of information, for example, marker values, into a single number or index, in a simple, smooth way. The coefficients may be thought of as weight terms in the index.

It will be appreciated by those of skill in the art that if a single marker is involved, no linear combination is required.

In certain embodiments of the invention, a systemic inflammatory condition can be detected in a subject if the subject's index surpasses the threshold (see Section 5.12.5, below) for that condition. In particular embodiments of the invention, sepsis can be detected in a SIRS-positive subject if the SIRS-positive subject's index surpasses the sepsis threshold. The threshold can be selected in order to provide a balance between sensitivity and specificity.

It will be appreciated by those of skill in the art that the linear combination can be developed from training data in several ways. The training data from multiple days and patient could simply be regarded as statistically independent, and fit to a logistic regression model. The logistic regression model fits probabilities of binary outcomes, for example, a SIRS or sepsis outcome. Specific time points may also be ignored, such as the first available time point. Further, estimated predicted performance may be used to guide the choice of time points to use. Predictive performance estimates can be obtained by cross-validation (see Section 5.12.4, below), some other re-sampling method, or performance on an independent data set, or any other method known to those of skill in the art.

It will be appreciated by those of skill in the art that identification of a linear combination can also be made more directly, avoiding the need to align time points for SIRS and sepsis training populations, by using a three-step process. The first step involves development of a set or series of linear combinations which are applied to each subject and each time point. Application of these linear combinations to the subject's data generates a sequence of numbers (at a plurality of time points) for each subject. The second step involves application of a "functional" to each series, such as a maximum value. The third step involves assessment of the linear combination with regard to how well it separates SIRS subjects from sepsis subjects. In a preferred embodiment, assessment of the linear combination is made with regard to how well it separates SIRS-positive subjects from sepsis subjects. Generic measures of goodness of separation may be determined using Bayesian Information Criterion or Schwartz Information Criterion (BIC; see, e.g., McQuarrie, A. D. R., and Tsai, C.-L., 1998. *Regression and Time Series Model Selection*. World Scientific; and Schwarz, G., 1978, "Estimating the dimension of a model," *Annals of Statistics* 6(2):461-464, which are hereby incorporated by reference in their entireties), Area Under the Curve (AUC), or any other method known to those of skill in the art. The three-step process if repeated for each linear combination in and the measures of goodness of separation are compared until the linear combination is selected that yields the best separation score.

It will be appreciated by those of skill in the art that in practice the sequence of linear combinations can be generated adaptively, as part of a numerical optimization procedure. In certain embodiments of the invention, the numerical optimization procedure is an optimization algorithm. In particular embodiments, the numerical optimization procedure is Simultaneous Perturbation Stochastic Approximation (see, e.g., Spall, J. C. (1999), "Stochastic Optimization: Stochastic Approximation and Simulated Annealing," in *Encyclopedia of Electrical and Electronics Engineering* (J. G. Webster, ed.), Wiley, New York, vol. 20, pp. 529-542, which is hereby incorporated by reference in its entirety).

It will be appreciated by those of skill in the art that regardless of how the linear combination is selected, future statistical performance, as assessed by sensitivity and specificity, can be estimated from training data using cross-validation and other re-sampling approaches. Alternatively, one of skill in the art would understand that future statistical performance can be based on a single independent data set.

6.12.1.1 Extending Linear Combinations

It will appreciated by those of skill in the art that extending the linear combination algorithm can accommodate markers that may not exhibit linear behavior. If information is discrete with two levels, such as gender, an additional marker $x_i$ may be used. For example, $x_i$ may be set to 1 for cases with one level (say, male) and $x_i$ may be set to 0 for otherwise (female). The marker $x_i$ is referred to as an indicator variable. The other level, $x_i=0$ is considered the baseline. The corresponding coefficient, $c_i$, for marker $x_i$ will then be the basis for additional risk accruing to males. Alternatively, if $c_i$ is negative, the risk may be decreased. If information is discrete with more than two levels, one level can be selected arbitrarily as a baseline case, and multiple indicators can be used to indicate the level for a given subject. The additional markers may take on values of 0 and 1, but only one marker can be 1 for any individual subject.

It will be appreciated by those of skill in the art that a nonlinear marker can also be derived from linear marker. For example, the marker can be the square of the linear marker value, allowing for a quadratic response in that particular marker. The derived marker can also be the slope of a linear trend in marker values calculated from the last available three days, for example, or the change from the first available value or any available value.

It will be appreciated by those of skill in the art that adding an indicator for specific time points provides for model flexibility to adapt to different circumstances. For example, adding an indicator that is 1 for observations that are within two days of major surgery allows for a corresponding coefficient that contributes to the model, effectively raising or lowering the threshold for the affected time points.

6.12.1.2 Positive Attributes of Linear Combinations

It will be appreciated by one of skill in the art that linear combination algorithms can display positive attributes with regard to detecting conversion from SIRS to sepsis in a subject. If marker values are distributed in p-dimensional space, then the set of marker values giving the same assay value fall on a plane embedded in this space. If an assumption is made that the sepsis and SIRS data clouds are elliptical and similarly-shaped (i.e., having equal covariance matrices), then the optimal boundary is a hyperplane separating the sepsis and SIRS data points. In certain embodiments of the invention, the optimal boundary is a hyperplane separating SIRS and sepsis data points. In a preferred embodiment of the invention, the optimal boundary is a hyperplane separating SIRS-positive and sepsis data points.

6.12.1.3 Alternatives to Linear Combinations

It will be appreciated by those of skill in the art that there are various alternatives to linear combinations.

For example, one alternative to linear combinations is to apply individual thresholds to each marker value, and then fit algorithms based on combinations of positive and negative results.

Other alternatives to linear combinations include boundaries developed from quadratic discriminant functions, arising when data clouds are elliptical, but having different shapes, or covariance matrices, and boundaries derived from semiparametric classification models such as neural nets, support vector machines, gradient boosting machines, or tree-based classifiers.

A person of skill in the art will appreciate that a complication that arises when subjects are monitoring at a plurality of time points is that multiple data points arise from the same subject, but from different days. The classification of the subject as SIRS-negative, SIRS-positive, septic, etc., could conceivably be based on the subject's trajectories. However, an additional complication is that the subject's trajectories do not have a fixed number of days.

The approaches illustrated in the Examples below address the problem of multiple days per subject include a linear logistic regression approach and two related longitudinal approaches. A possible third approach is based on hidden Markov models (HMMs), which are the current state of the art in voice recognition.

6.12.1.4 Fitting Linear Combinations

6.12.1.4.1 Linear Logistic Regression

Linear logistic regression is one way to estimate a linear combination from data. A linear logistic regression model is of the form $$\ln\left(\frac{p}{1-p}\right) = c_0 + c_1 x_1 + \ldots + c_p x_p = l^T x$$

where p is the probability of sepsis. This resembles standard linear regression except it replaces the response with a log ratio. The log ratio, called the logistic function, transforms values falling anywhere on the real line to values between zero and one, which can therefore be interpreted as probabilities. A model is fitted (by maximum likelihood, the current standard in statistics) by taking the observed x values and finding the coefficients c that make the observed data most likely.

It will be appreciated by those of skill in the art that in the simplest incarnation of the logistic regression approach to the sepsis monitoring problem, the daily nature of the data, as well as the fact that multiple days arise from the same subject, is ignored. All observations are labeled as arising from a SIRS subject or from a sepsis subject, and are fit a logistic regression model. While this approach ignores key variables, a person of skill in the art would nevertheless recognize that the approach succeeds in identifying a linear combination that gives useful marker weights for an index.

6.12.2. Longitudinal Models

The use of longitudinal models provides another approach for combining the marker values into a result indicative of sepsis. A longitudinal model takes time into account by fitting a function over discreet time points. Linear longitudinal models can be evaluated by assuming that the different marker values measured for a subject arise from a linear trend, on which is superimposed random or Gaussian noise. Consequently, measurements for different markers on the same day for the same subject can be correlated. Moreover, linear longitudinal models can also be hierarchical. For example, there can be a population-average time trend per marker for sepsis subjects and a population-average time trend per marker for SIRS subjects, giving rise to classification of the linear longitudinal model as either SIRS or sepsis. Within these two populations, time trends per marker may vary from subject to subject.

A person of skill in the art will recognize that varying trajectory lengths complicate longitudinal modeling. For long trajectories, an assumption of steady linear trend becomes less and less reasonable, for example, if a plateau is reached. Alternatively, a local linear fit to a moving window of points can be used. That is, once a maximum number of points is reached, the oldest point is dropped when a new point is measured. The moving window approach is not ideal because the data dropped is not modeled, raising some risk that a phenomenon at early time points will not be appropriately accounted for.

6.12.2.1 Class Probabilities Using Bayes' Theorem

It will be appreciated by one of skill in the art that a consequence of the different population-average time trends per marker for sepsis subjects versus SIRS subjects is that there is one model for sepsis subjects and another model for SIRS subjects. Therefore, given a data trajectory from a new subject, classification of the subject as SIRS or sepsis may proceed according to which model better fits the observed data.

Classification of the subject is made by applying Bayes' Theorem to generate a group probability derived from the ratio of model likelihoods and from prevalence and other prior information. For example, in its simplest form, Bayes' Theorem allows for probability inversion:

$$P(\text{Sepsis} \mid \text{Data}) = \frac{P(\text{Data} \mid \text{Spesis}) P(\text{Sepsis})}{P(\text{Data})}$$

or, more completely, $$P(\text{Sepsis} \mid \text{Data}) = \frac{P(\text{Data} \mid \text{Spesis}) P(\text{Sepsis})}{P(\text{Data} \mid \text{Sepsis}) P(\text{Sepsis}) + P(\text{Data} \mid \text{SIRS}) P(\text{SIRS})}$$

where "|" is read "given" or "conditional on."

It will be appreciated by those of skill in the art that the above calculation can be performed in a number of ways. One way is to estimate model parameters from available training data, which defines the models $P(\text{Data} \mid \text{Sepsis})$ and $P(\text{Data} \mid \text{SIRS})$ Then Bayes' theorem can be applied by entering observed new data into the fitted models. In certain embodiments, the fitted models are for SIRS and sepsis. In a preferred embodiment, the fitted models are for SIRS-positive and sepsis.

6.12.2.1.1 Bayesian Statistical Analysis

An improvement on the above approach is to use Bayes' theorem to obtain probability distributions for the sepsis and SIRS model parameters, which incorporates the uncertainty in the model parameters given the superimposed random noise inherent in the training data. This approach is referred to as Bayesian statistical analysis (see, e.g., Lee, Peter M., 1997, *Bayesian Statistics: An Introduction*, Third Edition, Oxford Press, which is hereby incorporated by reference in its entirety) quite apart from the use of Bayes' Theorem to make the original classification.

In certain embodiments of the invention, a three-step Bayesian statistical analysis is used to calculate probability of sepsis. First, probably distributions are made for the sepsis and SIRS model parameters. Second, thousands of random draws of parameters are taken from these distributions which give rise to thousands of models, in turn giving rise to thousands of possible values for P(Sepsis|Observed data). Third, the probabilities are averaged to obtain a single probability of sepsis.

It will be appreciated by those of skill in the art that in practice the random generation of model parameters is made by Markov chain Monte Carlo methods typically used in Bayesian analysis.

6.12.2.2 Stochastic Process Approaches

As described above, standard longitudinal model methods are not ideal for prediction in the monitoring setting, where trajectory lengths can vary. Alternative approaches are available in the art.

A person of skill in the art will know that one alternative is hidden Markov models, a type of discrete stochastic process. A discrete stochastic process has a set of time points, typically equally spaced, proceeding into the indefinite future. The process proceeds over these time points, taking on a state of being at each time point. The state could be selected from a finite set of possible states, or could fall on a continuum or even a plane or a higher-dimensional space. When the process is at iteration i, its location or state at iteration i+1 is selected randomly, but the probability depends on where the process is and has been. A stochastic process is Markov when the probability its state at iteration i+1 depends only on its state at iteration i. In other words, where it may go on its next step depends only on where it is now; it is memory-less and does not exhibit momentum or other mechanisms which incorporate the past. A random walk is an example of a Markov stochastic process.

A hidden Markov model (HMM) is a model in which the process takes on different states via a Markov process, yet the states are not themselves observed. Rather, data is observed, and each state manifests a different distribution of data. Therefore, it is possible to infer the change in state due to the change in the data observed.

Fitting a HMM entails estimating the parameters of the Markov chain probabilities of transitioning between states, the probability distribution of the initial state, and the data distributions corresponding to the different states. A determination of the likely number of different hidden states may be made by balancing sampling rate or sample number against quality of model fit.

The hidden states are selected to fit the data. For example, one state may represent infection in a sepsis subject. Another state may represent a SIRS-positive state. As a subject converts from one state to another (for example, SIRS-positive to sepsis, or SIRS-positive to SIRS-negative), the conversion may be modeled as the algorithm moving through several discrete states.

Identification of sepsis using HMM may be accomplished in several ways. In certain embodiments of the invention, the training data from known sepsis and SIRS subjects is fit to a single HMM, provided the number of hidden states and transition probabilities sufficient to accommodate both populations. By fitting the training data to a single HMM, and then applying that fitted HMM to marker value measured at a plurality of time points for a test subject, an estimate of the most likely states for that subject at each time point may be made. This estimate can allow an identification of those specific states which indicate conversion to sepsis at any particular time point. If any of the identified states at any of the time points are associated with sepsis, and if the states are sufficiently likely, a determination that the subject has converted or is likely to convert to sepsis can be made.

In certain embodiments of the invention, the training data is fit to two HMMs, one HMM to known sepsis subjects and the other HMM to known SIRS subjects. Both fitted HMMs can be applied to the marker values measured at a plurality of time points for the test subject, and a determination made as to whether the sepsis HMM explains the subject's time series better than the SIRS HMM. Probabilities can be developed as with the longitudinal models described above.

It will be appreciated by those of skill in the art that HMMs may be fitted using maximum likelihood methods or with Bayesian methods. In a preferred embodiment of the invention, the Bayesian approach is preferred. In addition to allowing for uncertainty in the model parameters, Bayesian models typically can handle many parameters without overfitting, in part by applying shrinkage of parameters to common values.

It will be appreciated by those of skill in the art that aspects of data distributions, such as variance, for different hidden states may be similar. Those of skill in the art will understand that optimization of the model can be achieved by shrinking variances towards one another, or by enforcing a common variance (while allowing means to shift).

6.12.3. Linear Combinations Through Direct Search

Another alternative to longitudinal models is to search directly for a linear combination that discriminates sepsis from SIRS over entire trajectories. Numerical search procedures can be used, which generate a series of candidate linear combinations, $l_m$.

It will be appreciated by one of skill in the art that analysis can take a four-step approach. First, given a candidate $l_m$, $$l_m^T x_{ij}$$

is calculated, where $x_{ij}$ is the data vector for subject j on day i. Second, for each subject j, the maximum $x_i$ is taken across days. This yields a single number per subject, no matter how many days or how much data per day is available. Third, the candidate $l_m$ is scored according to how well these numbers separate as sepsis or SIRS. The score can be area under the ROC curve or any typical model-comparison metric, such as An Information Criterion or Akaike Information Criterion (AIC; see, e.g., Akaike, H., 1974, "A new look at the statistical model identification," *IEEE Transactions on Automatic Control* 19 (6): 716-723, which is hereby incorporated by reference in its entirety) or BIC, or any other method known to those of skill in the art. Fourth, the candidate $l_m$ which gives the best score is selected.

It will be appreciated by those of skill in the art that taking a maximum is one example of a "functional" applied to trajectories. The motivation for selecting the maximum is that a physician should take action the first time the linear combination exceeds some threshold, so if the maximum is above the threshold, a determination that the subject has converted or is likely to convert to sepsis can be made.

Other functionals can also be considered, and are known to those of skill in the art. For example, since the maximum is prone to outliers, taking the second-highest point may be more robust, while yielding a similar linear combination. Standard logistic regression approximately corresponds to taking the average rather than the maximum.

It will be appreciated by those of skill in the art that many different numeric search strategies could be equally applied to the algorithms of this invention. In a preferred embodiment, the Simultaneous Perturbation Stochastic Approximation is used.

6.12.4. Cross-Validation

Cross-validation is a method of estimating predictive performance that proceeds by leaving out a fraction of the data, fitting a model, predicting the left-out fraction, and assessing the quality of that prediction. With regard to classification, for example, the estimate of predictive performance can be overall accuracy, likelihood ratio (true positive rate/false positive rate), area under the receiver operating characteristic (ROC) curve, or area under the ROC curve in the neighborhood of the target specificity.

Cross-validation may be applied to a number of different models and/or modeling parameters to determine which gives better estimated performance, thereby guiding modeling strategy. Once the optimal modeling strategy is determined, a final model can be fitted with all the available data.

Preferably, the left-out fraction is small so that the data used for training is close in size to the total available training data set. An optimal left-out fraction is 10% of the total available training data set. For example, if there are 100 available data points, it is preferred that the left-out fraction is be 10%, leaving 90 data points for training.

There are several types of cross-validation known to those of skill in the art. For example, one common type is "k-fold" cross-validation. In this type of cross-validation, the training data set is partitioned into k approximately equal sets. Each set is left out in turn, for k iterations, and the left-out fraction is 1/k. A value of k=10 is typical.

Another common type of cross-validation known to those of skill in the art is the "leave-one-out" cross-validation. As the name implies, the fraction left out is 1/N where N is the number of available training data points. Each observation is left out in turn.

A less common type of cross-validation known to those of skill in the art as the "out-of-bag" cross-validation. In this type of cross-validation, a randomly-selected set is set aside for one iteration, then returned, another randomly-selected set is selected for the next iteration, then returned, and so on. The fraction is the same across iterations, and the random selection is independent across iterations. There are no constraints on selection from iteration to iteration; a data point could be randomly selected for two iterations in a row, for example, while another data point could be not selected for many iterations. A typically number of iterations used is 400.

6.12.5. Thresholds

Predictive models generate a probability of sepsis. For a single marker, such as lysophosphatidylcholine alone, there is a one-to-one relationship between the marker value and a sepsis probability, so the threshold on probabilities may be translated into a threshold on lysophosphatidylcholine. When the model is based on a linear combination or index of several markers, the threshold on probabilities can be translated into a threshold on index values.

Typically, thresholds are selected to give the desired trade off between sensitivity and specificity, as estimated by cross-validation. In one embodiment of the invention, a threshold is selected for which the specificity estimate is 90%.

6.12.6. Likelihood Ratio and Day-Specific Likelihood Ratio

Likelihood ratio is a measure of diagnostic utility comprised of [(true positive rate)/(false positive rate)], or [(sensitivity)/(1−specificity)]. (See, for example, "Statistical Methods in Diagnostic Medicine," by Xiao-Hua Zhou, Nancy Obuchowski, and Donna McClish, 2002, Wiley, New York). Higher values indicate higher utility.

That the likelihood ratio summarizes the diagnostic information in a test can be seen by a form of Bayes' theorem. In the context of diagnosis, Bayes' theorem can be expressed as:

(odds of disease positive given positive test result)=
(likelihood ratio)×(odds of disease positive), where the odds associated with a probability p is p/(1−p). "Odds of disease positive" ("prior odds" in the language of Bayes' theorem, as they are prior to obtaining data) would typically be based upon prevalence, i.e., (prevalence)/(1−prevalence), although it could alternatively be based on a physician's subjective probability after viewing a patient. "Odds of disease positive given positive test result" is referred to as "posterior odds" in the language of Bayes' theorem. Bayes' theorem indicates that upon first presentation of the patient, there are prior odds of disease positive status. Once the test result is observed, the test result moves the prior odds to posterior odds. The more informative a test, the greater distance it can move prior odds to posterior odds.

In one aspect, estimates are presented as likelihood ratios based on observed rates. If a false-positive rate is observed to be zero, the estimated likelihood ratio is infinite. This is denoted by the mathematical symbol for infinity, "∞." A likelihood ratio estimate that is infinity does not indicate a perfect diagnostic system, of course.

In certain embodiments which can involve monitoring patients over a number of days, a "day-specific likelihood ratio" is one of the more useful means for evaluating the status of the patient. The day-specific likelihood ratio may be viewed in two different ways. To understand the difference, consider a hypothetical patient who is monitored for five days before being diagnosed as septic, and suppose a predictive algorithm makes a positive call on the third day, but on the fourth and fifth days the algorithm does not make positive calls. In a monitoring regimen in which a doctor would act upon the first positive algorithm call, this patient would be considered a true positive, even though the patient was not positive on every day.

One way to construct a day-specific likelihood ratio is to calculate true positive rates and false positive rates for each day according to the regimen. In this case, the hypothetical patient is counted as false negative and decreases the likelihood ratio. On days three through five it contributes to the true positive rate, and increases the likelihood ratio. This is a "cumulative" likelihood ratio because the patient algorithm positivity status accumulates. As time progresses to the moment prior to diagnosis, the cumulative likelihood ratio moves to equal the non-day-specific likelihood ratio, i.e., (sensitivity)/(1−specificity) in which a patient is called positive if it has been called positive on any day.

That is, the cumulative likelihood ratio evaluated on day k is constructed by examining all patients evaluable for day k, and calculating sensitivity and specificity up to day k based on the presence of any positive algorithm call up to or including day k.

Alternatively, a patient's status on a given day may be evaluated solely by the algorithm call for that day. This is a "daily snapshot" likelihood ratio.

For illustration, consider a hypothetical patient who is diagnosed as septic late on the fifth day of monitoring, and suppose the monitor algorithm yielded positive calls on days three and five. According to the cumulative regime, the patient would be called negative on days one and two, and hence would be counted as a false negative, decreasing the cumulative likelihood ratio for those days. On days three, four, and five, this patient is counted as a true positive, and increases the cumulative likelihood ratio for those days.

Alternatively, for the daily snapshot likelihood ratio, this patient is counted as a false negative on days one, two, and four, and decreases the daily snapshot likelihood ratio for those days. He or she is counted as a true positive on days three and five, and increases the snapshot likelihood ratio for those days.

Neither day-specific likelihood ratio fully characterizes the algorithm's performance. Suppose that disease-positive and disease-negative patient populations become well separated late in patients' trajectories, yet efforts to exploit this difference lead to a high false positive rate early in their trajectories. Then the cumulative likelihood ratio could indicate a relatively low measure of utility, correctly indicating that the monitoring problem has not yet been fully solved, yet masking the fact that there is a basis for improved performance if the early-trajectory issue can be resolved. The daily snapshot likelihood ratio could be very high for days late in patients' trajectories, correctly identifying differences between patient populations yet masking the fact that the monitoring problem has not yet been fully solved. By examining both, one can correctly assess both actual clinical utility today and potential for improvements in the future.

6. EXAMPLES

Examples 1-4 demonstrate the utility of the markers of the invention for the advance detection of sepsis. Reference marker data sets were established for two populations of patient volunteers.

Patient Populations

Patients were divided into two populations. The first population ("the SIRS group") represents patients who developed SIRS and who entered into the present study at "Day 1" but who did not progress to sepsis during their hospital stay. The second population ("the sepsis group") represents patients who likewise developed SIRS and entered into the present study at Day 1 but who progressed to sepsis typically at least several days after entering the study.

Sample Collection

Blood samples were taken about every 24 hours from each study group. Clinical suspicion of sepsis in the sepsis group occurred at "time 0." The samples were taken at "time—12 hours", "time—36 hours" and "time—60 hours" preceding the day of clinical suspicion of onset of sepsis in the sepsis group. That is, the samples from the sepsis group included those taken on the day of entry into the study (Day 1), 60 hours prior to clinical suspicion of sepsis (time −60 hours), 36 hours prior to clinical suspicion of sepsis (time −36 hours), and on the day of clinical suspicion of onset of sepsis (time −12 hours).

Measurement of Biomarker Amounts

Biomarker amounts were measured used standard quantitative RT-PCR techniques known to those of skill in the art, which provide quantitative measures of biomarker gene expression levels (see, for example, U.S. Published Application No. 20040106142 A1, the content of which is hereby incorporated in its entirety).

Measurement of Amount of Lysophosphatidylcholine

The amount of lysophosphatidylcholine was measured using standard techniques known to those of skill in the art (see, for example, Examples 6 and 7 of U.S. patent application Ser. No. 11/541,412, filed Sep. 28, 2006, the content of which is hereby incorporated in its entirety).

6.1 Example 1: Performance as Measured by Out-of-Bag Cross-Validation for Lysophosphatidylcholine, Temperature, Respiratory Rate, and Other Biomarkers as Predictors of Sepsis Using Logistic Regression Algorithms Examples 1 and 2 are provided that illustrate four data sets and two algorithmic approaches. The data sets document lysophosphatidylcholine performance as a stand alone marker and provide examples of selecting clinical markers or additional biomarkers that improve lysophosphatidylcholine performance as a predictor for sepsis.

Example 1 illustrates "out-of-bag" cross-validation of logistic regression results for lysophophatidylcholine, temperature, respiratory rate, and other biomarkers. In each example, 400 iterations of "out-of-bag" performance estimation were carried out. That is, for each of 400 iterations, 10% of the patients were randomly selected between the SIRS and sepsis training populations to be excluded from fitting, then predicted, forming the basis for a performance estimate. Besides balance between the two groups, there were no constraints from iteration to iteration; an individual patient could be selected twice in a row, for example. The results of the 400 iterations are averaged for a final performance estimate.

Table 1 provides the performance of out-of-bag cross-validation of logistic regression results using Lysophosphatidylcholine (LPC), Apache II Temperature (Temp), Apache II Respiratory Rate (RR), Procalcitonin (PCT), C-Reactive Protein (CRP), and Interleukin-6 (IL-6) marker models. In the Examples section, the term "Apache II Temperature," or "Apache II Respiratory Rate" indicates that the temperature and respiratory rate were measured at least every 4 hours, and the maximum value taken over the 24 hours preceding measurement of the amounts of lysophosphatidylcholine or biomarkers. In the Examples section, unless specified otherwise, the term "model" implies a specific algorithm fitted to a specific set of markers from a training set. For example, the "LPC, Temp, RR" model in Table 1 implies an algorithm fitted with LPC, Temp, and RR marker data from a training set.

There were 86 total subjects in the training set, of which 42 were SIRS subjects and 44 were sepsis subjects. The performance metrics in Table 1 represent the cross-validation performance. The data set includes 4 time points per subject.

TABLE 1

Performance of LPC, Temp, RR, and other biomarker models using a logistic regression algorithm with out-of-bag cross-validation

| Model | Accuracy % |
|---|---|
| LPC, Temp, RR | 72.66 |
| PCT, Temp, RR | 67.69 |
| LPC | 61.25 |
| LPC, PCT, CRP | 60.62 |
| LPC, PCT | 60.03 |
| LPC, IL-6 | 58.03 |
| PCT | 57.81 |
| LPC, CRP | 56.25 |
| CRP | 56.03 |
| IL-6 | 53.41 |

As can be seen from Table 1, a combination of the LPC, Temp and RR markers provides the highest accuracy model (72.66%) for prediction of sepsis. From Table 1, it can also be seen that inclusion of Temp and RR markers into the LPC model significantly increased the accuracy of the model from 61.24% to 72.66%.

Table 2 provides the performance of out-of-bag cross-validation of logistic regression results using Lysophosphatidylcholine (LPC), Apache II Temperature (Temp), and Apache II Respiratory Rate (RR) marker models. There were 46 total subjects in the training set, of which 25 were SIRS subjects and 21 were sepsis subjects. The performance metrics in Table 2 represent cross-validation performance. The data set included 1 time point per subject.

TABLE 2

Performance of LPC, Temp, and RR marker models using a logistic regression algorithm with out-of-bag cross-validation

| Model | Accuracy % |
| --- | --- |
| Temp | 72.56 |
| LPC, Temp, RR | 69.75 |
| RR | 67.25 |
| LPC | 54.81 |

As can be seen from Table 2, inclusion of Temp and RR markers into the LPC model significantly increased the accuracy from 54.81% to 69.75%.

Table 3 provides the performance of out-of-bag cross-validation of logistic regression results using Lysophosphatidylcholine (LPC), Apache II Temperature (Temp), Apache II Respiratory Rate (RR), HLA-DR and "TACH" models. As used herein, "TACH" model means that the markers TIFA (TRAF-interacting protein with a forkhead-associated domain), ARG2 (extra-hepatic arginase), CEACAM1 (carcinoembryonic antigen-related cell adhesion molecule 1), and HLA-DRA were used to fit the algorithm.

There were 256 total subjects in the test set, of which 116 were SIRS subjects and 140 were sepsis subjects. The performance metrics in Table 3 represent predicted performance of a test data set using logistic models fit from the training set (n=90). The data set used multiple time points per subject.

TABLE 3

Performance of TACH and other marker models using a logistic regression algorithm with out-of-bag cross-validation

| Model | Accuracy % |
| --- | --- |
| LPC, TACH | 66.41 |
| TACH | 64.84 |
| LPC, Temp, RR | 61.33 |
| LPC, HLA-DR | 60.94 |
| LPC, HLA-DR, Temp | 60.55 |
| HLA-DR, Temp, RR | 60.16 |
| Temp | 59.77 |
| LPC | 58.98 |
| HLA-DR, Temp | 58.98 |
| Temp, RR | 58.20 |
| LPC, HLA-DR, RR | 57.03 |
| HLA-DR, RR | 55.08 |
| HLA-DR | 52.34 |
| RR | 51.17 |

As can be seen from Table 3, inclusion of Temp and RR into the LPC model significantly increased the accuracy from 58.98% to 61.33%.

6.2 Example 2: Performance of Lysophosphatidylcholine, Temperature, and Respiratory Rate as Predictors of Sepsis Using Bayesian Longitudinal Algorithms Example 2 illustrates Bayesian Longitudinal algorithm results for the lysophophatidylcholine, temperature and respiratory rate. SIRS and sepsis data were modeled in moving windows of up to 3 days, and assay results were modeled as a multivariate longitudinal model within the window, in which assay results were assumed to vary linearly at a plurality of time points. Predictions for new subjects were made according to their estimated probability of belonging to the sepsis population. This probability was calculated by comparing probability densities of the new data for the SIRS and sepsis populations and weighing prevalence, i.e., by Bayes' theorem. Moreover, the parameters of the SIRS and sepsis longitudinal models are themselves estimated using Bayesian statistics which yield a "posterior" probability distribution over the unknown model parameters, and the probability of sepsis is averaged over this posterior distribution.

Classification with Bayesian longitudinal algorithms was computationally slower than with logistic regression, so predictive performance was estimated from averaging training data by 3 runs of 10-fold cross-validation. 10-fold cross-validation entails partitioning the patients into 10 approximately equal groups balanced for sepsis and SIRS representation, excluding in turn each of the 10 groups from fitting, and comparing predictions to observed results. The average performance over the 10 iterations is the performance estimate.

Table 4 provides the performance of Bayesian longitudinal algorithm results using Lysophosphatidylcholine (LPC), Apache II Temperature (Temp), and Apache II Respiratory Rate (RR) models. There were 90 total subjects in the training set, of which 45 were SIRS subjects and 45 were sepsis subjects. The performance metrics in Table 4 represent the Bayesian longitudinal model cross-validation performance. The data set included 3 time points per patient.

TABLE 4

Performance of LPC, Temp, and RR models using a Bayesian longitudinal algorithm

| Model | Accuracy % |
| --- | --- |
| LPC, Temp, RR | 79.5 |
| LPC | 72.0 |

As can be seen from Table 4, inclusion of Temp and RR into the LPC model significantly increased the accuracy from 72.0% to 79.5%.

Further, Examples 1 and 2 illustrate that the choice of algorithm to model the marker data does not determine the accuracy of the performance of that model. For example, regardless of whether a Bayesian longitudinal algorithm or out-of-bag cross-validation of logistic regression analysis was used, the inclusion of Temp and RR into the LPC model was found to significantly increase accuracy. This suggests that the methods, monitors, and systems of the invention are algorithm independent.

6.3 Example 3: Predicted Performance of Lysophosphatidylcholine, Temperature, and Respiratory Rate Markers for the Advanced Detection of Sepsis Example 3 illustrates that lysophosphatidylcholine, temperature and respiratory rate can be used for the advanced detection of sepsis in a subject. The example also illustrates that the inclusion of the temperature and respiratory rate markers significantly increases the accuracy of the lysophosphatidylcholine model for advanced detection.

In this example, historical models were applied to a test population of 257 subjects.

Historical Training and Model Building

Cross-validation performed on training data and each model (LPC, Temp, L P C and Temp, Temp and RR, and LPC, Temp and RR) used an out-of-bag, boot strapping sampling procedure iterated N times (N=400), where at each iteration logistic regression models were fit and predicted probabilities computed for samples held back from the model. Then a threshold was selected for each model from the cross-validation procedure such that accuracy was maximized given specificity greater than 90%. Once the thresholds were selected the final logistic regression models were fit using all the training data and thresholds selected through cross-validation.

Figure 2:
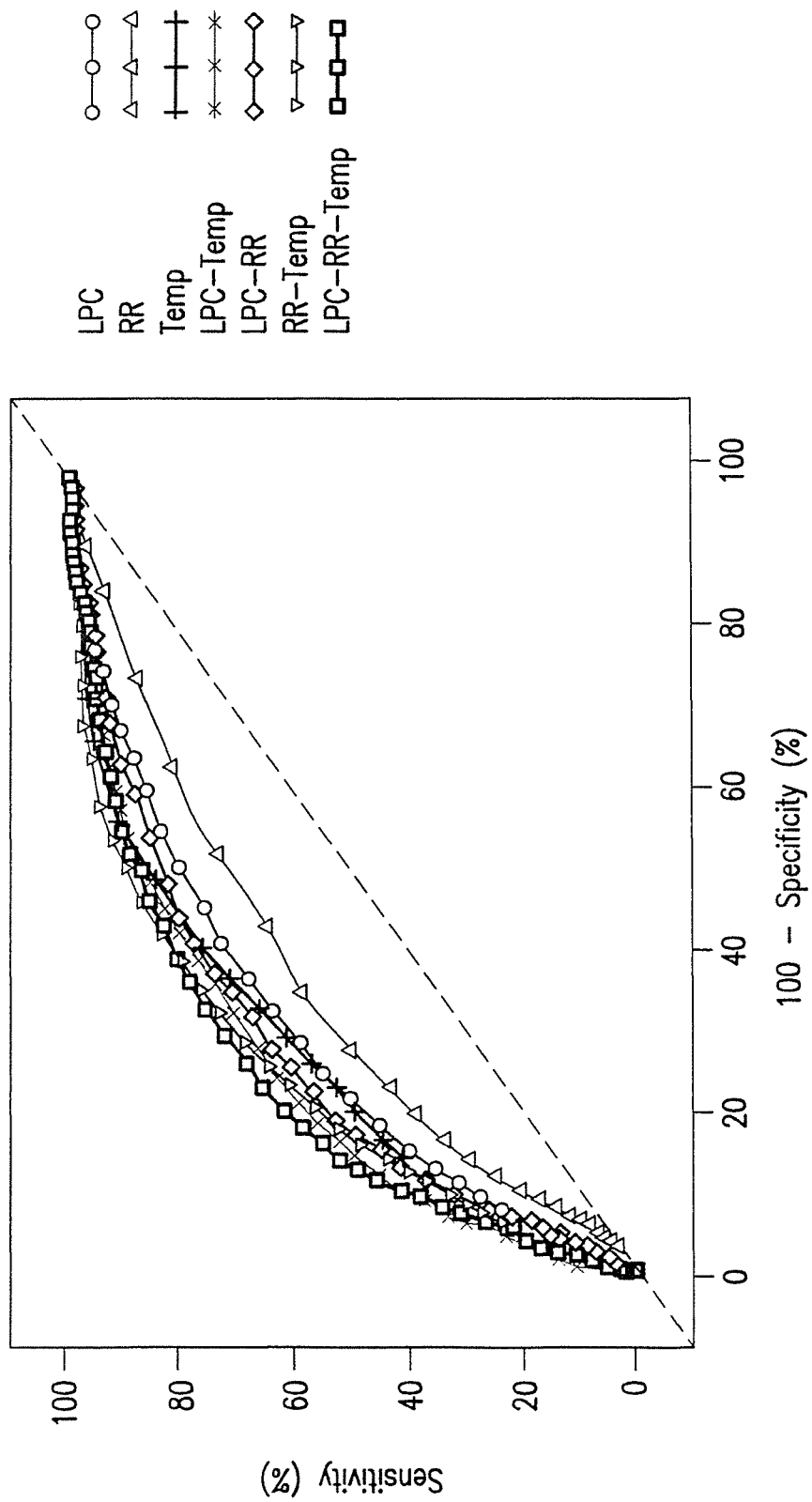
FIG. 2 is a graphical representation of ROC curves for historical lysophosphatidylcholine, temperature and respiratory rate data.

The area under the curve (AUC) and ROC curves for the historical models are presented in Table 5 and FIG. 2.

TABLE 5

Area under the curve and specific area for various historical marker models

| Model | Total Area | Spec Area |
|---|---|---|
| LPC | 0.71601 | 0.02884 |
| RR | 0.64771 | 0.01937 |
| Temp | 0.74484 | 0.03333 |
| LPC and Temp | 0.76956 | 0.03909 |
| LPC and RR | 0.73801 | 0.03166 |
| RR and Temp | 0.77397 | 0.03397 |
| LPC, RR and Temp | 0.77985 | 0.03925 |

Cross-validation performance from the historical marker models constructed using training data is presented Table 6.

TABLE 6

Performance of various historical marker models

| Model | Threshold | Accuracy (%) | Specificity (%) | Sensitivity (%) |
|---|---|---|---|---|
| LPC | 0.75502 | 59.45 (49.18, 69.28) | 90.00 (79.47, 96.79) | 28.90 (16.99, 42.71) |
| RR | 0.66667 | 54.62 (44.32, 64.71) | 90.25 (79.81, 96.93) | 19.00 (9.28, 31.51) |
| Temp | 0.72289 | 62.35 (52.14, 71.98) | 90.50 (80.15, 97.07) | 34.20 (21.45, 48.38) |
| LPC and Temp | 0.78313 | 65.62 (55.54, 74.99) | 90.00 (79.47, 96.79) | 41.25 (27.67, 55.62) |
| LPC and RR | 0.78313 | 61.52 (51.29, 71.21) | 90.44 (80.06, 97.04) | 32.60 (20.08, 46.69) |
| RR and Temp | 0.75904 | 61.74 (51.52, 71.42) | 90.69 (80.4, 97.18) | 32.80 (20.25, 46.9) |
| LPC, RR and Temp | 0.81526 | 64.58 (54.45, 74.03) | 90.25 (79.81, 96.93) | 38.90 (25.56, 53.24) |

As can be seen from Table 6, inclusion of Temp and RR markers into the LPC model significantly increased the accuracy from 59.45% to 64.58%.

Coefficients used in the historical marker models are presented in Table 7.

TABLE 7

Coefficients used in the historical marker models

| | Coefficients | | | | |
|---|---|---|---|---|---|
| Model | (Intercept) | LPC | Temp | RR | Threshold |
| LPC | 2.51269 | −0.03372 | | | 0.75502 |
| RR | −0.58421 | | | 0.02754 | 0.66667 |
| Temp | −36.76293 | | 0.36634 | | 0.72289 |
| LPC and Temp | −26.76737 | −0.03062 | 0.28863 | | 0.78313 |
| LPC and RR | 1.79624 | −0.03400 | | 0.02867 | 0.78313 |
| RR and Temp | −35.60982 | | 0.34984 | 0.01983 | 0.75904 |
| LPC, RR and Temp | −25.19826 | −0.03102 | 0.26767 | 0.02232 | 0.81526 |

Test Performance

The all aforementioned variations of the historical marker models were applied to the complete marker data set comprised of 257 subjects processed for test samples and the predicted performance is summarized in Table 8.

TABLE 8

Predicted performance of test marker models

| Model | Threshold | Accuracy (%) | Sensitivity (%) | Specificity (%) |
|---|---|---|---|---|
| LPC | 0.75502 | 58.75 | 44.29 | 76.07 |
| RR | 0.66667 | 47.47 | 5.71 | 97.44 |
| Temp | 0.72289 | 59.14 | 35.00 | 88.03 |
| LPC and Temp | 0.78313 | 64.59 | 55.00 | 76.07 |
| LPC and RR | 0.78313 | 61.48 | 41.43 | 85.47 |
| RR and Temp | 0.75904 | 55.25 | 27.14 | 88.89 |
| LPC, Temp and RR | 0.81526 | 65.37 | 47.86 | 86.32 |

Table 9 shows a calculation of the cumulative likelihood ratio for each time point T-324 to T-12, where the T-12 likelihood ratio uses all the data less than or equal to T-12, and similarly, the T-60 likelihood ratio uses all data time points less than or equal to T-60, etc.

TABLE 9

Cumulative likelihood ratio for each time point T-324 to T-12

| | Time | | | | | | | | | | | | |
|---|---|---|---|---|---|---|---|---|---|---|---|---|---|
| Model | −324 | −300 | −276 | −252 | −228 | −204 | −180 | −156 | −132 | −108 | −84 | −60 | −36 | −12 |
| LPC | 0.00 | 0.00 | 0.00 | 1.43 | 0.39 | 0.53 | 0.96 | 1.42 | 2.62 | 1.99 | 1.91 | 1.51 | 1.64 | 1.85 |
| RR | | | | | | ∞ | 1.58 | 0.86 | 1.28 | 2.20 | 1.38 | 1.95 | 2.23 | |

TABLE 9-continued

Cumulative likelihood ratio for each time point T-324 to T-12

| Model | -324 | -300 | -276 | -252 | -228 | -204 | -180 | -156 | -132 | -108 | -84 | -60 | -36 | -12 |
|---|---|---|---|---|---|---|---|---|---|---|---|---|---|---|
| Temp | | | | 0.00 | 0.00 | 0.00 | 0.40 | 0.20 | 0.62 | 1.08 | 1.56 | 1.69 | 1.74 | 2.92 |
| LPC and Temp | 0.00 | 0.00 | 0.00 | 0.00 | 0.59 | 0.64 | 1.07 | 1.23 | 1.51 | 1.67 | 1.81 | 1.98 | 2.07 | 2.30 |
| LPC and RR | | | | ∞ | 0.79 | 0.80 | 3.20 | 3.16 | 4.00 | 2.70 | 2.70 | 2.14 | 2.30 | 2.85 |
| RR and Temp | | | | | 0.00 | 0.80 | 1.60 | 1.05 | 1.20 | 1.14 | 1.51 | 1.55 | 1.82 | 2.44 |
| LPC, Temp and RR | | | | 0.00 | 0.39 | 0.40 | 1.60 | 1.38 | 2.06 | 2.68 | 2.84 | 2.66 | 2.92 | 3.50 |

Figure 3:
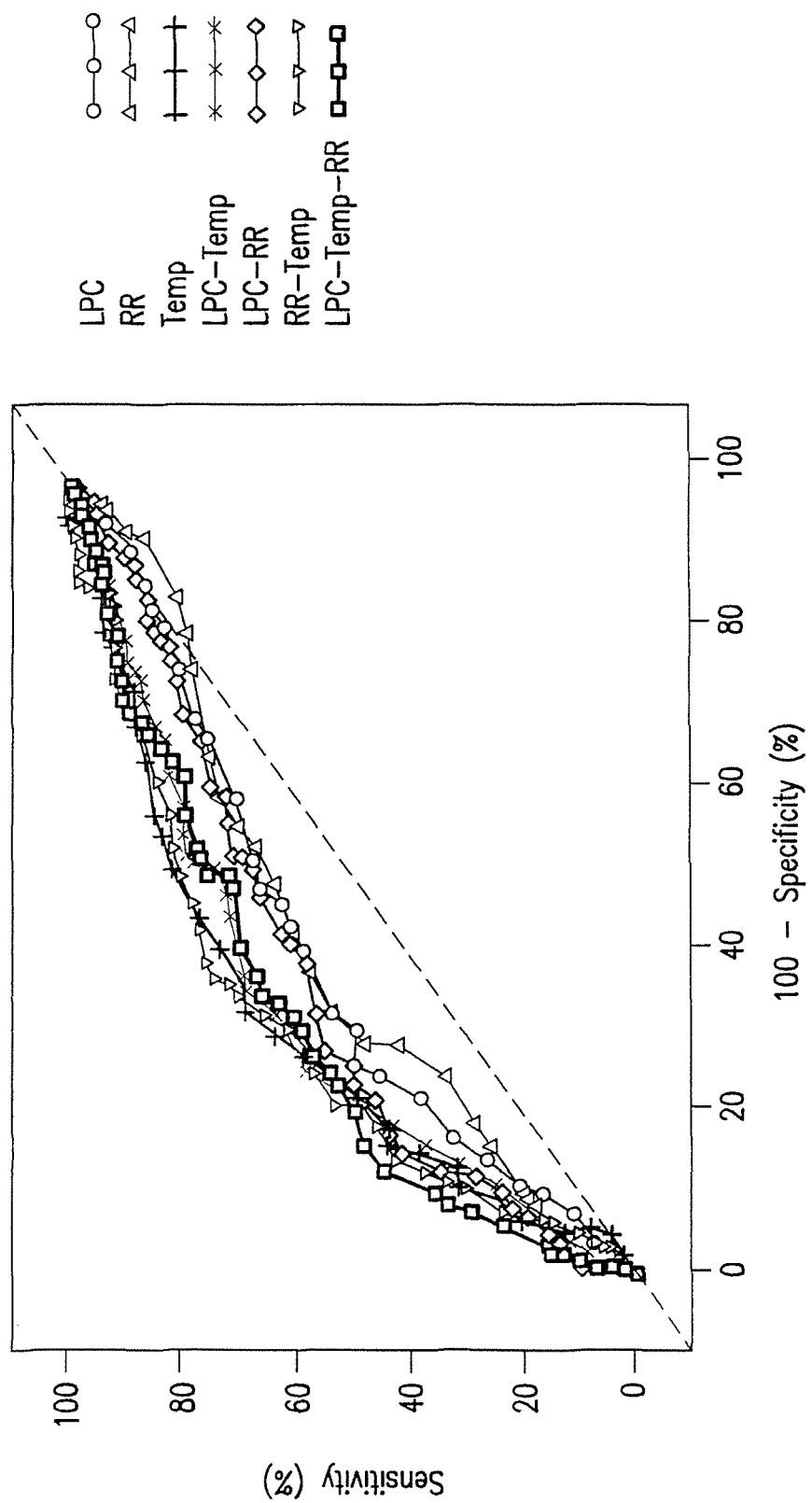
FIG. 3 is a graphical representation of ROC curves for test lysophosphatidylcholine, temperature and respiratory rate data.

Using the predicted probabilities from applying the metabolite models to the test data set, the threshold can be varied to produce ROC curves and measure the area under the curve. This gives an indication if a different threshold might have better served the test data. The area under the curve (AUC) and ROC curves for the historical models are presented in Table 10 and FIG. 3.

TABLE 10

Area under the curve and specific area for various test marker models

| Model | Total Area | Spec Area |
|---|---|---|
| LPC | 0.60071 | 0.01696 |
| RR | 0.58386 | 0.01928 |
| Temp | 0.70657 | 0.02723 |
| LPC and Temp | 0.68235 | 0.02452 |
| LPC and RR | 0.63303 | 0.02507 |
| RR and Temp | 0.70795 | 0.02702 |
| LPC, Temp and RR | 0.69787 | 0.03539 |

Among the sepsis patients who were correctly identified as septic for a given model, call plots were generated, based on a time normalization where T-12 is the day of onset of sepsis for a sepsis patient and T-12 is the last available day for a SIRS patient. Table 11 summaries the number of sepsis patients correctly identified as sepsis for each model, the number false positives and the total population of sepsis patients.

TABLE 11

Number of sepsis patients correctly identified as sepsis for each test marker model

| Model | True Positive | False Negative | Total |
|---|---|---|---|
| LPC | 62 | 78 | 140 |
| RR | 8 | 132 | 140 |
| Temp | 49 | 91 | 140 |
| LPC and Temp | 77 | 63 | 140 |
| LPC and RR | 58 | 82 | 140 |
| RR and Temp | 38 | 102 | 140 |
| LPC, Temp and RR | 67 | 73 | 140 |

Figure 4:
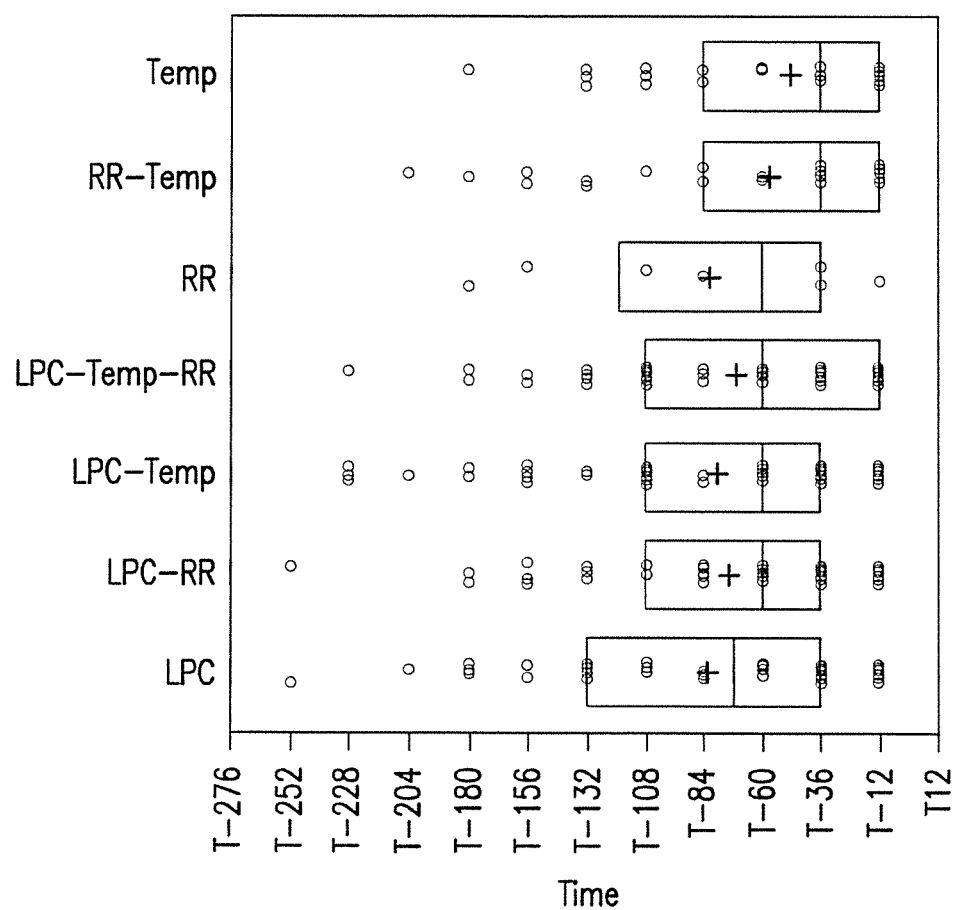
FIG. 4 is a graphical representation of the time of call for test lysophosphatidylcholine, temperature and respiratory rate data.

FIG. 4 is a graphical representation of the time of call for the test data according to the model used. Only the true positive calls of Table 11 are plotted. The test data is presented as a "box" plot, where the right-hand side of the box corresponds to the 25% lower quantile for the test data, and the left-hand side of the box corresponds to the 25% upper quantile for the test. The line in the middle of the box represents the median of the test data, whereas the cross ("+") represents the average of the test data. The x-axis represents time points in hours, where T-0 (time zero) represents the moment of onset, T-12 represents 12 hours prior to onset, T-36 represents 36 hours prior to onset, and so forth. The day of onset is encompassed by the 24-hour hour period between T-12 and T12. Consequently, any call up to and including the time point T-12 represents a sepsis call at least 12 hours prior to the moment of onset to sepsis.

As can be seen from FIG. 4, it is possible to use lysophosphatidylcholine, temperature and respiratory rate markers to detect sepsis as early as T-132 or T-108, which represents anywhere from about four to five days prior to the day of onset, at T-12.

6.4 Example 4: Predicted Performance of Lysophosphatidylcholine, Temperature, Respiratory Rate, and Additional Biomarkers for the Advanced Detection of Sepsis Example 4 illustrates that lysophosphatidylcholine, temperature, respiratory rate, and additional biomarkers can be used for the advanced detection of sepsis in a subject. The example also illustrates that the inclusion of additional biomarkers can significantly increase the accuracy of the lysophosphatidylcholine model for advanced detection.

In this example, historical models were applied to a test population of 257 subjects.

Historical Training and Model Building

Cross-validation performed on the TACH model, metabolite models, and a combination of the two used an out-of-bag, bootstrap sampling procedure iterated N times (N=400), where at each iteration a logistic regression model was fit and predicted probabilities computed for samples held back from the model. Then a threshold was selected from the cross-validation procedure such that accuracy was maximized given specificity greater than 90%. Once the threshold was selected a final logistic regression model was fit using all the training data and threshold selected through cross-validation.

Figure 5:
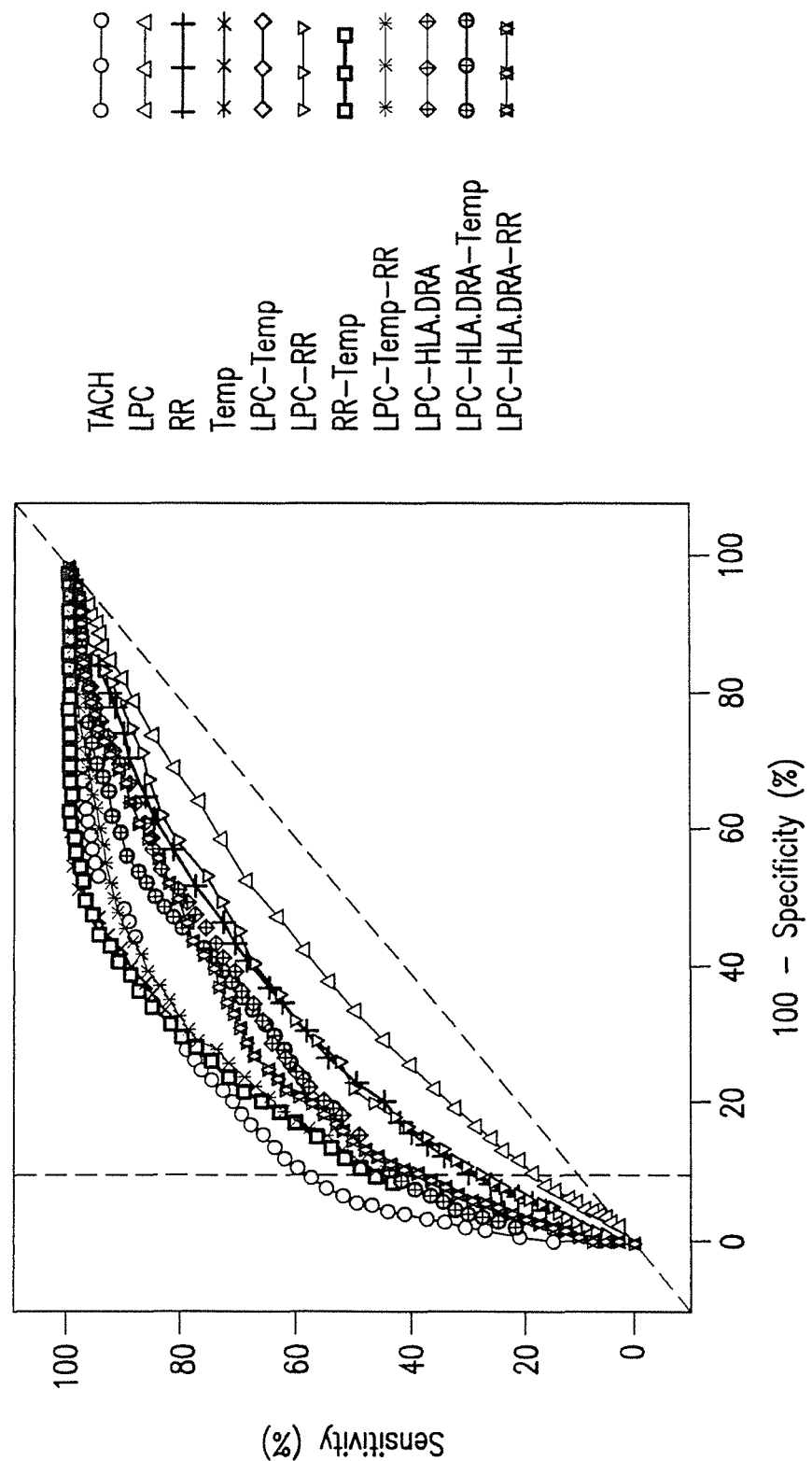
FIG. 5 is a graphical representation of ROC curves for historical lysophosphatidylcholine, temperature, respiratory rate, and biomarker data.

Area under the curve (AUC) and ROC curves for the historical models are presented in Table 12 and FIG. 5.

TABLE 12

Area under the curve and specific area for various historical marker models

| Model | Total Area | Spec Area |
|---|---|---|
| TACH | 0.8203 | 0.0541 |
| LPC | 0.71601 | 0.02884 |
| RR | 0.64771 | 0.01937 |
| Temp | 0.74484 | 0.03333 |
| LPC and Temp | 0.76956 | 0.03909 |
| LPC and RR | 0.73801 | 0.03166 |
| RR and Temp | 0.77397 | 0.03397 |
| LPC, RR and Temp | 0.77985 | 0.03925 |
| LPC and HLA.DRA | 0.73512 | 0.03889 |
| LPC, HLA.DRA and Temp | 0.75395 | 0.04171 |
| LPC, HLA.DRA and RR | 0.74506 | 0.03735 |

Cross validated training performance for the TACH and metabolite models is presented in Table 13.

TABLE 13

Performance of various historical marker models

| Model | Thresh. | Accuracy (%) | Specificity (%) | Sensitivity (%) |
|---|---|---|---|---|
| TACH | 0.79518 | 73.03 (63, 81.9) | 90.31 (79.15, 97.24) | 55.75 (41.07, 69.89) |
| LPC | 0.75502 | 59.45 (49.18, 69.28) | 90.00 (79.47, 96.79) | 28.90 (16.99, 42.71) |
| RR | 0.66667 | 54.62 (44.32, 64.71) | 90.25 (79.81, 96.93) | 19.00 (9.28, 31.51) |
| Temp | 0.72289 | 62.35 (52.14, 71.98) | 90.50 (80.15, 97.07) | 34.20 (21.45, 48.38) |
| LPC and Temp | 0.78313 | 65.62 (55.54, 74.99) | 90.00 (79.47, 96.79) | 41.25 (27.67, 55.62) |
| LPC and RR | 0.78313 | 61.52 (51.29, 71.21) | 90.44 (80.06, 97.04) | 32.60 (20.08, 46.69) |
| RR and Temp | 0.75904 | 61.74 (51.52, 71.42) | 90.69 (80.4, 97.18) | 32.80 (20.25, 46.9) |
| LPC, RR and Temp | 0.81526 | 64.58 (54.45, 74.03) | 90.25 (79.81, 96.93) | 38.90 (25.56, 53.24) |
| LPC and HLA.DRA | 0.70683 | 64.63 (54.50, 74.08) | 90.06 (79.56, 96.83) | 39.20 (25.83, 53.55) |
| LPC, HLA.DRA and Temp | 0.73896 | 65.66 (55.58, 75.02) | 90.38 (79.98, 97.00) | 40.95 (27.40, 55.32) |
| LPC, HLA.DRA and RR | 0.79116 | 63.84 (53.68, 73.35) | 90.13 (79.62, 96.86) | 37.55 (24.37, 51.86) |

As can be seen from Table 13, inclusion of biomarker data into the LPC model significantly increased the accuracy, from 59.45% to 64.63%, for the inclusion of HLA.DRA, for example. Inclusion of temperature data further increases the accuracy of the LPC, HLA.DRA model to 65.66%.

Coefficients used in the TACH model are presented in Table 14.

TABLE 14

Coefficients used in the TACH model

| Intercept | TIFA.18S | ARG2.18S | CEACAM1.18S | HLA.DRA.18S |
|---|---|---|---|---|
| 19.672 | −0.880 | −0.394 | −0.316 | 0.628 |

Coefficients used in the historical marker models combining LPC and clinical markers are presented in Table 15.

TABLE 15

Coefficients used in the historical marker models

| Model | (Intercept) | LPC | Temp | RR | Threshold |
|---|---|---|---|---|---|
| LPC | 2.51269 | −0.03372 | | | 0.75502 |
| RR | −0.58421 | | | 0.02754 | 0.66667 |
| Temp | −36.76293 | | 0.36634 | | 0.72289 |
| LPC and Temp | −26.76737 | −0.03062 | 0.28863 | | 0.78313 |
| LPC and RR | 1.79624 | −0.03400 | | 0.02867 | 0.78313 |
| RR and Temp | −35.60982 | | 0.34984 | 0.01983 | 0.75904 |
| LPC, RR and Temp | −25.19826 | −0.03102 | 0.26767 | 0.02232 | 0.81526 |

Coefficients used in the historical marker models combining LPC, clinical markers, and the HLA.DRA marker are presented in Table 16.

TABLE 16

Coefficients used in the historical marker models incorporating HLA.DRA

| Model | (Intercept) | LPC | HLA.DRA | Temp | RR | Threshold |
|---|---|---|---|---|---|---|
| LPC and HLA.DRA | −8.95995 | −0.02560 | 0.69793 | | | 0.70683 |
| LPC, HLA.DRA and Temp | −28.89194 | −0.02413 | 0.63354 | 0.20678 | | 0.73896 |
| LPC, HLA.DRA and RR | −9.73960 | −0.02580 | 0.66111 | | 0.05194 | 0.79116 |

Test Performance

The TACH and marker models were applied to common set of 257 subjects processed for test samples and the predicted performance is summarized in Table 17.

TABLE 17

Predicted performance of test marker models

| Model | Accuracy (%) | Specificity (%) | Sensitivity (%) |
|---|---|---|---|
| TACH | 65.63 (59.7, 71.3) | 80.17 (72.43, 86.83) | 53.57 (45.3, 61.73) |
| LPC | 58.59 (52.51, 64.54) | 75.86 (67.67, 83.13) | 44.29 (36.19, 52.55) |
| RR | 47.27 (41.19, 53.38) | 97.41 (93.74, 99.42) | 5.71 (2.56, 10.18) |
| Temp | 58.98 (52.9, 64.92) | 87.93 (81.37, 93.13) | 35.00 (27.37, 43.08) |
| LPC and Temp | 64.45 (58.49, 70.18) | 75.86 (67.67, 83.13) | 55.00 (46.73, 63.12) |
| LPC and RR | 61.33 (55.29, 67.18) | 85.34 (78.33, 91.09) | 41.43 (33.44, 49.67) |
| RR and Temp | 55.08 (48.96, 61.11) | 88.79 (82.41, 93.79) | 27.14 (20.16, 34.81) |
| LPC, Temp and RR | 65.23 (59.3, 70.92) | 86.21 (79.33, 91.78) | 47.86 (39.66, 56.12) |
| LPC and HLA.DRA | 60.94 (54.89, 66.81) | 85.34 (78.33, 91.09) | 40.71 (32.76, 48.94) |
| LPC, HLA.DRA and Temp | 60.55 (54.49, 66.43) | 83.62 (76.34, 89.7) | 41.43 (33.44, 49.67) |
| LPC, HLA.DRA and RR | 57.03 (50.93, 63.02) | 87.07 (80.35, 92.46) | 32.14 (24.72, 40.1) |

Figure 6:
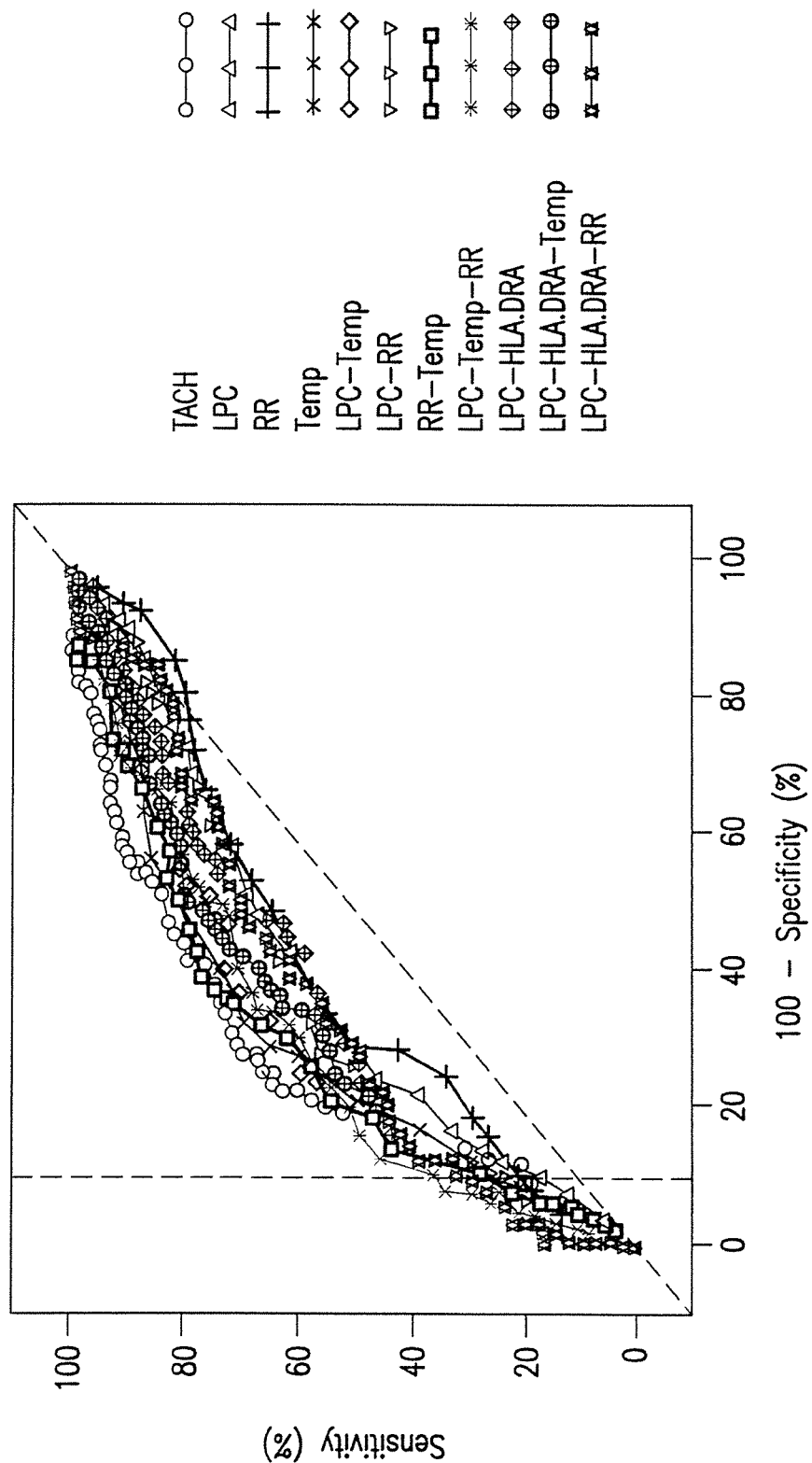
FIG. 6 is a graphical representation of ROC curves for test lysophosphatidylcholine, temperature, respiratory rate, and biomarker data.

Using the predicted probabilities from applying the models to the test data set, the threshold can be varied to produce ROC curves and measure the area under the curve. This gives a indication if a different threshold might have better served the test data. The area under the curve (AUC) and ROC curves for the historical models are presented in Table 18 and FIG. 6.

TABLE 18

Area under the curve and specific area of test marker models

| Model | Total Area | Spec Area |
|---|---|---|
| TACH | 0.73016 | 0.02014 |
| LPC | 0.59985 | 0.01679 |
| RR | 0.58085 | 0.01918 |
| Temp | 0.70624 | 0.02700 |
| LPC and Temp | 0.68140 | 0.02435 |
| LPC and RR | 0.63137 | 0.02481 |
| RR and Temp | 0.70691 | 0.02674 |
| LPC, Temp and RR | 0.69647 | 0.03517 |
| LPC and HLA.DRA | 0.64514 | 0.03097 |
| LPC, HLA.DRA and Temp | 0.67718 | 0.02782 |
| LPC, HLA.DRA and RR | 0.63686 | 0.02943 |

Daily cumulative and daily snapshot likelihood ratios are computed on the time normalized data. The daily cumulative ratio is calculated by using all prior time-points for a given patient including the current time-point. If a patient is called false positive at anytime prior to current time-point the patient is counted as a false positive regardless of whether or not the current time-point is a false positive. Table 19 presents the daily cumulative and daily snapshot likelihood ratios on the time normalized data.

TABLE 19

Daily cumulative and daily snapshot likelihood ratios for each test model

| | | Time | | | | | | | | | | | | |
|---|---|---|---|---|---|---|---|---|---|---|---|---|---|---|
| | Type | −324 | −300 | −276 | −252 | −228 | −204 | −180 | −156 | −132 | −108 | −84 | −60 | −36 | −12 |
| TACH | daily | | | 3.00 | 0.00 | 0.00 | 0.65 | ∞ | 2.45 | 3.67 | 2.97 | 3.65 | 6.22 | 5.16 | 4.56 |
| | cumulative | | | 3.00 | 1.67 | 0.39 | 0.47 | 1.02 | 1.57 | 2.00 | 2.55 | 2.61 | 3.35 | 3.11 | 2.70 |
| LPC | daily | 0.00 | | | ∞ | 0.79 | 0.83 | 1.02 | 4.95 | 6.22 | 2.42 | 1.46 | 1.61 | 3.20 | 4.08 |
| | cumulative | 0.00 | 0.00 | 0.00 | 1.43 | 0.39 | 0.53 | 0.96 | 1.42 | 2.62 | 1.99 | 1.91 | 1.51 | 1.63 | 1.83 |
| Temp | daily | | | | 0.00 | 0.00 | 0.00 | 0.77 | 0.27 | 0.89 | 6.90 | 2.10 | 2.72 | 5.60 | 7.99 |
| | cumulative | | | | 0.00 | 0.00 | 0.00 | 0.40 | 0.20 | 0.62 | 1.08 | 1.56 | 1.69 | 1.73 | 2.90 |
| RR | daily | | | | | | | ∞ | 0.83 | 0.00 | ∞ | ∞ | 1.02 | ∞ | 1.68 |
| | cumulative | | | | | | | ∞ | 1.58 | 0.86 | 1.28 | 2.20 | 1.38 | 1.93 | 2.21 |
| LPC, Temp | daily | 0.00 | | 0.00 | 0.00 | 1.18 | 0.83 | 3.83 | 1.65 | 2.89 | 4.10 | 3.66 | 2.95 | 5.33 | 4.20 |
| | cumulative | 0.00 | 0.00 | 0.00 | 0.00 | 0.59 | 0.64 | 1.07 | 1.23 | 1.51 | 1.67 | 1.81 | 1.98 | 2.05 | 2.28 |
| LPC, RR | daily | | | | ∞ | 0.00 | ∞ | ∞ | 3.30 | 6.09 | 2.26 | 3.92 | 2.04 | 3.33 | 4.90 |
| | cumulative | | | | 00 | 0.79 | 0.80 | 3.20 | 3.16 | 4.00 | 2.70 | 2.70 | 2.14 | 2.28 | 2.83 |
| RR, Temp | daily | | | | | 0.00 | 0.83 | 0.77 | 0.82 | 0.70 | 3.40 | 1.73 | 1.70 | 6.80 | 5.67 |
| | cumulative | | | | | 0.00 | 0.80 | 1.60 | 1.05 | 1.20 | 1.14 | 1.51 | 1.55 | 1.81 | 2.42 |
| LPC, Temp, RR | daily | | | | 0.00 | 0.39 | ∞ | ∞ | 1.65 | 2.03 | 7.22 | 4.61 | 4.33 | 23.20 | 6.72 |
| | cumulative | | | | 0.00 | 0.39 | 0.40 | 1.60 | 1.38 | 2.06 | 2.68 | 2.84 | 2.66 | 2.90 | 3.47 |
| LPC, HLA.DRA | daily | 0.00 | 0.00 | 1.50 | | 0.31 | 0.22 | ∞ | 2.17 | 2.05 | 4.17 | 6.40 | 4.11 | 7.87 | 10.93 |
| | cumulative | 0.00 | 0.00 | 1.50 | 0.83 | 0.52 | 0.35 | 0.55 | 1.12 | 1.47 | 2.00 | 2.51 | 2.68 | 2.59 | 2.78 |
| LPC, HLA.DRA, Temp | daily | | | 3.00 | | 0.62 | 0.16 | 0.48 | 2.17 | 1.64 | 3.79 | 7.20 | 4.11 | 7.11 | 9.88 |
| | cumulative | | | 3.00 | 1.67 | 0.79 | 0.35 | 0.44 | 0.70 | 1.29 | 1.75 | 2.26 | 2.39 | 2.24 | 2.53 |
| LPC, HLA.DRA, RR | daily | 0.00 | | 0.00 | | ∞ | 0.65 | ∞ | 2.17 | 2.50 | 2.22 | 3.94 | 2.88 | 10.47 | 8.41 |
| | cumulative | 0.00 | 0.00 | 0.00 | 0.00 | 0.79 | 0.35 | 0.73 | 1.16 | 1.68 | 1.95 | 2.44 | 2.07 | 2.36 | 2.49 |

Table 20 summaries the number of sepsis patients correctly identified as sepsis, the number false negatives and the total sepsis population.

TABLE 20

Number of sepsis patients correctly identified as sepsis for each test model

| Model | False Neg | True Pos | Total |
|---|---|---|---|
| TACH | 65 | 75 | 140 |
| LPC | 78 | 62 | 140 |
| RR | 132 | 8 | 140 |
| Temp | 91 | 49 | 140 |
| LPC and Temp | 63 | 77 | 140 |
| LPC and RR | 82 | 58 | 140 |
| RR and Temp | 102 | 38 | 140 |
| LPC, Temp and RR | 73 | 67 | 140 |
| LPC and HLA.DRA | 83 | 57 | 140 |
| LPC, HLA.DRA and Temp | 82 | 58 | 140 |
| LPC, HLA.DRA and RR | 95 | 45 | 140 |

Table 21 presents the number of SIRS patients called positive and the total SIRS population.

TABLE 21

Number of SIRS patients called positive for each test model

| Model | False Pos | True Neg | Total |
|---|---|---|---|
| TACH | 23 | 93 | 116 |
| LPC | 28 | 88 | 116 |
| RR | 3 | 113 | 116 |
| Temp | 14 | 102 | 116 |
| LPC and Temp | 28 | 88 | 116 |
| LPC and RR | 17 | 99 | 116 |
| RR and Temp | 13 | 103 | 116 |
| LPC, Temp and RR | 16 | 100 | 116 |
| LPC and HLA.DRA | 17 | 99 | 116 |
| LPC, HLA.DRA and Temp | 19 | 97 | 116 |
| LPC, HLA.DRA and RR | 15 | 101 | 116 |

Figure 7:
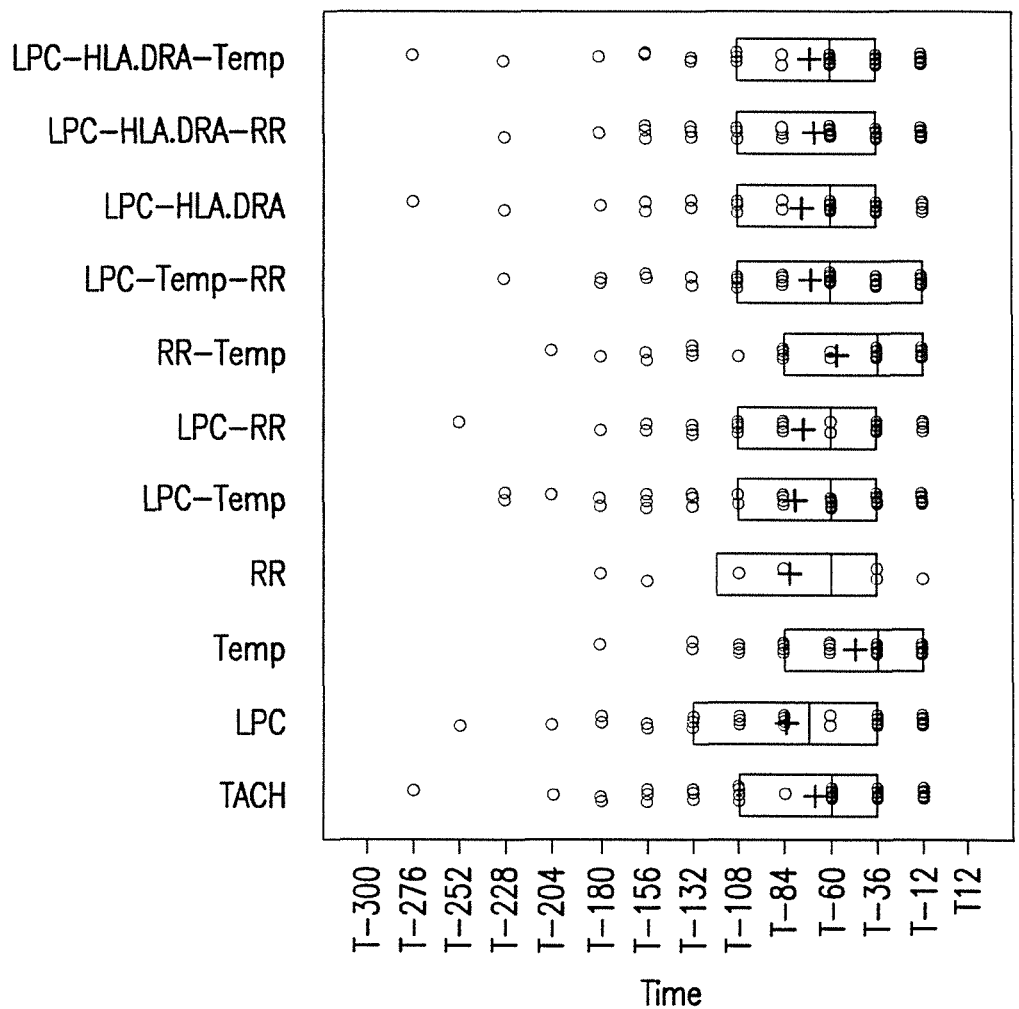
FIG. 7 is a graphical representation of the time of call for test lysophosphatidylcholine, temperature, respiratory rate, and biomarker data.

FIG. 7 is a graphical representation of the time of call for the test data according to the model used. Only the true positive calls of Table 21 are plotted.

As can be seen from FIG. 7, it is possible to use lysophosphatidylcholine and additional biomarkers to detect sepsis as early as T-132 or T-108, which represents anywhere from about four to five days prior to the day of onset, at T-12.

6.5 Example 5: Example Calculation of Probability of Sepsis for Two Test Subjects Using the "LPC, Temp, RR" Model Example 5 presents an example calculation of probability of sepsis for two test subjects using the "LPC, Temp, RR" model. Example 5 illustrates that a calculation of a probability of sepsis can be used for the advanced detection of sepsis in a subject. The example also illustrates that a calculation of a probability of sepsis can be used to assess the likelihood of onset of sepsis, prior to the onset of sepsis.

Probability of sepsis, P(Sepsis), was calculated using the LPC, Temp and RR marker values measured over time for the test subject. One test subject was "SIRS" patient, M107. The other test subject was "sepsis" patient, M163. The SIRS patient, M107, was not diagnosed as septic as of the last day of the study (day 13). The sepsis patient, M163, was diagnosed as septic on day 8 of the study.

The coefficients for the "LPC, Temp, RR" model were calculated from the marker values for LPC, Temp and RR, as follows:

$$\eta = \log it(P(Sepsis)) = -25.19826 + -0.03102 * LPC + 0.26767 * Temp + 0.02232 * RR,$$

where P(Sepsis) is the calculated probability of sepsis, and where $\log it(P) = \log \{P/(1-P)\} = \log (P) - \log (1-P)$. As seen from the equation, the $\eta = \log it(P(Sepsis))$ value can be calculated from a linear combination of the separate LPC, Temp and RR marker values. The log it(P(Sepsis)) value therefore represents an "index" that can be used to calculate probability of sepsis.

The log it(P(Sepsis)) value was used to calculate probability of sepsis as follows:

$$P(Sepsis) = e^{\{\eta\}} / (1 + e^{\{\eta\}}) = 1 - 1/(1 + e^{\{\eta\}}).$$

The probability value, P(Sepsis), represents probability of sepsis. The threshold for the probability scale was 0.81526. When P(Sepsis) exceeded this threshold (P(Sepsis) >0.81526), sepsis was detected.

Table 22 presents the log it(P(Sepsis)) and P(Sepsis) values calculated on each day of the study for SIRS patient, M107.

TABLE 22

Logit(P(Sepsis)) and P(Sepsis) values calculated for SIRS patient, M107

| Day | LPC | RR | Temp | Truth | Logit | P(Sepsis) |
|---|---|---|---|---|---|---|
| 1 | 66.15 | 15 | 96 | SIRS | −1.2191 | 0.2281 |
| 2 | 61.57 | 16 | 100 | SIRS | 0.0160 | 0.5040 |
| 3 | 64.65 | 20 | 101.8 | SIRS | 0.4915 | 0.6205 |
| 4 | 67.1 | 12 | 99.8 | SIRS | −0.2984 | 0.4259 |
| 6 | 68.34 | 24 | 100 | SIRS | −0.0155 | 0.4961 |
| 7 | 67.3 | 19 | 101.2 | SIRS | 0.2264 | 0.5564 |
| 8 | 70.88 | 20 | 101.4 | SIRS | 0.1912 | 0.5477 |
| 9 | 69.57 | 18 | 101.2 | SIRS | 0.1336 | 0.5334 |
| 10 | 77.51 | 18 | 101.2 | SIRS | −0.1127 | 0.4719 |
| 11 | 84.47 | 20 | 100 | SIRS | −0.6051 | 0.3532 |
| 12 | 66.43 | 30 | 100.2 | SIRS | 0.2312 | 0.5575 |
| 13 | 88.22 | 30 | 101.6 | SIRS | −0.0700 | 0.4825 |

According to Table 22, P(Sepsis) for SIRS patient, M163, never exceeded the threshold for detection of sepsis.

Table 23 presents the log it(P(Sepsis)) and P(Sepsis) values calculated on each day of the study for sepsis patient, M163.

TABLE 23

Logit(P(Sepsis)) and P(Sepsis) values calculated for sepsis patient, M163

| Day | LPC | RR | Temp | Truth | Logit | P(Sepsis) |
|---|---|---|---|---|---|---|
| 1 | 37.65 | 17 | 101.3 | Sepsis | 1.1282 | 0.7555 |
| 2 | 34.43 | 18 | 101.8 | Sepsis | 1.3843 | 0.7997 |
| 3 | 33.88 | 19 | 101.7 | Sepsis | 1.3969 | 0.8017 |
| 4 | 36.45 | 25 | 102.7 | Sepsis | 1.7188 | 0.8480 |
| 5 | 55.44 | 20 | 100.3 | Sepsis | 0.3757 | 0.5928 |
| 6 | 50.74 | 29 | 100.8 | Sepsis | 0.8562 | 0.7019 |
| 7 | 56.01 | 34 | 100.2 | Sepsis | 0.6437 | 0.6556 |
| 8 | 44.1 | 37 | 102.4 | Sepsis | 1.6690 | 0.8414 |

According to Table 23, P(Sepsis) for sepsis patient, M163, exceeded the threshold for detection of sepsis on day 4 and on day 8.

Figure 8:
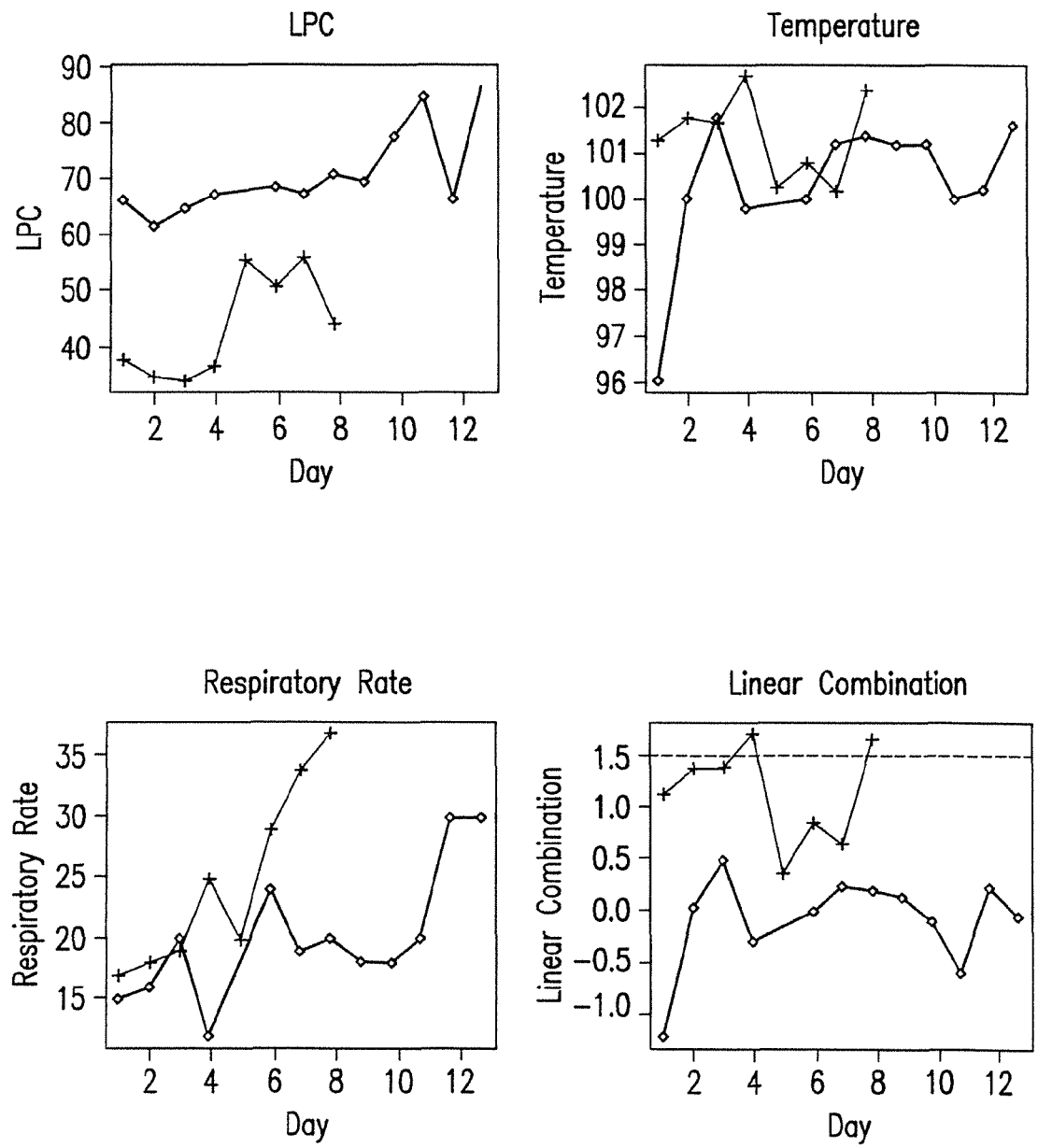
FIG. 8 is a graphical representation of daily marker values and log it(P(Sepsis)) values calculated for a SIRS test patient and a sepsis test patient.

FIG. 8 presents the marker values (LPC, Temp, RR) of Tables 22 and 23 on the same plots for comparative purposes. The blue line with circles represents the SIRS patient, M107, whereas the orange line with "±"s represents the septic patient, M163. The fourth plot presents log it(P(Sepsis)) values as a linear combination of LPC, Temp and RR markers. The grey dashed line on the fourth plot corresponds to a threshold of P(Sepsis)=0.81526 (i.e., (log it(P(Sepsis))=log it(threshold)=log it(0.81526)=1.484558).

Figure 9:
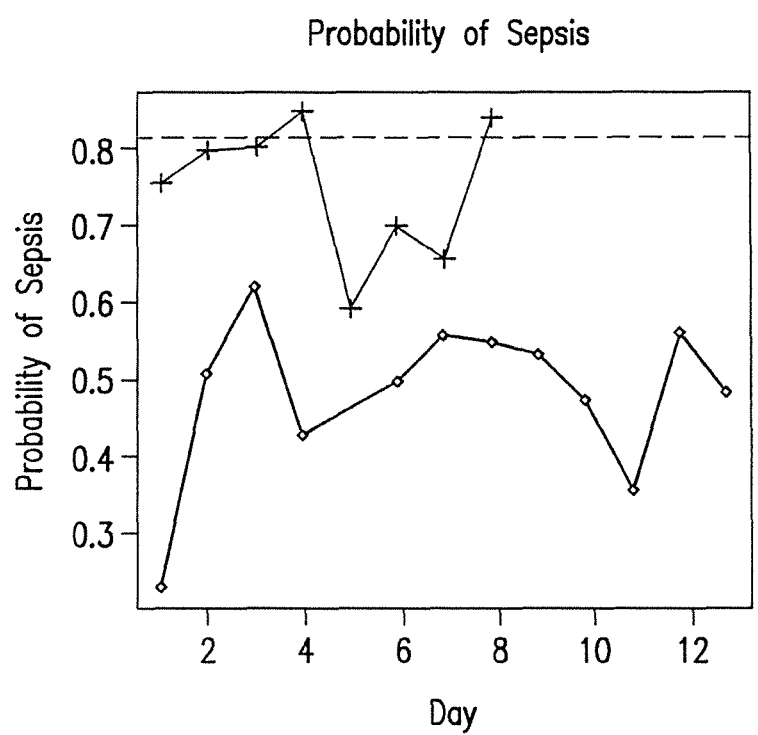
FIG. 9 is a graphical representation of the probability (P(Sepsis)) values calculated for a SIRS test patient and a sepsis test patient.

FIG. 9 presents the probability values, P(Sepsis), for probability of sepsis, calculated from the log it(P(Sepsis)) values. The grey dashed line corresponds to a threshold of P(Sepsis)=0.81526.

As can be seen in FIGS. 8 and 9, the septic patient's index values (represented either by the log it(P(Sepsis)) or P(Sepsis) values) crossed the threshold twice, once on day 4 and once on day 8. Such data demonstrates successful advanced detection of sepsis in a subject, in that a positive call for sepsis was made on day 4 or on day 8 of the study, prior to the development of clinical manifestations sufficient to support a clinical suspicion of sepsis in the patient. In the study, a sepsis diagnosis was made for sepsis patient, M163, on day 8, and monitoring stopped. According to the methods of the invention, intervention on behalf of the patient could be called on day 4, although alternative methods such as two above-threshold days in a row or a local average index (over some days) could be envisioned. Further, according to the methods of the invention, intervention on behalf of the patient could be called on days 1-3 and 5-7, days for which the septic patient's index values had not crossed the threshold, but for which the index values were still significantly elevated relative to the SIRS patient's values. Such data therefore demonstrates that assessment of likelihood of the onset of sepsis can also be made in a subject, prior to the onset of sepsis.

6.6 Example 6: Example Calculation of Individual Threshold Values of LPC, Temperature and Respiratory Rate Used to Detect Sepsis Example 6 presents example calculations of individual threshold amounts for LPC, temperature and respiratory rate markers used to detect sepsis.

As demonstrated in Example 5, when a model is based on a linear combination of several markers, the threshold on probabilities can be translated into a threshold on index values. If a test subject exceeds this threshold index value, sepsis is detected.

For a single marker, such as lysophosphatidylcholine alone, there is a one-to-one relationship between the marker value and a sepsis probability, such that the threshold on probabilities may be translated into a threshold on lysophosphatidylcholine values. Similarly, for temperature (or respiratory rate) used as a single marker, there also is a one-to-one relationship between the marker value and a sepsis probability, such that the threshold on probabilities may be translated into a threshold on temperature (or respiratory rate) values.

Example Calculation of Lysophosphatidylcholine Threshold Value

The lysophosphatidylcholine threshold value corresponds to a reference value below which sepsis is detected. Test subject LPC marker values less than the threshold value indicate sepsis. The example calculation of lysophosphatidylcholine threshold value uses a logistic regression algorithm. However, it will be apparent to one of skill in the art that any of the algorithms discussed above can be used to calculate threshold values for the individual markers of the invention.

The equation for the logistic regression "LPC" model using the coefficient and threshold values of Table 7 is:

$$\log it(P(\text{Sepsis}))=2.51269-0.03372\times \text{LPC}.$$

The inverse of the logistic function generates a probability for sepsis:

$$P(\text{Sepsis})=1-1/(1+e^{\{2.51269-0.03372\times \text{LPC}\}}).$$

The threshold on the probability scale (0.75502) can be translated into a direct threshold on LPC as follows:

$$\log it(0.75502)=1.125568=2.51269-0.03372\times \text{LPC}.$$

Solving for LPC yields:

$$\text{LPC}=-(1.125568-2.51269)/0.03372=41.13648.$$

Thus, the LPC threshold is 41.13648 units, which translates into approximately 41.14 µM. According to the model, sepsis is detected in a test subject with a LPC marker value less than 41.14 µM.

Example Calculation of Temperature and Respiratory Rate Threshold Values

Similarly, the equations for the logistic regression "Temp" and "RR" model using the coefficient and threshold values of Table 7 are:

$$\log it(0.72289)=-36.76293+0.36634*\text{Temp},$$

and $$\log it(0.66667)=-0.58421+0.02754*\text{RR},$$

respectively.

Using the inverse of the logistic functions to generate probabilities for sepsis, and translating the thresholds on the probability scales (0.722889 and 0.66667, respectively) into direct thresholds on Temp and RR, yields threshold values of Temp=39.43° C., and RR=46.38 breaths per minute. According to the Temp model, sepsis is detected in a test subject with a Temp marker value greater than 39.43° C. According to the RR model, sepsis is detected in a test subject with a RR marker value greater than 46.38 breaths per minute.

All publications and patent applications cited in this specification are herein incorporated by reference as if each individual publication or patent application were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A system for monitoring a SIRS-positive subject comprising:
   a computational device comprising a microprocessor capable of combining measurements obtained from a SIRS-positive subject into a result, wherein the measurements comprise:
   (a) measurements from a plurality of time points, prior to laboratory confirmation of a clinically significant infection causative of sepsis, of an amount of a compound according to formula (I)

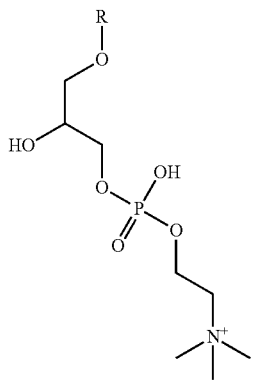

or a salt or solvate thereof, wherein R is $C_{10}$-$C_{22}$ acyl, in fluid or tissue of the SIRS-positive subject;

(b) measurements from a plurality of time points, prior to laboratory confirmation of a clinically significant infection causative of sepsis, of one or more clinical markers of the SIRS-positive subject selected from the group consisting of respiratory rate, temperature, heart rate, systolic blood pressure, diastolic blood pressure, mean artery pressure, white blood cell count, monocyte count, lymphocyte count, granulocyte count, neutrophil count, immature neutrophil to total neutrophil ratio, platelet count, serum creatinine concentration, urea concentration, lactate concentration, glucose concentration, base excess, $pO_2$ and $HCO_3^-$ concentration; provided respiratory rate and temperature are measured, and (c) measurements from a plurality of time points, prior to laboratory confirmation of a clinically significant infection causative of sepsis, of an amount of one or more biomarkers in fluid or tissue of the SIRS-positive subject selected from the group consisting of ACTH, activated partial thromboplastin, albumin, antithrombin III, bacterial DNA, carcinoembryonic antigen-related cell adhesion molecule 1 (CEACAM1), cell surface proteins CD-14 and CD-64, copeptin, C-reactive protein, cortisol, D-dimer, E-selectin, extra-hepatic arginase (ARG2), endotoxin, fibrin degrading products, high mobility group box 1 (HMGB1), HLA-DRA, interleukins IL-6, IL-8 and IL-10, LBP LPS-binding protein, plasminogen activator inhibitor-1, procalcitonin, protein C, protein S, prothrombin, soluble thrombomodulin, surface-bound tumor necrosis factor receptor I (sTNF-RI), surface-bound tumor necrosis factor receptor II (sTNF-RII), thrombin activatable fibrinolysis inhibitor, TRAF-interacting protein with a forkhead-associated domain (TIFA), triggering receptor expressed on myeloid cells 1, and tumor necrosis factor alpha (TNFα).

2. The system of claim 1, wherein R is saturated acyl.
3. The system of claim 1, wherein R is $C_{14}$-$C_{22}$ acyl.
4. The system of claim 1, wherein R is $C_{16}$-$C_{20}$ acyl.
5. The system of claim 1, wherein R is $C_{16}$-$C_{18}$ acyl.
6. The system of claim 1, wherein R is $C_{16}$ saturated acyl.
7. The system of claim 1, wherein R is $C_{18}$ saturated acyl.
8. The system of claim 1, wherein R is unbranched $C_{16}$-$C_{18}$ acyl.
9. The system of claim 1, wherein R is palmitoyl.
10. The system of claim 1, wherein R is stearoyl.
11. The system of claim 1, wherein the amount of a compound according to formula (I) was measured 12, 24, 36 or 48 hours prior to the onset of sepsis in said SIRS-positive patient.
12. The system of claim 1, wherein the one or more biomarkers comprise procalcitonin.
13. The system of claim 12, wherein the one or more clinical markers of the SIRS-positive subject comprises respiratory rate and temperature.
14. The system of claim 1, wherein the one or more clinical markers of the SIRS-positive subject comprises respiratory rate and temperature.
15. The system of claim 1, wherein the one or more biomarkers in fluid or tissue of the SIRS-positive subject comprises TRAF-interacting protein with a forkhead-associated domain (TIFA), extra-hepatic arginase (ARG2), carcinoembryonic antigen-related cell adhesion molecule 1 (CEACAM1), and human leukocyte antigen—antigen D-related alpha chain (HLA-DRA).
16. The system of claim 1, wherein the one or more clinical markers of the SIRS-positive subject comprises respiratory rate or temperature, and the one or more biomarkers comprises HLA-DRA.
17. The system of claim 1, wherein the compound according to formula (I) is lysophosphatidylcholine.
18. The system of claim 17, wherein the lysophosphatidylcholine comprises 1-O-palmitoyl-2-lyso-sn-glycero-3-phosphocholine and 1-O-stearoyl-2-lyso-sn-glycero-3-phosphocholine.
19. The system of claim 17, wherein free lysophosphatidylcholine is measured.
20. The system of claim 17, wherein bound lysophosphatidylcholine is measured.
21. The system of claim 17, wherein total lysophosphotatidylcholine is measured.
22. The system of claim 1, wherein the measurements comprise measurements of lysophosphatidylcholine, temperature, respiratory rate, procalcitonin, C-reactive protein, and Interleukin IL-6.
23. The system of claim 1, wherein the measurements comprise measurements of lysophosphatidylcholine, temperature, respiratory rate, and HLA-DR.
24. The system of claim 1, wherein the measurements comprise measurements of lysophosphatidylcholine, temperature, respiratory rate, ARG2, CEACAM1, HLA-DRA and TIFA.
25. The system of claim 1, wherein system further comprises a sensor module for measuring at least one of the one or more clinical markers.
26. The system of claim 1, wherein system further comprises a chemistry module for measuring the amount of the compound according to formula (I) and/or at least one of the one or more biomarkers.
27. The system of claim 1, further comprising a module capable of storing, displaying and/or transmitting the result.

* * * * *